United States Patent
Robinson et al.

(10) Patent No.: US 12,369,855 B2
(45) Date of Patent: *Jul. 29, 2025

(54) HYDRATION ASSESSMENT SYSTEM

(71) Applicant: Medici Technologies LLC, Albuquerque, NM (US)

(72) Inventors: Mark Ries Robinson, Albuquerque, NM (US); Elena A Allen, Albuquerque, NM (US); Cole Derby, Santa Clara, CA (US); Akifusa Nakazawa, Mountain View, CA (US); Haiping Liao, Chicago, IL (US); Michael Chad Makay, Santa Clara, CA (US)

(73) Assignee: Medici Technologies LLC, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/421,071

(22) Filed: Jan. 24, 2024

(65) Prior Publication Data
US 2024/0206809 A1   Jun. 27, 2024

Related U.S. Application Data

(63) Continuation of application No. 17/049,508, filed as application No. PCT/US2020/038825 on Jun. 19, 2020, now Pat. No. 11,471,102.
(Continued)

(51) Int. Cl.
*A61B 5/00* (2006.01)
*A61B 5/02* (2006.01)
(Continued)

(52) U.S. Cl.
CPC ........ *A61B 5/4875* (2013.01); *A61B 5/02028* (2013.01); *A61B 5/0205* (2013.01); *A61B 5/486* (2013.01); *A61B 5/6826* (2013.01); *A61B 5/6843* (2013.01); *A61B 5/7278* (2013.01); *A61B 5/7282* (2013.01); *G16H 40/63* (2018.01);
(Continued)

(58) Field of Classification Search
CPC . A61B 5/4875; A61B 5/02028; A61B 5/0205; A61B 5/486; A61B 5/6826; A61B 5/6843; A61B 5/7278; A61B 5/7282; A61B 5/02416; A61B 5/1116; A61B 5/7405;
(Continued)

(56) References Cited

U.S. PATENT DOCUMENTS 5,277,181 A    1/1994   Mendelson
5,499,627 A    3/1996   Steuer
(Continued)

OTHER PUBLICATIONS

U.S. Appl. No. 17/048,508, Robinson.
(Continued)

*Primary Examiner* — Shirley X Jian
(74) *Attorney, Agent, or Firm* — V Gerald Grafe

(57) ABSTRACT

The present invention provides methods and systems that provide for reliable, convenient, and noninvasive assessment of hydration status. The methods and apparatuses can use the temporal sequence of the aortic value opening and closing along with the user's body position to derive parameters that determine the hydration status of the user. The user can use this information to make near-term lifestyle changes that can improve physical performance, health, and general wellbeing.

20 Claims, 40 Drawing Sheets

Related U.S. Application Data

(60) Provisional application No. 62/864,465, filed on Jun. 20, 2019.

(51) Int. Cl.
*A61B 5/0205* (2006.01)
*G16H 40/63* (2018.01)
*A61B 5/024* (2006.01)
*A61B 5/11* (2006.01)

(52) U.S. Cl.
CPC ......... *A61B 5/02416* (2013.01); *A61B 5/1116* (2013.01); *A61B 5/7405* (2013.01); *A61B 5/742* (2013.01); *A61B 5/7455* (2013.01); *A61B 2562/0219* (2013.01)

(58) Field of Classification Search
CPC ................. A61B 5/742; A61B 5/7455; A61B 2562/0219; G16H 40/63
See application file for complete search history.

(56) References Cited

U.S. PATENT DOCUMENTS

| | | | |
|---|---|---|---|
| 5,964,701 | A | 10/1999 | Asada et al. |
| 6,402,690 | B1 | 6/2002 | Rhee et al. |
| 6,594,511 | B2 | 7/2003 | Stone |
| 6,606,509 | B2 | 8/2003 | Schmitt |
| 6,675,029 | B2 | 1/2004 | Monfre et al. |
| 6,819,950 | B2 | 11/2004 | Mills |
| 7,277,741 | B2 | 10/2007 | Debreczeny |
| 7,608,045 | B2 | 10/2009 | Mills |
| 8,180,419 | B2 | 5/2012 | Debreczeny |
| 8,568,330 | B2 | 10/2013 | Mollicone |
| 8,721,555 | B2 | 5/2014 | Westbrook et al. |
| 8,989,832 | B2 | 3/2015 | Debreczeny et al. |
| 9,005,129 | B2 * | 4/2015 | Venkatraman ......... A61B 5/721 600/502 |
| D791,764 | S | 7/2017 | von Badinski et al. |
| 9,711,060 | B1 | 7/2017 | Lusted et al. |
| D811,260 | S | 2/2018 | Koskinen |
| 9,924,902 | B2 * | 3/2018 | Banet ................... A61B 5/6831 |
| D817,496 | S | 5/2018 | Stirn et al. |
| 9,958,904 | B2 | 5/2018 | von Badinski et al. |
| 10,085,657 | B2 | 10/2018 | Moon et al. |
| 10,105,095 | B2 | 10/2018 | Kinnunen |
| 10,178,973 | B2 | 1/2019 | Venkatraman |
| 10,281,953 | B2 | 5/2019 | von Badinski et al. |
| 10,993,663 | B2 * | 5/2021 | Banet ................... A61B 5/6823 |
| 11,471,102 | B2 * | 10/2022 | Robinson ............... G16H 40/63 |
| 11,911,179 | B2 * | 2/2024 | Robinson ............. A61B 5/7221 |
| 2010/0298677 | A1 | 11/2010 | Lu et al. |
| 2012/0179011 | A1 | 7/2012 | Moon et al. |
| 2012/0220835 | A1 * | 8/2012 | Chung ................. A61B 5/6898 600/301 |
| 2013/0261468 | A1 * | 10/2013 | Semler ................. A61B 5/6898 600/473 |
| 2014/0276119 | A1 * | 9/2014 | Venkatraman ..... A61B 5/02405 600/509 |
| 2015/0148623 | A1 | 5/2015 | Benaron |
| 2015/0182164 | A1 | 7/2015 | Utter, II |
| 2016/0066827 | A1 | 3/2016 | Workman et al. |
| 2016/0106366 | A1 * | 4/2016 | Banet ..................... A61B 5/029 600/382 |
| 2016/0166161 | A1 | 6/2016 | Yang et al. |
| 2016/0213267 | A1 | 7/2016 | Laakkonen et al. |
| 2016/0246326 | A1 | 8/2016 | von Badinski et al. |
| 2016/0338639 | A1 | 11/2016 | Myers et al. |
| 2017/0042477 | A1 | 2/2017 | Haverinen et al. |
| 2017/0156036 | A1 | 6/2017 | Laakkonen et al. |
| 2019/0298172 | A1 | 10/2019 | Mahmud et al. |
| 2020/0000345 | A1 | 1/2020 | Connor |
| 2020/0008686 | A1 * | 1/2020 | Khair .................... A61B 5/029 |
| 2020/0085360 | A1 | 3/2020 | Yuan et al. |
| 2022/0096007 | A1 * | 3/2022 | Robinson ........... A61B 5/02028 |

OTHER PUBLICATIONS

Hassan,S.; Turner, P., Systolic time intervals: a review of the method in the non-invasive investigation of cardiac function in, 1983, Journal : Postgraduate Medical Journal.

Harms, Mark P M; Wesseling, Karel H; Pott, Frank; Jenstrup, Morten; Goudoever,Jeroen Van; Secher, Niels H; Lieshout, Johannes J Van, Continuous stroke volume monitoring by modelling flow from non-invasive measurement of arterial pressure in humans under orthostatic stress, 1999, Journal : The Biochemical Society and the Medical Research Society.

Harley, Alexander; Starmer, C. Frank; Greenfield, Joseph C., Pressure-flow studies in man. An evaluation of the duration of the phases of systole, 1969, Journal : Journal of Clinical Investigation.

Grum, D. F.; Dauchot, P. J., Correlation of Systolic Time Intervals with Stroke Volume in Man, 1980, Book Section: Springer Berlin Heidelberg.

Braunschweig, F, Continous haemodynamic monitoring during withdrawal of diuretics in patients with congestive heart failure, 2002, Journal: European Heart Journal.

Chan, Gregory S H; Middleton, Paul M; Celler, Branko G; Wang, Lu; Lovell, Nigel H, Automatic detection of left ventricular ejection time from a finger photoplethysmographic pulse oximetry waveform: comparison with Doppler, 2007, Journal: Physiological Measurement.

Lewis, R P; Rittogers, S E; Froester, W F; Boudoulas, H, A critical review of the systolic time intervals., 1977, Journal: Circulation.

Cziesler, Cody R, Using Least Variance for Robust Extraction of Systolic Time Intervals, 2014, Thesis: Rochester Institute of Technology.

Stafford, R. W.; Harris, W. S.; Weissler, A. M., Left Ventricular Systolic Time Intervals as Indices of Postural Circulatory Stress, 1970, Journal: Circulation.

Sperry, Brett W.; Campbell, Joseph; Yanavitski, Marat; Kapadia, Samir; Tang, W.H. Wilson; Hanna, Mazen, Peripheral Venous Pressure Measurements in Patients With Acute Decompensated Heart Failure (PVP-HF), 2017, Journal: Circulation: Heart Failure.

Rubal, B. J.; Geer, M. R.; Bickell, W. H., Effects of pneumatic antishock garment inflation in normovolemic, 1989, Journal : Journal of Applied Physiology.

Quarry-Pigott, Veronica; Chirife, Raul; Spodick, David H., Ejection Time by Ear Densitogram and Its Derivative: Clinical and Physiologic Applications, 1973, Journal: Circulation.

Jansen,J.R.C.; Schreuder,J.J.; Mulier,J.P.; Smith, N.T.; Settels,J.J.; Wesseling, K.H., A comparison of cardiac output derived from the arterial pressure wave against thermodilution in cardiac surgery, 2001, Journal: British Journal of Anaesthesia.

Abay, T. Y.; Kyriacou, P. A., Accuracy of reflectance photoplethysmography on detecting, 2015, Conference: IEEE.

Alastruey, Jordi; Passerini, Tiziano; Formaggia, Luca; Peiró, Joaquim, Physical determining factors of the arterial pulse waveform: theoretical analysis and calculation using the 1-D, 2012, Journal : Journal of Engineering Mathematics.

Alastruey,Jordi; Parker, Kim H; Sherwin, Spencer J, Arterial pulse wave haemodynamics, 2012, Conference.

Allen, J; Murray, A, Age-related changes in peripheral pulse timing characteristics at the ears, 2002, Journal : Journal of Human Hypertension.

Jang, Dae-Geun; Farooq, Umar; Park, Seung-Hun; Hahn, Minsoo, An automatic signal detection algorithm for the digital volume pulse, 2010, Conference: IEEE.

He, David Da; Winokur, Eric S.; Sodini, Charles G., An Ear-Worn Vital Signs Monitor, 2015, Journal: IEEE Transactions on Biomedical Engineering.

Armstrong, Lawrence E.; Pumerantz, Amy C.; Fiala, Kelly A.; Roti, Melissa W.; Kavouras, Stavros A.; Casa, Douglas J.; Maresh, Carl M., Human Hydration Indices: Acute and Longitudinal Reference Values, 2010, Journal: International Journal of Sport Nutrition and Exercise Metabolism.

Couceiro, Ricardo; Carvalho, P; Paiva, R P; Henriques, J; Quintal, I; Antunes, M; Muehlsteff, J; Eickholt, C; Brinkmeyer, C; Kelm, M;

(56) References Cited

OTHER PUBLICATIONS

Meyer, C, Assessment of cardiovascular function from multi-Gaussian fitting of a finger photoplethysmogram, 2015, Journal: Physiological Measurement.
Awad, Aymen A.; Stout, Robert G.; Ghobashy, M. Ashraf M.; Rezkanna, Hoda A.; Silverman, David G.; Shelley, Kirk H., Analysis of the Ear Pulse Oximeter Waveform, 2006, Journal : Journal of Clinical Monitoring and Computing.
Barnas, Michel G W; Boer, Walther H; Koomans, Hein A, Hemodynamic Patterns and Spectral Analysis of Heart Rate Variability during, 1999, Journal : J Am Soc Nephrol.
Baruch, Martin C; Warburton, Darren ER; Bredin, Shannon SD; Cote, Anita; Gerdt, David W; Adkins, Charles M, Pulse Decomposition Analysis of the digital arterial pulse during hemorrhage simulation, 2011, Journal: Nonlinear Biomedical Physics.
Bendjelid, Karim, The pulse oximetry plethysmographic curve revisited:, 2008, Journal: Current Opinion in Critical Care.
Bonomi, Alberto G.; Goris, Annelies H.C.; Yin, Bin; Westerterp, Klaas R., Detection of Type, Duration, and Intensity of Physical Activity Using an Accelerometer:, 2009, Journal: Medicine & Science in Sports & Exercise.
Smith, D; Craige, E, Mechanism of the dicrotic pulse., 1986, Journal: Heart.
Broccard, Alain F., Cardiopulmonary interactions and volume status assessment, 2012, Journal : Journal of Clinical Monitoring and Computing.
Nieminen, T.; Koobi, T.; Turjanmaa, V., Can stroke volume and cardiac output be determined reliably in a tilt-table test using the pulse contour method?, 2000, Journal: Clinical Physiology.
Cannesson, Maxime; Attof, Yassin; Rosamel, Pascal; Desebbe, Olivier; Joseph, Pierre; Merton, Olivier; Bastien, Olivier; Lehot, Jean-Jacques, Respiratory Variations in Pulse Oximetry Plethysmographic Waveform Amplitude to Predict Fluid Responsiveness in the Operating Room:, 2007, Journal : Anesthesiology.
Cannesson, Maxime; Aboy, Mateo; Hofer, Christoph K; Rehman, Mohamed, Pulse pressure variation: where are we today?, 2011, Journal : Journal of Clinical Monitoring and Computing.
Miller,J C; Horvath,S M, Cardiac Output During Human Sleep, 1976, Journal : avation, space and environmental medicine.
De Wilde, R. B. P.; Schreuder, J. J.; van den Berg, P. C. M.; Jansen,J. R. C., An evaluation of cardiac output by five arterial pulse contour techniques during cardiac surgery, 2007, Journal : Anaesthesia.
Cavallaro, Fabio; Sandroni, Claudio; Marano, Cristina; La Torre, Giuseppe; Mannocci, Alice; De Waure, Chiara; Bello, Giuseppe; Maviglia, Riccardo; Antonelli, Massimo, Diagnostic accuracy of passive leg raising for prediction of fluid responsiveness in adults: systematic review and meta-analysis of clinical studies, 2010, Journal : Intensive Care Medicine.
Chan, Gregory S. H.; Middleton, Paul M.; Celler, Branko G.; Wang, Lu; Lovell, Nigel H., Change in pulse transit time and pre-ejection period during head-up tilt-induced progressive central hypovolaemia, 2007, Journal : Journal of Clinical Monitoring and Computing.
Middleton, Paul M.; Chan, Gregory S. H.; O'Lone, Emma; Steel, Elizabeth; Carroll, Rebecca; Celler, Branko G.; Lovell, Nigel H., Changes in left ventricular ejection time and pulse transit time derived from finger photoplethysmogram and electrocardiogram during moderate haemorrhage, 2009, Journal : Clinical Physiology and Functional Imaging.
Epstein, Stephen E.; Beiser, G. David; Stampfer, Morris; Robinson, Brian F.; Braunwald, Eugene, Characterization of the Circulatory Response to Maximal Upright Exercise in Normal Subjects and Patients with Heart Disease, 1967, Journal : Circulation.
Chernbumroong, S.; Atkins, A. S.; Hongnian Yu, Activity classification using a single wrist-worn accelerometer, 2011, Conference: IEEE.
Chernbumroong, Saisakul; Cang, Shuang; Atkins, Anthony; Yu, Hongnian, Elderly activities recognition and classification for applications in assisted living, 2013, Journal: Expert Systems with Applications.
Su, Ho-Ming; Lin, Tsung-Hsien; Hsu, Po-Chao; Chu, Chun-Yuan; Lee, Wen-Hsien; Chen, Szu-Chia; Lee, Chee-Siong; Voon, Wen-Chol; Lai, Wen-Ter; Sheu, Sheng-Hsiung, A Comparison between Brachial and Echocardiographic Systolic Time Intervals, 2013, Journal: PLoS ONE.
Convertino, Victor A.; Moulton, Steven L.; Grudic, Gregory Z.; Rickards, Caroline A.; Hinojosa-Laborde, Carmen; Gerhardt, Robert T.; Blackbourne, Lorne H.; Ryan, Kathy L., Use of Advanced Machine-Learning Techniques for Noninvasive Monitoring of Hemorrhage:, 2011, Journal : The Journal of Trauma: Injury, Infection, and Critical Care.
Convertino, Victor A.; Wirt, Michael D.; Glenn,John F.; Lein, Brian C., The Compensatory Reserve for Early and Accurate Prediction of Hemodynamic Compromise: A Review, 2016, Journal : SHOCK.
Coudray, Alice; Romand, Jacques-André; Treggiari, Miríam; Bendjelid, Karim, Fluid responsiveness in spontaneously breathing patients: A review of indexes used in intensive care:, 2005, Journal: Critical Care Medicine.
Hoeksel, S. A. A. P., et al; J.A. Blom, PhD,3 and J.J. Schreuder,MD, PhD1, Detection of Dicrotic Notch in Arterial Pressure Signals, 1997, Journal : Journal of Clinical Monitoring.
Duarte-Dyck, D.; Guillén-Peralta, A.; Romo-Cárdenas, G.; Callorda-Fedeczko, L., Development of an Anatomical Measurement and Data Analysis Tool Based on the Kinect Sensor for Physical Rehabilitation Applications., 2015, Book Section: Springer International Publishing.
Dong, Zhou-zhou, Passive leg raising as an indicator of fluid responsiveness in patients with severe sepsis, 2012, Journal: World Journal of Emergency Medicine.
Ewing, D J; Campbell, I W; Murray, A; Neilson,J M; Clarke, B F, Immediate heart-rate response to standing: simple test for autonomic neuropathy in diabetes., 1978, Journal : BMJ.
Carsetti, Andrea; Cecconi, Maurizio; Rhodes, Andrew, Fluid bolus therapy: monitoring and predicting fluid responsiveness, 2015, Journal : Current Opinion in Critical Care.
Javed, Faizan; Middleton, Paul M; Malouf, Philip; Chan, Gregory S H; Savkin, Andrey V; Lovell, Nigel H; Steel, Elizabeth; Mackie, James, Frequency spectrum analysis of finger photoplethysmographic waveform variability during haemodialysis, 2010, Journal : Physiological Measurement.
Geerts, Bart; de Wilde, Rob; Aarts, Leon; Jansen, Jos, Pulse Contour Analysis to Assess Hemodynamic Response to Passive Leg Raising, 2011, Journal : Journal of Cardiothoracic and Vascular Anesthesia.
Electrophysiology, Task Force of the European Society of Cardiology the North American Society of Pacing, Heart rate variability: standards of measurement, physiological interpretation, and clinical use., 1996, Journal : Eur Heart J.
Hagan, R. D.; Buono, M. J.; Singh, S.; Blood, C. G., Heart Rate Variability and Changes in Blood Volume:, 2000, Blog Post: http://www.dtic.mil/docs/citations/ADA389810.
Hickey, Michelle; Phillips, Justin P.; Kyriacou, Panayiotis, Venous pooling and drainage affects photoplethysmographic signals at different vertical hand positions, 2015, Conference: SPIE BiOS.
Hinojosa-Laborde, Carmen; Rickards, Caroline A.; Ryan, Kathy L.; Convertino, Victor A., Heart Rate Variability during Simulated Hemorrhage with Lower Body Negative Pressure in High and Low Tolerant, 2011, Journal : Frontiers in Physiology.
Cokkinos, D V; Heimonas, E T; Demopoulos, J N; Harralambakis, A; Tsartsalis, G; Gardikas, C D, Influence of heart rate increase on uncorrected pre-ejection period/left ventricular ejection time (PEP/LVET) ratio in normal individuals., 1976, Journal : Heart.
Mertens, H. M.; Mannebach, H.; Trieb, G.; Gleichmann, U., Influence of heart rate on systolic time intervals: Effects of atrial pacing versus, 1981, Journal : Clinical Cardiology.
Jellema, Wilbert Tjebbe, Cardiovascular dynamics in hypovolemic and septic shock, 2005, Thesis: s.n.].
Kavouras, Stavros A., Assessing hydration status:, 2002, Journal : Current Opinion in Clinical Nutrition and Metabolic Care.
Kudat, H; Akkaya, V; Sozen, Ab; Salman, S; Demirel, S; Ozcan, M; Atilgan, D; Yilmaz, Mt; Guven, O, Heart Rate Variability in Diabetes Patients, 2006, Journal : Journal of International Medical Research.

(56) References Cited

OTHER PUBLICATIONS

Kuntamalla, Srinivas; Ram Gopal Reddy, L., An Efficient and Automatic Systolic Peak Detection Algorithm for Photoplethysmographic Signals, 2014, Journal : International Journal of Computer Applications.

Lansdorp, B.; Lemson, J.; van Putten, M.J.A.M.; de Keijzer, A.; van der Hoeven, J.G.; Pickkers, P., Dynamic indices do not predict volume responsiveness in routine clinical practice, 2012, Journal : British Journal of Anaesthesia.

Lanspa, Michael J.; Grissom, Colin K.; Hirshberg, Eliotte L.; Jones, Jason P.; Brown, Samuel M., Applying Dynamic Parameters to Predict Hemodynamic Response to Volume Expansion in Spontaneously Breathing Patients With Septic Shock:, 2013, Journal : Shock.

Latham, R D; Westerhof, N; Sipkema, P; Rubal, B J; Reuderink, P; Murgo, J P, Regional wave travel and reflections along the human aorta: a study with six simultaneous micromanometric, 1985, Journal : Circulation.

Lee, Qim Y; Redmond, Stephen J; Chan, Gregory SH; Middleton, Paul M; Steel, Elizabeth; Malouf, Philip; Critoph, Cristopher; Flynn, Gordon; O'Lone, Emma; Lovell, Nigel H, Estimation of cardiac output and systemic vascular resistance using a multivariate regression model with features selected from the finger photoplethysmogram and routine cardiovascular measurements, 2013, Journal : BioMedical Engineering OnLine.

Levick, J. R., An introduction to cardiovascular, 1991, Book : Butterworths.

Levine, B D; Lane, L D; Buckey, J C; Friedman, D B; Blomqvist, C G, Left ventricular pressure-volume and Frank-Starling relations in endurance athletes. Implications for orthostatic, 1991, Journal : Circulation.

Magder, S, From PV loop to Starling curve, 0, Presentation.

Maizel,Julien; Airapetian, Norair; Lorne, Emmanuel; Tribouilloy, Christophe; Massy, Ziad; Slama, Michel, Diagnosis of central hypovolemia by using passive leg raising, 2007, Journal : Intensive Care Medicine.

Marik, Paul E., Techniques for Assessment of Intravascular Volume in Critically Ill Patients, 2009, Journal : Journal of Intensive Care Medicine.

Marik, P. E.; Lemson, J., Fluid responsiveness: an evolution of our understanding, 2014, Journal : British Journal of Anaesthesia.

Marik, Paul E; M onnet, Xavier; Teboul, Jean-Louis, Hemodynamic parameters to guide fluid therapy, 2011, Journal : Annals of Intensive Care.

Quwaider, Muhannad; Biswas, Subir, Body Posture Identification using Hidden Markov Model with a, 2008, Conference: ICST.

Mathie, M. J.; Celler, B. G.; Lovell, N. H.; Coster, A. C. F., Classification of basic daily movements using a triaxial accelerometer, 2004, Journal : Medical & Biological Engineering & Computing.

McGrath, Susan P.; Ryan, Kathy L.; Wendelken, Suzanne M.; Rickards, Caroline A.; Convertino, Victor A., Pulse Oximeter Plethysmographic Waveform Changes in Awake, Spontaneously Breathing, Hypovolemic Volunteers:, 2011, Journal : Anesthesia & Analgesia.

Middleton, Paul M.; Chan, Gregory S. H.; O'Lone, Emma; Steel, Elizabeth; Carroll, Rebecca; Celler, Branko G.; Lovell, Nigel H., Spectral Analysis of Finger Photoplethysmographic Waveform Variability in a Model of Mild to Moderate Haemorrhage, 2008, Journal : Journal of Clinical Monitoring and Computing.

Millasseau, Sandrine C; Ritter, James M; Takazawa, Kenji; Chowienczyk, Philip J, Contour analysis of the photoplethysmographic pulse measured at the finger:, 2006, Journal : Journal of Hypertension.

Monnet, Xavier; Rienzo, Mario; Osman, David; Anguel, Nadia; Richard, Christian; Pinsky, Michael R.; Teboul, Jean-Louis, Passive leg raising predicts fluid responsiveness in the critically ill*:, 2006, Journal : Critical Care Medicine.

Monnet, Xavier; Lamia, Bouchra; Teboul, Jean-Louis, Pulse oximeter as a sensor of fluid responsiveness: do we have our finger, 2005, Journal : Critical Care.

Monnet, Xavier; Teboul, Jean-Louis, Passive leg raising: five rules, not a drop of fluid!, 2015, Journal : Critical Care.

Moulton, Steven L.; Mulligan, Jane; Grudic, Greg Z.; Convertino, Victor A., Running on empty? The compensatory reserve index:, 2013, Journal : Journal of Trauma and Acute Care Surgery.

Najafi, B.; Aminian, K.; Loew, F.; Blanc,Y.; Robert, P.A., Measurement of stand-sit and sit-stand transitions using a miniature gyroscope and its application in fall risk evaluation in the elderly, 2002, Journal : IEEE Transactions on Biomedical Engineering.

Najafi, B.; Aminian, K.; Paraschiv-Ionescu, A.; Loew, F.; Bula, C.J.; Robert, P., Ambulatory system for human motion analysis using a kinematic sensor: monitoring of daily physical activity in the elderly, 2003, Journal : IEEE Transactions on Biomedical Engineering.

Natalini, Giuseppe; Rosano, Antonio; Taranto, Maria; Faggian, Barbara; Vittorielli, Elena; Bernardini, Achille, Arterial Versus Plethysmographic Dynamic Indices to Test Responsiveness for Testing Fluid Administration in Hypotensive Patients:, 2006, Journal : Anesthesia & Analgesia.

Zaidi, S N; Collins, S M, Orthostatic stress and area underthe curve of photoplethysmography waveform, 2016, Journal : Biomedical Physics & Engineering Express.

Peng, Rong-Chao; Zhou, Xiao-Lin; Lin, Wan-Hua; Zhang, Yuan-Ting, Extraction of Heart Rate Variability from Smartphone Photoplethysmograms, 2015, Journal : Computational and Mathematical Methods in Medicine.

Perel, Azriel; Minkovich, Leonid; Preisman, Sergey; Abiad, Michel; Segal, Eran; Coriat, Pierre, Assessing Fluid-Responsiveness by a Standardized Ventilatory Maneuver: The Respiratory Systolic Variation Test:, 2005, Journal: Anesthesia & Analgesia.

Wardhan, Richa; Shelley, Kirk, Peripheral venous pressure waveform:, 2009, Journal : Current Opinion in Anaesthesiology.

Meredith, D. J.; Clifton, D.; Charlton, P.; Brooks, J.; Pugh, C. W.; Tarassenko, L., Photoplethysmographic derivation of respiratory rate: a review of relevant physiology, 2012, Journal : Journal of Medical Engineering & Technology.

De Backer, Daniel; Pinsky, Michael R., Can one predict fluid responsiveness in spontaneously breathing patients?, 2012, Book Section: Springer Berlin Heidelberg.

Pizov, Reuven; Tamir, Ada; Gelman, Simon, Arterial and Plethysmographic Waveform Analysis in Anesthetized, 2010, Journal : Anesthesiology.

Pizov, R.; Eden, A.; Bystritski, D.; Kalina, E.; Tamir, A.; Gelman, S., Hypotension during gradual blood loss: waveform variables response and absence of tachycardia, 2012, Journal: British Journal of Anaesthesia.

Reddy, K.A.; George, B.; Kumar, V.J., Use of Fourier Series Analysis for Motion Artifact Reduction and Data Compression of Photoplethysmographic Signals, 2009, Journal : IEEE Transactions on Instrumentation and Measurement.

Anter, A. M.; Bondok, R. S., Peripheral venous pressure is an alternative to central venous pressure in paediatric surgery patients, 2004, Journal : Acta Anaesthesiologica Scandinavica.

Raamat, Rein; Jagomägi, Kersti; Talts, Jaak, Calibrated photoplethysmographic estimation of digital pulse volume and arterial compliance, 2007, Journal : Clinical Physiology and Functional Imaging.

Farcy, David; Jain, Ashika; Dalley, Michael; Scalea, Thomas, Review: Pitfalls in Using Central Venous Pressure as a Marker of Fluid Responsiveness, 2016, Journal : Emergency Medicine.

Rickards, Caroline A.; Vyas, Nisarg; Ryan, Kathy L.; Ward, Kevin R.; Andre, David; Hurst, Gennifer M.; Barrera, Chelsea R.; Convertino, Victor A., Are you bleeding? Validation of a machine-learning algorithm for determination of blood volume status: application to remote triage, 2014, Journal : Journal of Applied Physiology.

Rowlands, Alex V.; Yates, Thomas; Olds, Tim S.; Davies, Melanie; Khunti, Kamlesh; Edwardson, Charlotte L., Sedentary Sphere: Wrist-Worn Accelerometer-Brand Independent Posture Classification, 2016, Journal : Medicine & Science in Sports & Exercise.

(56) References Cited

OTHER PUBLICATIONS

Rubins, Uldis, Finger and ear photoplethysmogram waveform analysis by fitting with Gaussians, 2008, Journal : Medical & Biological Engineering & Computing.
Sandberg, Frida; Bailon, Raquel; Hernando, David; Laguna, Pablo; Martinez, Juan Pablo; Solem, Kristian; Sornmo, Leif, Prediction of Intradialytic Hypotension using PPG and ECG, 2013, Journal : Computing in Cardiology.
Sandberg, Frida; Bailón, Raquel; Hernando, David; Laguna, Pablo; Martínez, Juan Pablo; Solem, Kristian; Sörnmo, Leif, Prediction of hypotension in hemodialysis patients, 2014, Journal : Physiological Measurement.
Schafer, Kristin; Van Sickle, Christina; Hinojosa-Laborde, Carmen; Convertino, Victor A., Physiologic mechanisms underlying the failure of the "shock index" as a tool for accurate assessment of patient status during progressive simulated, 2013, Journal : Journal of Trauma and Acute Care Surgery.
Schroeder, E. B.; Chambless, L. E.; Liao, D.; Prineas, R. J.; Evans, G. W.; Rosamond, W. D.; Heiss, G., Diabetes, Glucose, Insulin, and Heart Rate Variability: The Atherosclerosis Risk in Communities (ARIC) study, 2005, Journal: Diabetes Care.
Scully, Christopher G.; Selvaraj, Nandakumar; Romberg, Frederick W.; Wardhan, Richa; Ryan, John; Florian, John P.; Silverman, David G.; Shelley, Kirk H.; Chon, Ki H., Using Time-Frequency Analysis of the Photoplethysmographic Waveform to Detect the Withdrawal of 900 mL of Blood:, 2012, Journal : Anesthesia & Analgesia.
Selvaraj, Nandakumar; Shelley, Kirk H.; Silverman, David G.; Stachenfeld, Nina; Galante, Nicholas; Florian, John P.; Mendelson, Yitzhak; Chon, Ki H., A Novel Approach Using Time-Frequency Analysis of Pulse-Oximeter Data to Detect Progressive Hypovolemia in Spontaneously Breathing Healthy Subjects, 2011, Journal : IEEE Transactions on Biomedical Engineering.
Selvaraj, N.; Scully, C. G.; Shelley, K. H.; Silverman, D. G.; Chen, K. H., Early detection of spontaneous blood loss using amplitude modulation of Photoplethysmogram, 2011, Conference: IEEE.
Shackelford, Stacy A.; Colton, Katharine; Stansbury, Lynn G.; Galvagno, Samuel M.; Anazodo, Amechi N.; DuBose, Joseph J.; Hess, John R.; Mackenzie, Colin F., Early identification of uncontrolled hemorrhage after trauma: Current status and future direction, 2014, Journal : Journal of Trauma and Acute Care Surgery.
Smorenberg, Annemieke; Lust, Erik J.; Beishuizen, Albertus; Meijer, Jan H.; Verdaasdonk, Ruud M.; Groeneveld, A. B. Johan, Systolic time intervals vs invasive predictors of fluid responsiveness after coronary artery bypass surgery, 2013, Journal : European Journal of Cardio-Thoracic Surgery.
Solem, Kristian; Olde, Bo; Sörnmo, Leif, Prediction of Intradialytic Hypotension Using Photoplethysmography, 2010, Journal : IEEE Transactions on Biomedical Engineering.
Soubrier, Stéphane; Saulnier, Fabienne; Hubert, Hervé; Delour, Pierre; Lenci, Hélène; Onimus, Thierry; Nseir, Saad; Durocher, Alain, Can dynamic indicators help the prediction of fluid responsiveness in spontaneously breathing critically ill patients?, 2007, Journal : Intensive Care Medicine.
Berlin, David A; Bakker, Jan, Starling curves and central venous, 2015, Journal : Critical Care.
Stewart, Camille L.; Mulligan, Jane; Grudic, Greg Z.; Convertino, Victor A.; Moulton, Steven L., Detection of low-volume blood loss: Compensatory reserve versus traditional vital signs, 2014, Journal : Journal of Trauma and Acute Care Surgery.
Stok, Wim J.; Westerhof, Berend E.; Karemaker, John M., Changes in finger-aorta pressure transfer function during and after exercise, 2006, Journal : Journal of Applied Physiology.
Istenes, Ildikó; Körei, Anna Erzsébet; Putz, Zsuzsanna; Németh, Nóra; Martos, Timea; Keresztes, Katalin; Kempler, Miklós Soma; Erzsébet, Véagi Orsolya; Vargha, Péter; Kempler, Péter, Heart rate variability is severely impaired among type 2 diabetic patients with hypertension: Hypertension and Diabetes Cause Severely Impaired HRV, 2014, Journal : Diabetes/Metabolism Research and Reviews.
Tahvanainen, Anna; Leskinen, Miia; Koskela, Jenni; Ilveskoski, Erkki; Nordhausen, Klaus; Oja, Hannu; Kähönen, Mika; Kööbi, Tiit; Mustonen, Jukka; Pörsti, Ilkka, Ageing and cardiovascular responses to head-up tilt in healthy subjects, 2009, Journal : Atherosclerosis.
Tavakolian, Kouhyar; Dumont, Guy A.; Houlton, Geoffrey; Blaber, Andrew P., Precordial Vibrations Provide Noninvasive Detection of Early-Stage Hemorrhage:, 2014, Journal : Shock.
Hickey, M; Phillips, J P; Kyriacou, P A, The effect of vascular changes on the photoplethysmographic signal at different hand elevations, 2015, Journal : Physiological Measurement.
Pan, Rémy C Martin-Du; Benoit, Raymond; Girardier, Lucia, The role of body position and gravity in the symptoms and treatment of various medical diseases, 2004, Journal: SWISS MED WKLY
Grubb, Blair P.; Kosinski, Daniel, Tilt Table Testing: Concepts and Limitations, 1997, Journal: Pacing and Clinical Electrophysiology.
Troiano, Richard P; McClain, James J; Brychta, Robert J; Chen, Kong Y, Evolution of accelerometer methods for physical activity research, 2014, Journal: British Journal of Sports Medicine.
Trost, Stewart G; Zheng, Yonglei; Wong, Weng-Keen, Machine learning for activity recognition: hip versus wrist data, 2014, Journal : Physiological Measurement.
Uretzky, G; Palti, Y, A method for comparing transmitted and reflected light photoelectric, 1971, Journal : Journal of Applied Physiology.
Jayasree, V K, Selected Cardiovascular Studies Based on Photoplethysmography Technique, 2009, Thesis: Cochin University of Science and Technology.
Van Sickle, Christina; Schafer, Kristin; Mulligan, Jane; Grudic, Gregory Z.; Moulton, Steven L.; Convertino, Victor A., A Sensitive Shock Index for Real-Time Patient Assessment During Simulated Hemorrhage, 2013, Journal : Aviation, Space, and Environmental Medicine.
van Hees, Vincent T.; Fang, Zhou; Langford, Joss; Assah, Felix; Mohammad, Anwar; da Silva, Inacio C. M.; Trenell, Michael I.; White, Tom; Wareham, Nicholas J.; Brage, Søren, Autocalibration of accelerometer data for free-living physical activity assessment using local gravity and temperature: an evaluation on four continents, 2014, Journal : Journal of Applied Physiology.
Magder, S., How Does Volume Make the Blood Go Around?, 2015, Book Section: Springer International Publishing.
Vistisen, Simon Tilma; Juhl-Olsen, Peter; Frederiksen, Christian Alcaraz; Kirkegaard, Hans, Variations in the pre-ejection period induced by deep breathing do not predict the hemodynamic response to early haemorrhage in healthy, 2014, Journal : Journal of Clinical Monitoring and Computing.
Wang, Chien-Hao; Lu, Cheng-Wei; Lin, Tzu-Yu; Abbod, Maysam F; Shieh, Jiann-Shing, An Assessment of Pulse Transit Time for Detecting Heavy Blood Loss During Surgical Operation, 2012, Journal : The Open Biomedical Engineering Journal.
Antonelli, L.; Ohley, W.; Khamlach, R., Dicrotic notch detection using wavelet transform analysis, 1994, Conference: IEEE.
Di Rienzo, M.; Meriggi, P.; Vaini, E.; Castiglioni, P.; Rizzo, F., 24h seismocardiogram monitoring in ambulant subjects, 2012, Conference: IEEE.
Weissler, Arnold M.; Peeler, Robert G.; Roehll, Walter H., Relationships between left ventricular ejection time, stroke volume, and heart rate in normal individuals and patients, 1961, Journal : American Heart Journal.
Kunze, Kai; Lukowicz, Paul; Junker, Holger; Tröster, Gerhard, Where am I: Recognizing On-body Positions of Wearable Sensors, 2005, Book Section: Springer Berlin Heidelberg.
Zöllei, Éva; Bertalan, Viktória; Németh, Andrea; Csábi, Péter; László, Ildikó; Kaszaki, József; Rudas, László, Non-invasive detection of hypovolemia or fluid responsiveness in spontaneously breathing subjects, 2013, Journal : BMC Anesthesiology.
Critchley, Lester A.; Yang, Xiao X.; Lee, Anna, Assessment of Trending Ability of Cardiac Output Monitors by Polar Plot Methodology, 2011, Journal : Journal of Cardiothoracic and Vascular Anesthesia.
Adams, J. D.; Sekiguchi, Yasuki; Suh, Hyun-Gyu; Seal, Adam D.; Sprong, Cameron A.; Kirkland, Tracie W.; Kavouras, Stavros A., Dehydration Impairs Cycling Performance, Independently of Thirst: A Blinded Study, 2018, Journal : Medicine & Science in Sports & Exercise.

(56) References Cited

OTHER PUBLICATIONS

Killgore, William D. S.; Balkin, Thomas J.; Wesensten, Nancy J., Impaired decision making following 49 h of sleep deprivation, 2009, Journal : Journal of Sleep Research.
Villiger, M; Stoop, R; Vetsch, T; Hohenauer, E; Pini, M; Clarys, P; Pereira, F; Clijsen, R, Evaluation and review of body fluids saliva, sweat and tear compared to biochemical hydration assessment, 2018, Journal : European Journal of Clinical Nutrition.
Armstrong, Lawrence E, Assessing hydration status: the elusive gold standard, 2007, Journal : Journal of the American College of Nutrition.
Spodick, David H.; Doi, Yoshinori L.; Bishop, Richard L.; Hashimoto,Tetsuo, Systolic time intervals reconsidered: Reevaluation of the preejection period: Absence of relation to heart rate, 1984, Journal : The American Journal of Cardiology.
Teboul, J.-L.; Lamia, B.; Monnet, X., Assessment of Fluid Responsiveness in Spontaneously Breathing Patients, 2007, Conference: Springer Berlin Heidelberg.
Amoroso, P.; Greenwood, R. N., Posture and central venous pressure measurement in circulatory volume, 1989, Journal : Lancet.
Bhave, Gautam; Neilson, Eric G., Volume Depletion Versus Dehydration: How Understanding the Difference Can Guide Therapy, 2011, Journal : American Journal of Kidney Diseases.
Hickey, Michelle; Phillips, Justin P.; Kyriacou, Panayiotis A., Investigation of peripheral photoplethysmographic morphology changes induced during a hand-, 2016, Journal : Journal of Clinical Monitoring and Computing.
Convertino, Victor A.; Howard, Jeffrey T.; Hinojosa-Laborde, Carmen; Cardin, Sylvain; Batchelder, Paul; Mulligan, Jane; Grudic, Gregory Z.; Moulton, Steven L.; MacLeod, David B., Individual-Specific, Beat-to-beat Trending of Significant Human Blood Loss: The Compensatory Reserve, 2015, Journal : Shock (Augusta, Ga.).
Stems, Richard; Emmett, Michael, Etiology, clinical manifestations, and diagnosis of volume depletion in adults, 2019, Document: UpToDate.
Weissler, Arnold M.; Harris, Leonard C.; White, George D., Left ventricular ejection time index in man, 1963, Journal : Journal of Applied Physiology.
Michels, Nathalie; Clays, Els; Buyzere, Marc De; Vanaelst, Barbara; Henauw, Stefaan De; Sioen, Isabelle, Children's Sleep and Autonomic Function: Low Sleep Quality Has an Impact on Heart Rate Variability, 2013, Journal : Sleep.
Lance, V Q; Spodick, D H, Heart rate—left ventricular ejection time relations. Variations during postural change and cardiovascular challenges., 1976, Journal : Heart.
Willems, Jos L.; Roelandt, Jos; De Geest, Hilaire; Kesteloot, Hugo; Joossens, Jozef V., The Left Ventricular Ejection Time in Elderly Subjects, 1970, Journal : Circulation.
Sammito, Stefan; Böckelmann, Irina, Reference values for time- and frequency-domain heart rate variability, 2016, Journal : Heart Rhythm.
Shaffer, Fred; Ginsberg, J. P., An Overview of Heart Rate Variability Metrics and Norms, 2017, Journal : Frontiers in Public Health.
Bonnet, M.H.; Arand, D. L., Heart rate variability: sleep stage, time of night, and arousal influences, 1997, Journal : Electroencephalography and Clinical Neurophysiology.
Aktaruzzaman, Md; Rivolta, Massimo Walter; Karmacharya, Ruby; Scarabottolo, Nello; Pugnetti, Luigi; Garegnani, Massimo; Bovi, Gabriele; Scalera, Giovanni; Ferrarin, Maurizio; Sassi, Roberto, Performance comparison between wrist and chest actigraphy in combination with heart rate variability for sleep classification, 2017, Journal : Computers in Biology and Medicine.
Xiao, Meng; Yan, Hong; Song, Jinzhong; Yang, Yuzhou; Yang, Xianglin, Sleep stages classification based on heart rate variability and random forest, 2013, Journal : Biomedical Signal Processing and Control.
Liang, Zilu; Ploderer, Bernd, Sleep Tracking in the Real World: A Qualitative Study into Barriers for, 2016, Conference.

Taelman, Joachim; Vandeput, S.; Spaepen, A.; Van Huffel, S., Influence of Mental Stress on Heart Rate and Heart Rate Variability, 2009, Book Section: Springer Berlin Heidelberg.
Butte, Nancy F.; Ekelund, Ulf; Westerterp, Klaas R., Assessing Physical Activity Using Wearable Monitors: Measures of Physical Activity, 2012, Journal : Medicine & Science in Sports & Exercise.
Tamura, Toshiyo; Maeda, Yuka; Sekine, Masaki; Yoshida, Masaki, Wearable Photoplethysmographic Sensors—Past and Present, 2014, Journal : Electronics.
Jihyoung Lee; Matsumura, Kenta; Yamakoshi, Ken-ichi; Rolfe, Peter; Tanaka, Shinobu; Yamakoshi, Takehiro, Comparison between red, green and blue light reflection photoplethysmography for heart rate monitoring during motion, 2013, Conference: IEEE.
Sokwoo Rhee; Boo-Ho Yang; Asada, H. H., Artifact-resistant power-efficient design of finger-ring plethysmographic sensors, 2001, Journal : IEEE Transactions on Biomedical Engineering.
Sola, J.; Castoldi, S.; Chetelat, O.; Correvon, M.; Dasen, S.; Droz, S.; Jacob, N.; Kormann, R.; Neumann, V.; Perrenoud, A.; Pilloud, P.; Verjus, C.; Viardot, G., SpO2 Sensor Embedded in a Finger Ring: design and implementation, 2006, Conference: IEEE.
Sola, Josep; Chetelat, Olivier, Combination of multiple light paths in pulse oximetry: the finger ring example, 2007, Conference: IEEE.
Maeda, Yuka; Sekine, Masaki; Tamura, Toshiyo, Relationship Between Measurement Site and Motion Artifacts in Wearable Reflected Photoplethysmography, 2011, Journal : Journal of Medical Systems.
Maeda, Yuka; Sekine, Masaki; Tamura, Toshiyo, The Advantages of Wearable Green Reflected Photoplethysmography, 2011, Journal : Journal of Medical Systems.
Jongpal Kim; Takhyung Lee; Jihoon Kim; Hyoungho Ko, Ambient light cancellation in photoplethysmogram application using alternating sampling and charge, 2015, Conference: IEEE.
Paradkar, Neeraj; Chowdhury, Shubhajit Roy, Cardiac arrhythmia detection using photoplethysmography, 2017, Conference: IEEE.
Huo, Yunlong; Kassab, Ghassan S., A Scaling Law of Vascular Volume, 2009, Journal : Biophysical Journal.
Riley, Alyssa A.; Arakawa, Yoko; Worley, Sarah; Duncan, Brian W.; Fukamachi, Kiyotaka, Circulating Blood Volumes: A Review of Measurement Techniques and a Meta-Analysis in Children:, 2010, Journal : ASAIO Journal.
Baron, Kelly Glazer; Reid, Kathryn J., Circadian misalignmentand health, 2014, Journal : International Review of Psychiatry.
Hall, Martica; Vasko, Raymond; Buysse, Daniel; Ombao, Hernando; Chen, Qingxia; Cashmere, J. David; Kupfer, David; Thayer, Julian F., Acute Stress Affects Heart Rate Variability During Sleep:, 2004, Journal : Psychosomatic Medicine.
Grandner, Michael A., The Cost of Sleep Lost: Implications for Health, Performance, and the Bottom Line, 2018, Journal : American Journal of Health Promotion.
Armstrong, Lawrence E.; Johnson, Evan C.; Bergeron, Michael F., COUNTERVIEW: Is Drinking to Thirst Adequate to Appropriately Maintain Hydration Status During Prolonged, 2016, Journal : Wilderness & Environmental Medicine.
De Paula, Erich Vinicius, Tides within ourselves: how posture can affect blood volume, blood cells and clinical reasoning, 2017, Journal: Revista Brasileira de Hematologia e Hemoterapia.
Rodriguez, Gustavo J.; Cordina, Steve M.; Vazquez, Gabriela; Suri, M. Fareed K.; Kirmani, Jawad F.; Ezzeddine, Mustapha A.; Qureshi, Adnan I., The Hydration Influence on the Risk of Stroke (THIRST) Study, 2009, Journal : Neurocritical Care.
Frangeskou, M.; Lopez-Valcarcel, B.; Serra-Majem, Lluis, Dehydration in the elderly: A review focused on economic burden, 2015, Journal : The journal of nutrition, health & aging.
Chan, J., Water, Other Fluids, and Fatal Coronary Heart Disease: The Adventist Health Study, 2002, Journal : American Journal of Epidemiology.
Asogwa, Clement; Lai, Daniel, A Review on Opportunities to Assess Hydration in Wireless Body Area, 2017, Journal : Electronics.
Khalil, Sami; Mohktar, Mas; Ibrahim, Fatimah, The Theory and Fundamentals of Bioimpedance Analysis in Clinical Status Monitoring and Diagnosis of Diseases, 2014, Journal : Sensors.

(56) References Cited

OTHER PUBLICATIONS

Sawka, Michael N.; Cheuvront, Samuel N.; Kenefick, Robert W., Hypohydration and Human Performance: Impact of Environment and Physiological Mechanisms, 2015, Journal : Sports Medicine.

Trangmar, Steven J.; González-Alonso, José, Heat, Hydration and the Human Brain, Heart and Skeletal Muscles, 2019, Journal : Sports Medicine.

Jéquier, E; Constant, F, Water as an essential nutrient: the physiological basis of hydration, 2010, Journal : European Journal of Clinical Nutrition.

Kenefick, Robert W., Drinking Strategies: Planned Drinking Versus Drinking to Thirst, 2018, Journal : Sports Medicine.

Koulmann, Nathalie; Jimenez, Chantal; Regal, Damien; Bolliet, Philippe; Launay, Jean-Claude; Savourey, Gustave; Melin, Bruno, Use of bioelectrical impedance analysis to estimate body fluid compartments after acute variations of the body hydration level:, 2000, Journal : Medicine & Science in Sports & Exercise.

O'Brien, C.; Young, A. J.; Sawka, M. N., Bioelectrical Impedance to Estimate Changes in Hydration Status, 2002, Journal : International Journal of Sports Medicine.

Vella, CA, A review of the stroke volume response to upright exercise in healthy subjects, 2005, Journal : British Journal of Sports Medicine.

Van Der Hoeven, G M; Clerens, P J; Donders, J J; Beneken, J E; Vonk, J T, A study of systolic time intervals during uninterrupted exercise., 1977, Journal : Heart.

Wiens, Andrew D, Detecting Aortic Valve Opening and Closing from Distal Body Vibrations, 2016, Journal : rXiv preprint arXiv.

Miyamoto, Y.; Higuchi, J.; Abe, Y.; Hiura, T.; Nakazono, Y.; Mikami, T., Dynamics of cardiac output and systolic time intervals in supine and upright exercise, 1983, Journal : Journal of Applied Physiology.

Spodick, David H.; Quarry-Pigott, Veronica M., Effects of Posture on Exercise Performance: Measurement by, 1973, Journal : Circulation.

Mettler, S., and C. H. Mannhart., Hydration, drinking and exercise performance, 2017, Journal : Swiss Sports Ex Med.

O'Rourke, Michael F; Gallagher, David E, Pulse wave analysis., 1996, Journal : Journal of hypertension. Supplement: official journal of the International Society of Hypertension.

Fan, Zhaopeng; Zhang, Gong; Lia, Simon, Pulse Wave Analysis, 2011, Book Section: IntechOpen.

Morimoto, Taketoshi, Termoregulation and Body Fluids: Role of Blood Volume and Central Venous Pressure, 1990, Journal : The Japanese journal of physiology.

Levick, J. Rodney, An introduction to cardiovascular physiology, 2013, Book Section: Butterworth-Heinemann.

Sami, A., et al., Passive leg rising and pulse contour, 2006, Conference.

Weissler, Arnold M., Leonard C. Harris, and George D. White, Left Ventricular Ejection Time in man, 1963, Journal : Journal of applied physiology.

Cherpanath, Thomas GV, et a, Predicting fluid responsiveness by passive leg raising: a systematic review and meta-analysis of 23 clinical trials., 2016, Journal : Critical care medicine.

Fatigue Science, Science-of-Sleep-WoThe Science of Sleep and Workplace Fatigue, 2019, Blog Post.

Stohr, Eric, The Effect of Heat Stress, Dehydration and Exercise on Global Left Ventricular Function and Mechanics in Healthy, 2010, Thesis: Columbia University.

Ajith Kumar, P. C., & Ananthapadmanabha, T. V., Ajith Kumar, P. C., and T. V. Ananthapadmanabha. Heart rate variability using Shannon energy, 2006, Journal : MSRSAS.

Frazier, John; Hatib, Feras, Getting ml beat from mmHg: Arterial Pressure-based Cardiac Output, 2008, Document: Edwards Lifesciences.

Balijepalli, C.; Lösch, C.; Bramlage, P.; Erbel, R.; Humphries, K. H.; Jöckel, K.-H.; Moebus, S., Percentile distribution of blood pressure readings in 35683 men and women aged 18 to 99 years, 2014, Journal : Journal of Human Hypertension.

Brophy-Williams, Ned; Driller, Matthew William; Shing, Cecilia Mary; Fell, James William; Halson, Shona Leigh, Confounding compression: the effects of posture, sizing and garment type on measured interface pressure in sports compression clothing, 2015, Journal : Journal of Sports Sciences.

Coltman, Celeste E.; McGhee, Deirdre E.; Steele, Julie R., Bra strap orientations and designs to minimise bra strap discomfort and pressure during sport and exercise in, 2015, Journal : Sports Medicine—Open.

Bafekrpour, Ehsan; Dyskin, Arcady; Pasternak, Elena; Molotnikov, Andrey; Estrin, Yuri, Internally architectured materials with directionally asymmetric friction, 2015, Journal : Scientific Reports.

\* cited by examiner

| Measurement Approach | Measurement Sensitivity to Potential Error Source | | | | |
|---|---|---|---|---|---|
| | Vasodilation/ Vasoconstriction | Skin Contaminants | Sensor Position Relative to Heart | Tissue-Sensor Interface | Isotonic / Hypertonic |
| Pulse Size | High | Low | High | Low | Low |
| Perfusion | High | Low | High | Low | Low |
| Tissue Spectroscopy | High | High | Medium | High | Low |
| Blood Spectroscopy | Medium | Medium | Medium | High | Low |
| Sweat Analysis | Low | High | Low | High | High |
| Bioimpedance | Medium | Low | Medium | Low | High |
| Aortic Valve Timing | Low | Low | Low | Low | Low |

FIG. 3

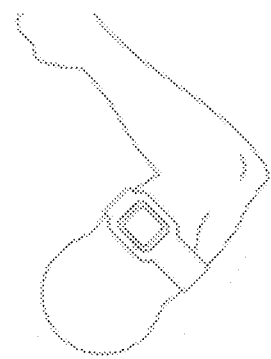
FIG. 8C  Arm Sensor
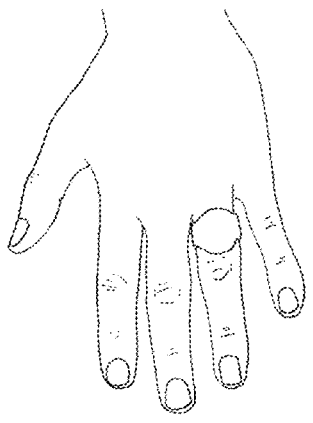
FIG. 8B  Ring Sensor
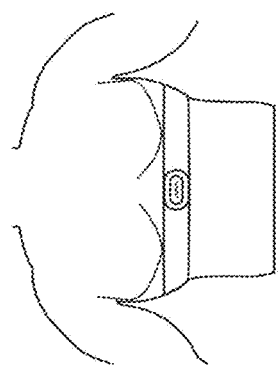
FIG. 8E  Chest Sensor
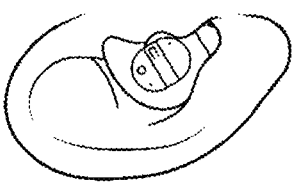
FIG. 8D  Ear Sensor
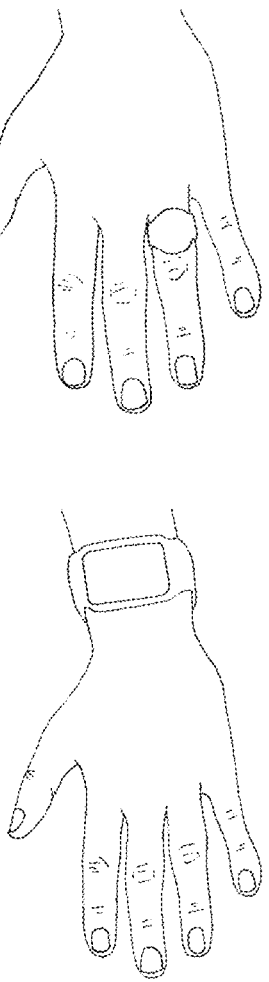
FIG. 8A  Wrist Sensor FIG. 3 Heart rate—left ventricular ejection time relation during isometric handgrip (IHG) exercise in sitting position. Measurements cover range of 15, 30, 50, and 100 per cent maximum voluntary contraction.

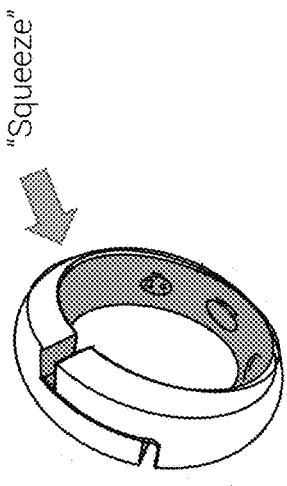
FIG. 23C "Squeeze"
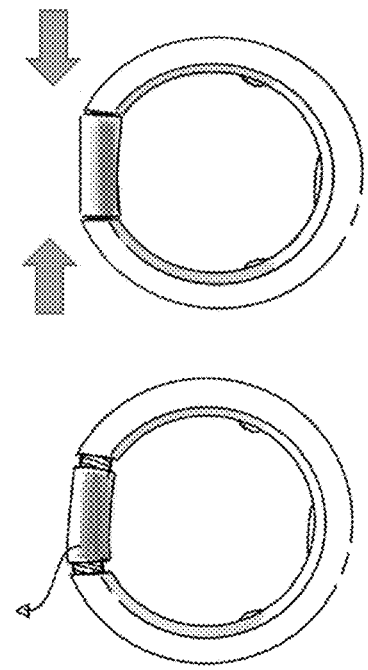
FIG. 23E
"Roll"
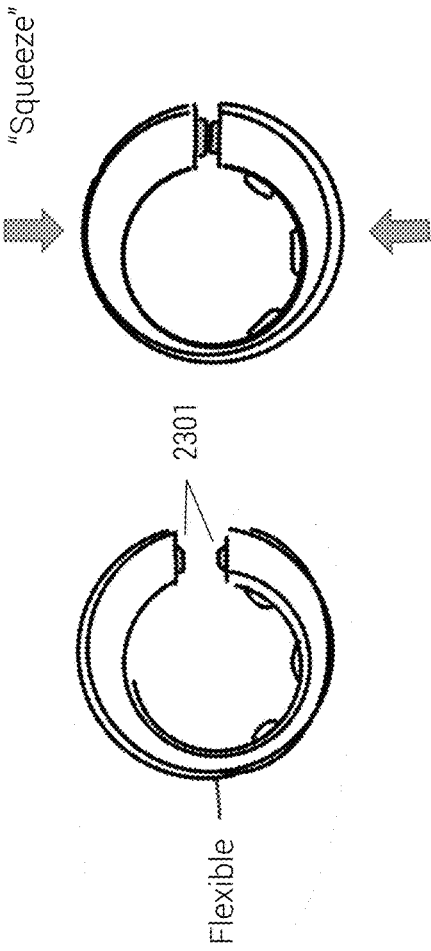
FIG. 23A
FIG. 23B "Squeeze"
2301
Flexible
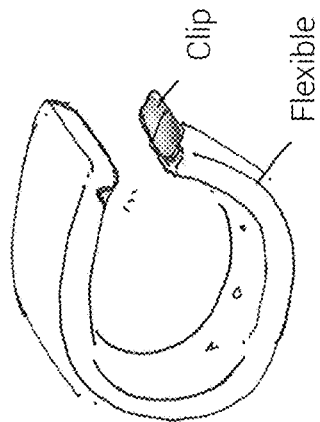
FIG. 23D
Clip
Flexible

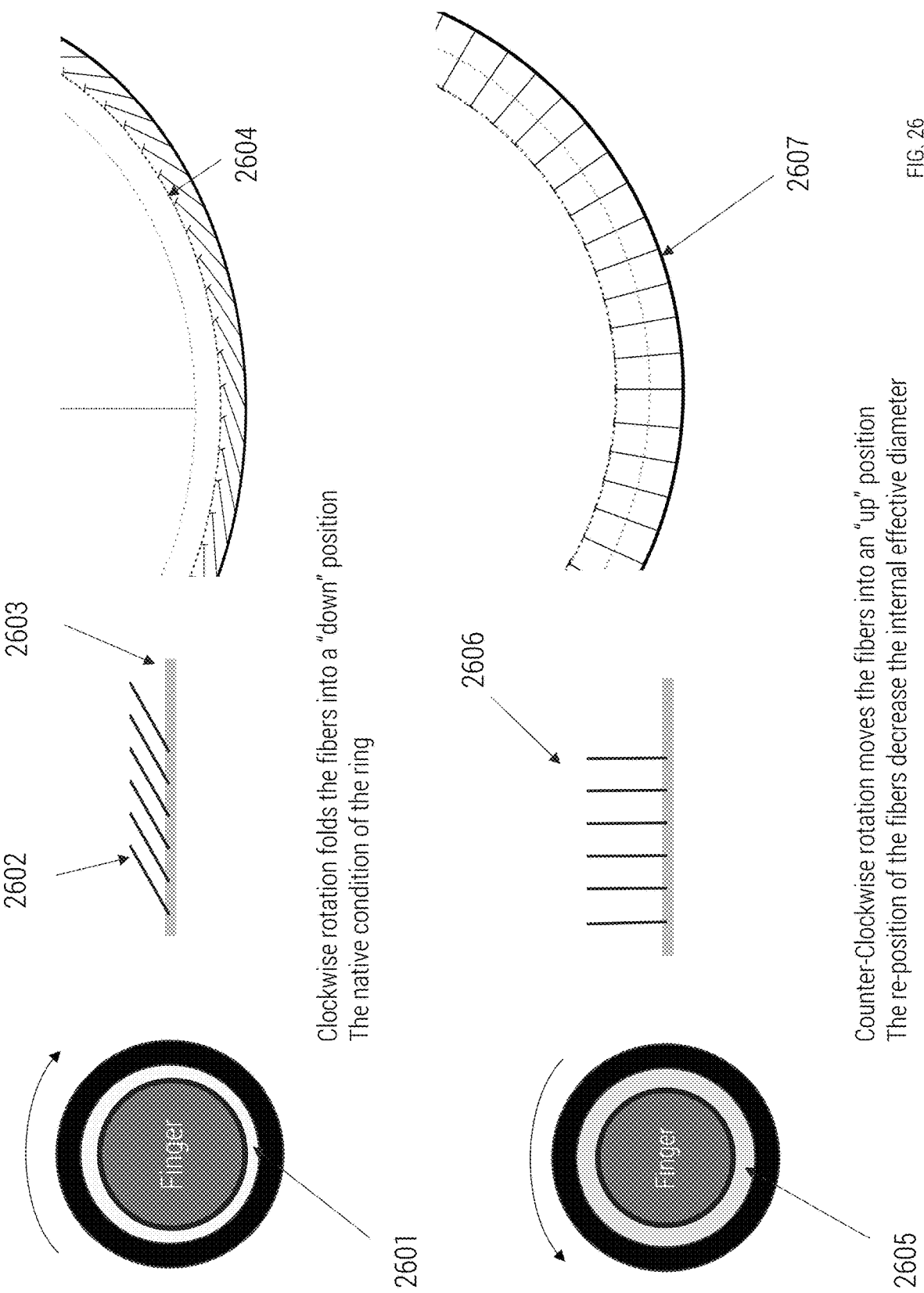

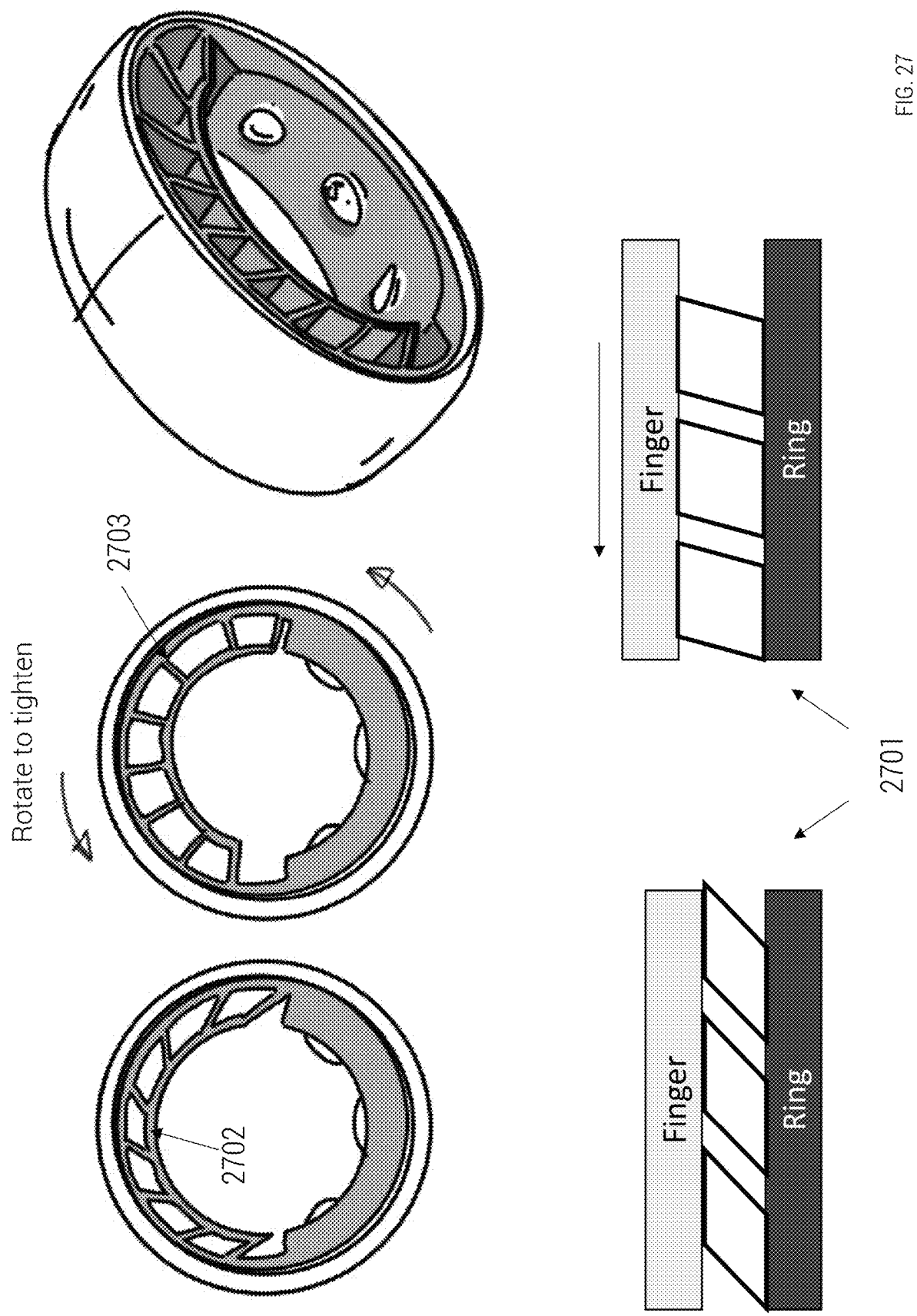

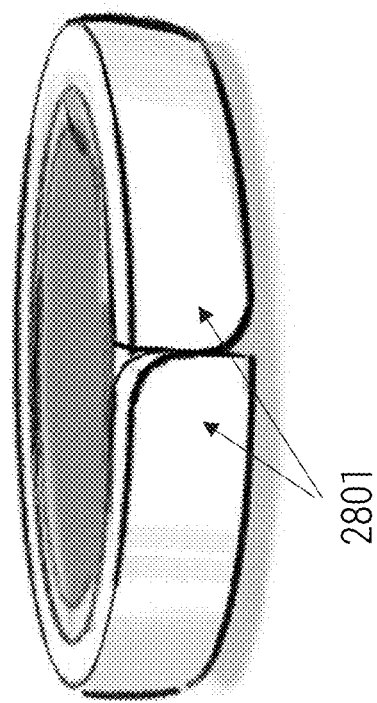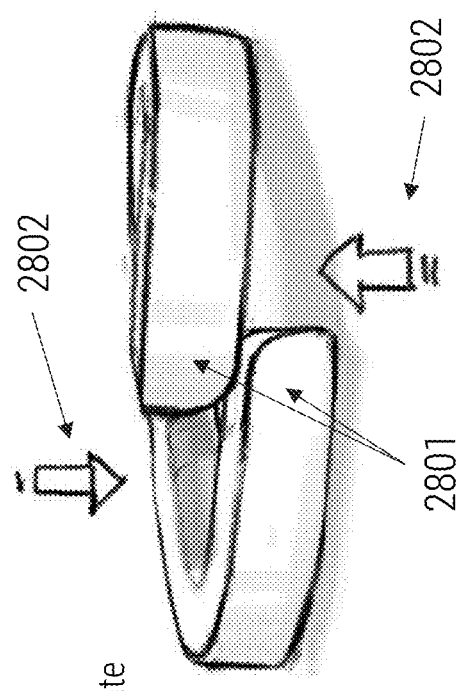
FIG. 28A Worn State
FIG. 28B Measurement State
FIG. 28

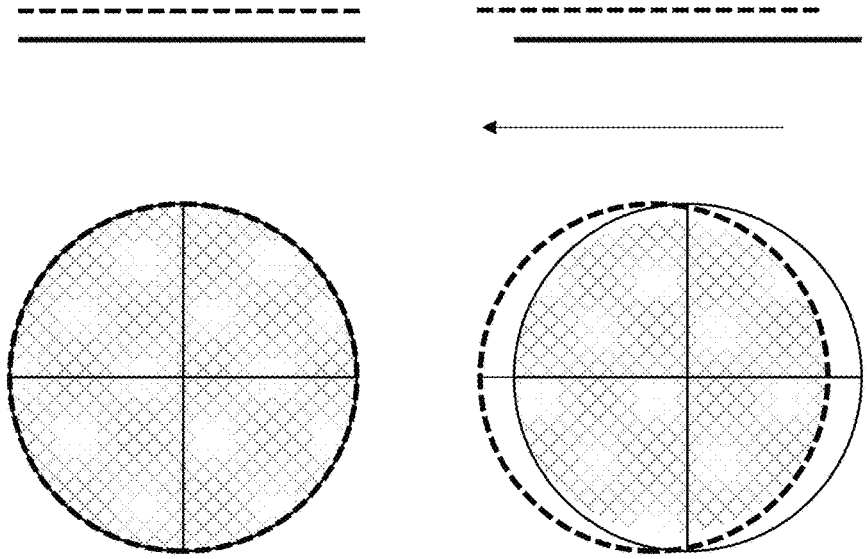
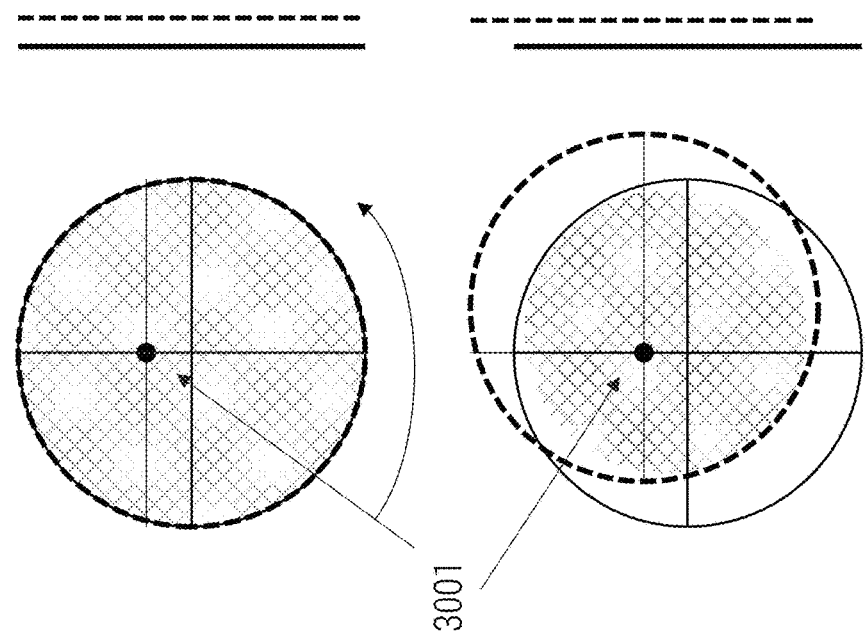
FIG. 30

Hydration Measurement Process, Example Embodiment 2

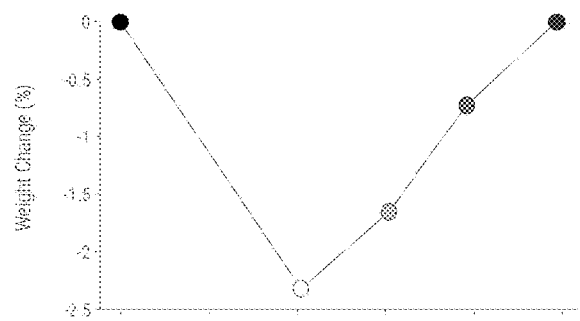
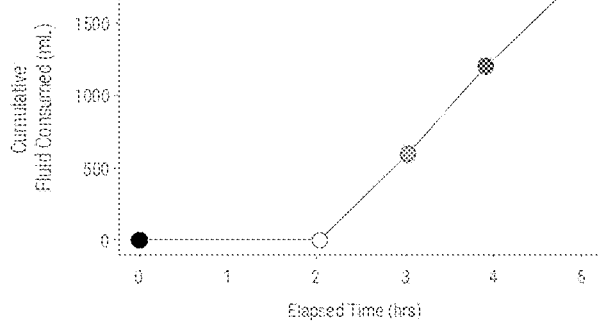
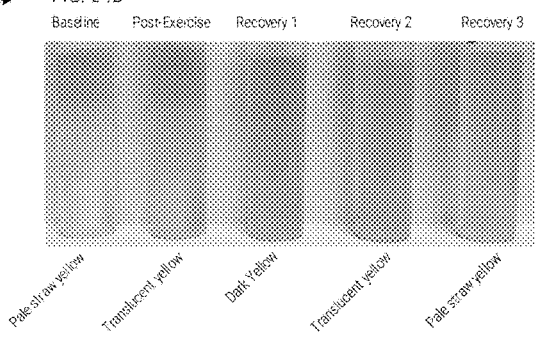
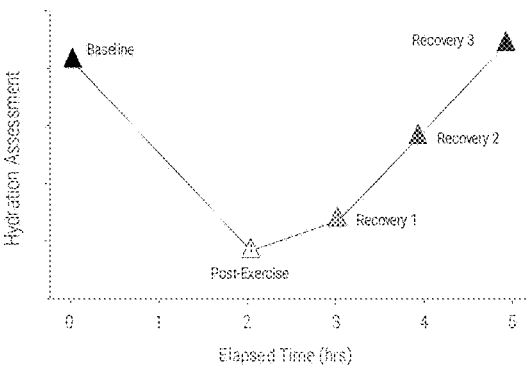

FIG. 35A
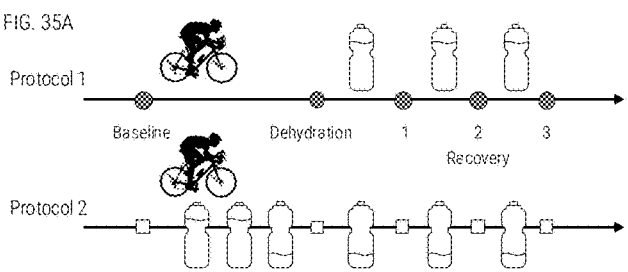
FIG. 35B
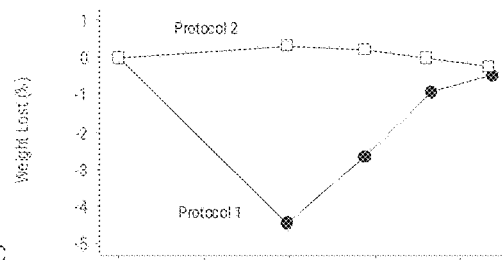
FIG. 35C
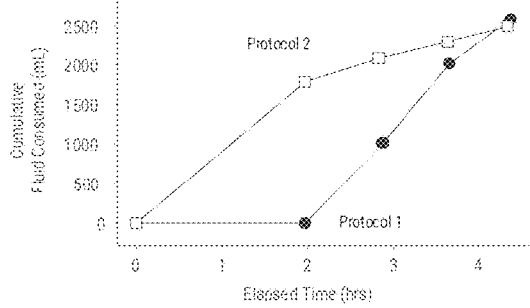
FIG. 35D
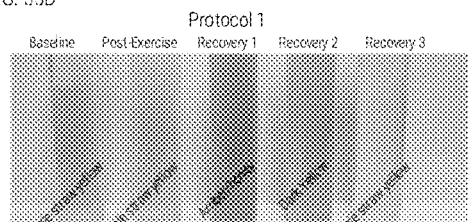
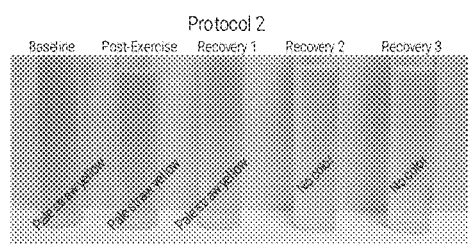
FIG. 35E
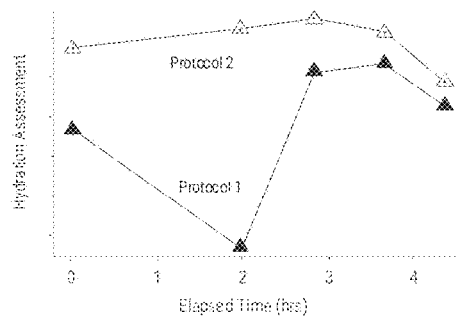

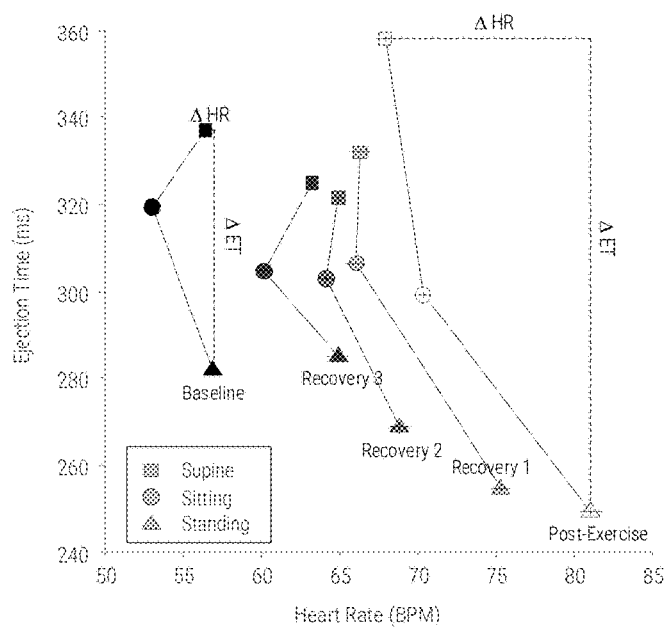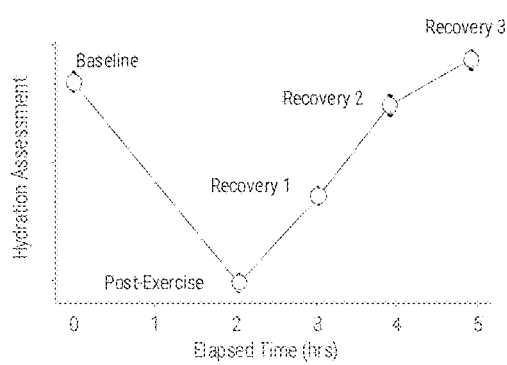
FIG. 39A
FIG. 39B

HYDRATION ASSESSMENT SYSTEM

TECHNICAL FIELD

The present invention relates to determination of an individual's hydration status, and in particular to wearable, noninvasive systems that can determine an individual's hydration status.

BACKGROUND

The determination of an individual's hydration status in a convenient fashion is a desired objective for athletes, general consumers, and elderly individuals.

As reviewed by Jéquier and Constant (2010), water is a vital constituent of the human body, and sufficient hydration is critical to overall physiological performance due to the impact of vascular volume on cognitive function, kidney function and cardiovascular function. Jéquier, E., & Constant, F. (2010). Water as an essential nutrient: the physiological basis of hydration. European journal of clinical nutrition, 64(2), 115.

Dehydration (body water deficit) is a physiologic state that can have profound implications for human health and performance. FIG. 1 displays the mental and physical effects of dehydration as a function of the percent of weight lost in water. Early effects include irritability and decrease of peak physical performance, while severe effects include coma and ultimately death. Unfortunately, dehydration can be difficult to assess and there is no universal gold standard. As illustrated in FIG. 2, roughly 60% of the human body is composed of water, which is contained in different intracellular and extracellular compartments. The complexity of hydration measurement arises, in part, from the ubiquitous presence of water in multiple body compartments, and the continuous homeostatic flux between compartments. Armstrong (2007) speaks to the complexity of (1) accurately defining hydration due to the multiple water compartments and (2) the measurement difficulties of any individual compartment. Armstrong, L. E. (2007). Assessing hydration status: the elusive gold standard. Journal of the American College of Nutrition, 26, 575S-584S.

Through the activities of daily living, an individual creates a "daily water deficit", i.e., the amount of water that a person needs to consume to compensate for loss due to sweat, urine, and respiration, etc. Depending on individual size and activity level, daily water deficit varies from ~1 to 6 L. This deficit must be replenished, largely through oral intake. Armstrong, Lawrence E. "Assessing hydration status: the elusive gold standard." Journal of the American College of Nutrition 26. sup5 (2007): 575S-584S.

The large degree of variance in daily water requirements limits the use of standard tables or "rules of thumb" to guide oral replenishment. Perspiration rate, in particular, varies significantly between individuals and within individuals, and depends on factors including base physiology, activity intensity, environmental temperature and humidity, and the amount and type of clothing or equipment worn. Thus, the same individual can have strikingly different sweat rates and overall water loss for the same activity on different days.

Our innate mechanism for guiding rehydration, the "drink to thirst" mechanism, is typically effective under conditions with limited physiological perturbations or challenges. However, under conditions of physiological stress, the "drink to thirst" response has been shown to ineffective. A recent paper in Medicine & Science in Sports & Exercise by Stavros Kavouras at the University of Arkansas showed that endurance cyclists experienced performance declines when hydrating by thirst instead of following a predetermined hydration schedule. Adams, J. D., et al. "Dehydration Impairs Cycling Performance, Independently of Thirst: A Blinded Study." Medicine and science in sports and exercise 50.8 (2018): 1697-1703.

U.S. Army researcher Robert Kenefick, who wrote that: "planned drinking is optimal in longer duration activities of greater than 90 minutes, particularly in the heat; higher-intensity exercise with high sweat rates; exercise where performance is a concern; and when carbohydrate intake of 1 gram/minute is desired." He also pointed to 60-90 minute timeframes as a subjective gray zone, with no clear evidence in favor of hydration by thirst, or by schedule, (Kenefick, Robert W. "Drinking strategies: planned drinking versus drinking to thirst." Sports Medicine 48.1 (2018): 31-37.).

Sufficient hydration is critical for optimal physical performance because dehydration directly affects the volume of extracellular fluid within the vascular space, known as the plasma volume. Reductions in plasma volume decrease the amount of blood entering the heart during diastole, the phase in the cardiac cycle where the heart relaxes and fills with blood. Less blood entering the heart during diastole decreases end diastolic volume and thus the amount of blood leaving the heart during systole, the phase where the heart contracts. The result is a decreased stroke volume, cardiac output, and maximal aerobic power (VO2 max).

Current hydration assessment techniques include (1) total body water as measured by isotope dilution or estimated by bioelectrical impedance analysis, (2) plasma markers, such as osmolality, sodium, hematocrit and hemoglobin changes, or the concentrations of hormones that help regulate body fluids, (3) urine markers, such as osmolality, specific gravity, or color, and (4) observable physical signs, such as salivary flow or gross, physical signs and symptoms of clinical dehydration. The majority of these methods require clinical equipment and/or expertise and are far from convenient.

Thus, the ability to conveniently access overall hydration status at multiple points throughout the day has significant value, particularly for individuals undergoing physiological stress who cannot rely on their thirst mechanism to guide rehydration.

U.S. Pat. No. 5,964,701 to Asada et al., entitled "Patient Monitoring Finger Ring Sensor", discloses a health status monitor incorporated into a finger ring, comprising sensors that may include a thermocouple for measuring skin temperature, an electrical impedance plethysmograph, and one or more optical sensors for pulse rate and measurements of blood constituent concentration and blood flow. U.S. Pat. No. 6,402,690 B1 to Rhee et al., entitled "Isolating Ring Sensor Design", discloses a heath monitoring system for a patient by performing measurements such as skin temperature, blood flow, blood constituent concentration, and pulse rate at the finger of the patient. The monitoring system has an inner ring proximate to the finger as well as an outer ring, mechanically decoupled from the inner ring, that shields the inner ring from external loads. US Patent application publication 2016/0166161 A1 by Yang et al., entitled "Novel Design Considerations in the Development of a Photoplethysmography Ring" discloses a wearable health monitoring apparatus comprising a light source and a detector configured to receive transmitted and/or reflected light from a tissue sample, wherein the source and/or detector are incorporated into protrusions located within a ring-like structure. US Patent application 2017/0042477 A1 by Haverinen et al., entitled "Wearable electronic device and method for manufacturing thereof", discloses a wearable electronic device which may be worn on the finger, operable to measure different physiological parameters, such as blood volume pulse, to determine a heart rate of the user. U.S. Pat. No. 10,281,953 B2 to von Badinski et al., entitled "Wearable Computing Device and Transmission Method" discloses a wearable computing device configured as a ring for being worn around the finger of a user, comprising sensor modules that enable the device to perform multiple functions to include a heart rate sensor and pulse oximetry. US Patent application publication 2016/0066827 A1 by Workman and Bomsta, entitled "Pulse Oximetry Ring", discloses a wearable finger can provide a variety of biometrics (including heart rate, blood oxygen level, and skin temperature) and health measures (e.g., fall detection, sleep pattern recognition, and movement tracking). US Patent application 2010/0298677 A1 by Lu et al., entitled "Wireless ring-type physical detector", discloses a ring-type physical detector that uses a light signal to detect the blood oxygen saturation, the heartbeat and continuous blood pressure. Lu et al. also teach that the ring further comprises an adjusting belt for changing the inner diameter of the ring. US Patent application publication 2020/0085360 A1 by Yuan and Zhou, entitled "Ring-type pulse oximeter", discloses a ring-type pulse oximeter, comprising, in part, an elastic device, a photodiode, and at least one light emitting diode that are protrudingly disposed on an inner circumferential surface of ring body. When the ring is worn, the elastic device is pressed so that the photodiode and at least one light emitting diode fit with a finger, and light emitted by the light emitting diode is attenuated by the finger, then received by the photodiode and processed to calculate blood oxygen saturation. The ring-type pulse oximeter exerts a force on a portion of the finger, such that the finger maintains a tight fit to the photodiode and the light-emitting diode, thereby providing a comfortable wearing experience as well as adaptability to different finger shapes, and improving measurement accuracy.

U.S. Pat. No. 9,711,060 B1 to Lusted et al., entitled "Biometric sensor ring for continuous wear mobile data applications" discloses a biometric sensing ring worn on the finger for estimating the emotional state of a user. The ring is configured with a plurality of sensors for sensing electrodermal activity (EDA), photoplethysmograph (PPG), temperature, and acceleration. The invention derives emotion metrics from the data collected by the biometric sensing ring, which includes heart rate (HR), heart rate variability (HRV), and respiration rate based on HRV. The ring is configured for creating variable ring geometry to accommodate different sized fingers while offering comfortable fit for the user. Lusted et al., teach the sensors must be in stable contact with the skin in order to acquire optical EDA and PPG data.

As evidenced by the above review of relevant prior art, there has been significant innovation in determining various physiological parameters with wearable devices, in particular finger rings. However, the above prior art does not disclose the determination of hydration based on aortic valve opening and closing with a wearable device.

SUMMARY OF INVENTION

Some embodiments of the present invention provide an apparatus for determining the hydration status of a user, comprising: (a) a ring, having an internal surface with an effective internal diameter, configured to be worn around a finger of the user; (b) an optical sensor system comprising (i) one or more optical emitters mounted with the ring such that light emitted by the one or more emitters is directed toward the finger and (ii) one or more detectors mounted with the ring such that the one or more detectors produce a detector signal representative of light reaching the detectors from one or more emitters after the light has interacted with tissue of the finger, configured to detect physiological signals indicative of opening and closing of the user's aortic valve; (c) a trigger system, configured to detect an event indicating a hydration measurement is to be initiated; (d) an optical sampling control system responsive to the trigger system configured to operate the one or more emitters and the one or more detectors at a first set of operational parameters; e) an analysis system responsive to the detector signal and configured to determine an interbeat time interval between successive openings of the user's aortic valve, and an ejection time interval between opening and closing of the user's aortic valve; (f) a hydration determination system configured to determine the hydration status of the user from the interbeat time interval and the ejection time interval; (g) a feedback system configured to provide feedback. Some embodiments further comprise a user input system configured to receive input from the user, and wherein the hydration determination system is configured to determine the hydration status of the user from the interbeat time interval and the ejection time interval and from the input. Some embodiments further comprise a posture determination system configured to determine the user's posture responsive to optical sensor system, the user input system, or a combination thereof, and wherein the hydration determination system is configured to determine the hydration status from the interbeat time interval, the ejection time interval, and the user's posture at the time the detector signal is produced. In some embodiments, the hydration determination system is configured to determine the hydration status from the interbeat time interval and the ejection time interval at a first posture, and from the interbeat time interval and the ejection time interval at a second posture.

In some embodiments, the analysis system is further configured to determine the suitability of the detector signal for hydration determination. Some embodiments further comprise a motion sensor system, and wherein the analysis is configured to determine the suitability of the detector signal responsive to the motion sensor system. In some embodiments, the optical sampling control system is configured to change the operational parameters responsive to the suitability of the detector signal determined by the analysis system. In some embodiments, the ring is configurable to assume a plurality of effective internal diameters such that, when the ring is configured to a first effective internal diameter, the venous transmural pressure in the tissue of the finger that has interacted with the light is less than zero and the arterial transmural pressure at diastole in the tissue of the finger that has interacted with the light is greater than zero. In some embodiments, the ring is configurable to assume a plurality of effective internal diameters such that the ring can be configured to a first effective internal diameter, producing a first set of transmural pressures in blood vessels in the tissue of the finger, and to a second effective internal diameter, producing a second set of transmural pressures in the blood vessels, where the pressures in the second set of transmural pressures are smaller than the pressures in the first set of transmural pressures. In some embodiments, the ring is configurable to either of two stable states wherein the first stable state the ring has a first effective internal diameter, and wherein the second stable state the ring has a second effective internal diameter distinct from the first effective internal diameter. In some embodiments, the ring has a mechanical bias that encourages the ring to the second stable state. In some embodiments, the second effective internal diameter is less than the first effective internal diameter.

In some embodiments, the trigger system comprises a sensor sensitive to a change in the effective internal diameter of the ring. In some embodiments, the trigger system is responsive to the optical sensor system, the user input system, or a combination thereof. Some embodiments further comprise a motion sensor system comprising an accelerometer, a gyroscope, or a combination thereof; and wherein the trigger system is responsive to the motion sensor system. In some embodiments, the ring comprises one of more compressive features that protrude from the inner surface of the ring, and wherein the effective internal diameter can be altered by the movement of the one of more compressive features. In some embodiments, the ring comprises one or more ring features, and wherein the effective internal diameter can be altered by movement of the one or more ring features along the longitudinal axis. In some embodiments, the ring has a reducible internal circumference. In some embodiments, the ring has ring features comprising protuberances on the inside of the ring whose configurations can be changed between first and second configurations, wherein the ring has a first effective internal diameter when the protuberances are at the first configuration and a second effective internal diameter, different from the first effective internal diameter, when the protuberances are at the second configuration.

In some embodiments, the user feedback system comprises one or more LEDs or haptic sensors mounted with the ring. In some embodiments, the user feedback system comprises an external device in communication with the ring, wherein the external device comprises a visible display. In some embodiments, the one or more optical emitters and the one or more detectors are mounted with the ring such that light reaching the detector comprises a majority of photons that have traveled through the tissue and interacted with tri-layered vessels. In some embodiments, an angle between an emitter and a detector, measured from the center of the ring, is greater than 15 degrees.

Some embodiments provide a method of determining the hydration status of a user, comprising: (a) providing a ring configured for wearing around a finger of the user wherein the ring comprises one or more optical emitters mounted with the ring such that light emitted by the one or more emitters is directed toward the finger, and one or more detectors mounted with the ring such that the one or more detectors produce a signal representative of light reaching the one or more detectors from one or more emitters after the light has interacted with tissue of the finger; (b) triggering a hydration measurement by one or more of a user-based, time-based, or signal-based event; and then (c) operating the one or more emitters and the one or more detectors using a first set of operational parameters and acquiring a signal from the detector representative of light interaction with a sampling region of the finger; d) determining from the detector signal the interbeat time interval between successive openings of the user's aortic valve and the ejection time interval between opening and closing of the user's aortic valve; (e) determining the hydration status of the user from the interbeat time interval and the ejection time interval. Some embodiments further comprise prior to step (c) establishing a first set of transmural pressures in the blood vessels in the sampling region, such that the venous transmural pressure in the sampling region is less than zero and the arterial transmural pressure at diastole in the sampling region is greater than zero.

Some embodiments further comprise determining a metric indicative of the suitability of the detector signal for determining hydration status. Some embodiments further comprise g determining if the metric is within predetermined bounds, and, if not, repeating step (c) using a second set of operational parameters, different from the first, before performing step (d). Some embodiments further comprise determining if the metric is within predetermined bounds, and, if not, establishing a second transmural pressure, different from the first transmural pressure, and repeating step (c) before performing step (d). Some embodiments further comprise determining if the metric is within predetermined bounds, and, if not, establishing a second transmural pressure, different from the first transmural pressure, and repeating step (c) using a second set of operating parameters, different from the first, before performing step (d).

In some embodiments, step (c) is repeated a plurality of times, each time using a different set of operational parameters and together producing a plurality of detector signals, and wherein step (d) comprises determining the hydration status from the plurality of detector signals. In some embodiments, step (c) is repeated a plurality of times, each time using a different set of operational parameters and together producing a plurality of detector signals, and further comprising determining a metric indicative of the suitability of the detector signal for determining hydration status for each of the detector signals; and wherein step (d) comprises determining the hydration status from the plurality of detector signals weighted by the metric for each of the plurality of detector signals. In some embodiments, detector signals corresponding to a metric outside a predetermined range are weighted at zero in step (d). In some embodiments, step (c) is performed while the user is in a first posture to produce a first detector signal and while the user is in a second posture to produce a second detector signal; and wherein step (d) comprises determining the hydration status from first and second detector signals.

In some embodiments, the ring has an adjustable effective internal diameter, and wherein establishing a transmural pressure comprises establishing the effective internal diameter of the ring. In some embodiments, establishing a transmural pressure comprises positioning the hand on which the ring is worn to a predetermined elevation relative to the heart. In some embodiments, establishing a transmural pressure comprises moving the ring to a different finger region. In some embodiments, establishing a transmural pressure comprises pushing a portion of the ring toward the finger. In some embodiments, step (e) comprises determining the hydration status of the user from the interbeat time interval and the ejection time interval and the user's posture when the detector signal was produced.

Some embodiments further comprise determining the posture of the user from one or more of an accelerometer mounted with the ring, a gyroscope mounted with the ring, or optical sensors mounted with the ring. Some embodiments further comprise accepting from the user an indication of the user's posture.

In some embodiments, step (e) comprises determining the hydration status of the user from the interbeat time interval and the ejection time interval and one or more of the user's age, gender, weight, or height at the time the detector signal was produced. In some embodiments, step (c) is performed two times, the first time using operational parameters that establish a transmission dominant sampling, and the second time using operational parameters that establish a reflectance dominant sampling; and determining which detector signal has the strongest aortic closure signal, and using that detector signal in step (d). Some embodiments further comprise displaying the hydration status on a device separate from and in communication with the ring. Some embodiments further comprise providing visual, aural, or haptic feedback to the user using the ring. Some embodiments further comprise providing a plurality of rings distinct in appearance from each other, and providing feedback to the user if a battery powering a first ring is low, such that the user can use a second ring.

Some embodiments provide a method for determining the hydration status of a user, comprising: (a) acquiring a signal from a wearable sensor nonobtrusive to the activities of daily life, configured to detect changes in blood volume in a measurement region of the user, which changes are indicative of opening and closing of the user's aortic valve, while the user is in one or more distinct postures; (b) using a hydration determination model to determine the hydration status of the user from the signal determined at one or more postures; (c) communicating the hydration status to the user.

In some embodiments, step (a) further comprises determining the posture and the maintenance of the posture by the user during the acquisition of the signal. In some embodiments, step (b) comprises (b1) determining an interbeat time interval between successive aortic valve openings; (b2) determining an ejection time interval between aortic valve opening and aortic valve closing; and (b3) determining the hydration status from the interbeat time interval, and the ejection time interval determined at one or more postures. In some embodiments, step (b) comprises (b1) determining an interbeat time interval between successive aortic valve openings; (b2) determining an ejection time interval between aortic valve opening and aortic valve closing; and (b3) determining the hydration status from the interbeat time interval, the ejection time interval, and the posture determined at one or more postures. In some embodiments, the sensor is worn around a finger, wrist or upper arm of the user. Some embodiments further comprise establishing a transmural pressure in the blood vessels contained in measurement region, such that the transmural pressure in veins in the region is less than zero and the transmural pressure in arteries in the region at diastole is greater than zero.

BRIEF DESCRIPTION OF DRAWINGS

FIG. 3 is an error sensitivity comparison table for different approaches to hydration assessment.

FIG. 8 shows example measurement locations of the invention.

FIG. 23 shows example mechanisms to change the effective internal diameter of a ring.

FIG. 26 shows example mechanisms to change the effective internal diameter of a ring.

FIG. 27 shows example mechanisms to change the effective internal diameter of a ring.

FIG. 28 shows example mechanisms to change the effective internal diameter of a ring.

FIG. 30 shows example mechanisms to change the effective internal diameter of a ring.

FIG. 35 illustrates measurement results during exercise with and without fluid replenishment.

FIG. 39 shows measurement results using positional changes in the hydration assessment.

INDUSTRIAL APPLICABILITY AND MODES OF CARRYING OUT THE INVENTION

Figure 1:
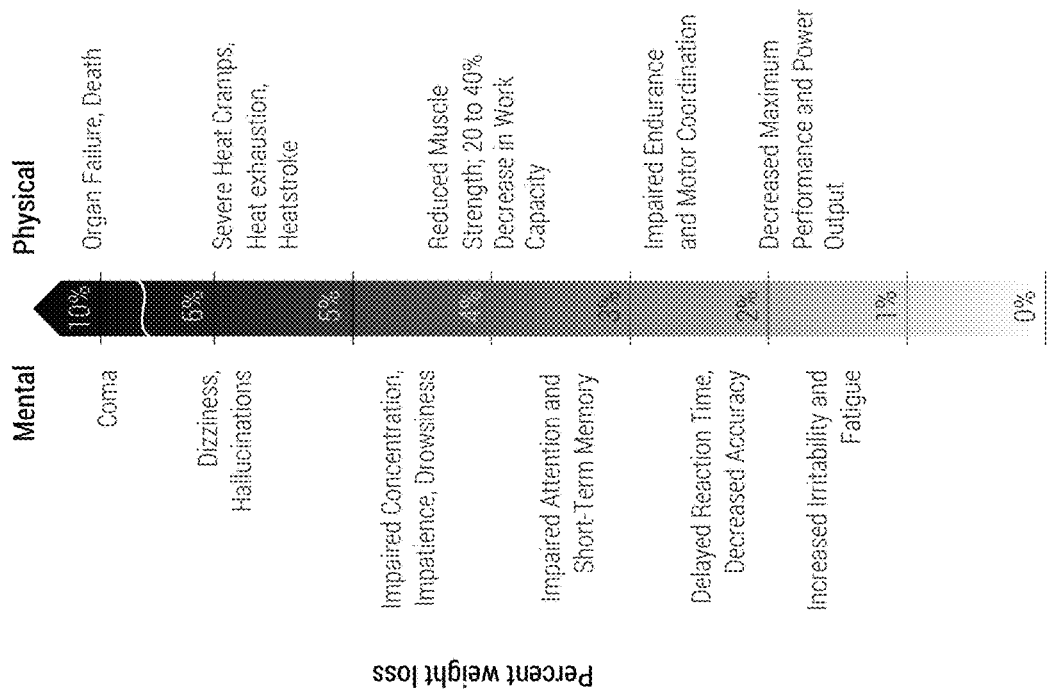
FIG. 1 illustrates the effects mental and physical effects of dehydration.
Figure 2:
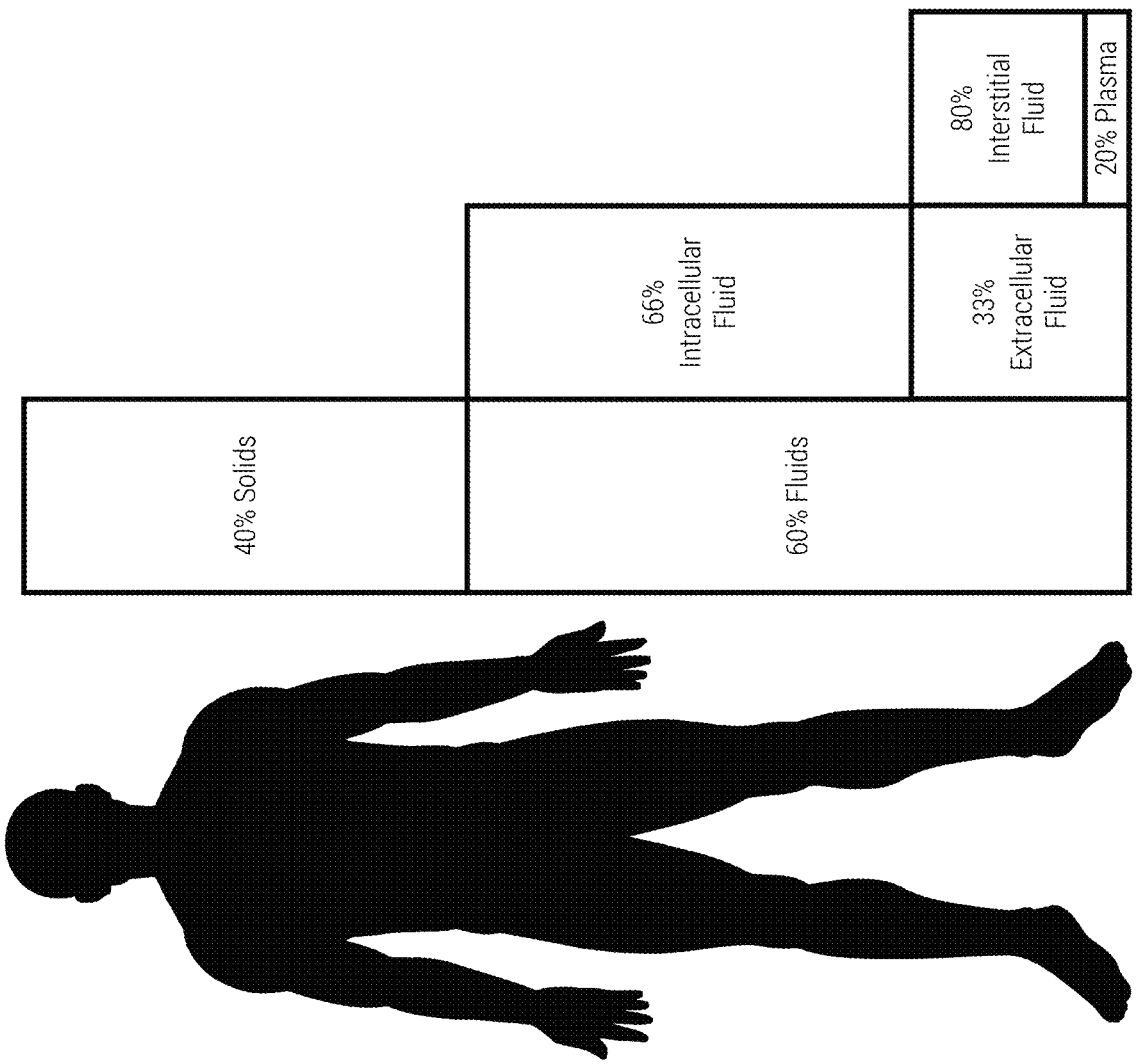
FIG. 2 presents the different water compartments in the human body.

Definitions. For the purposes of this invention, hydration or dehydration are defined broadly as a measure of the amount of water present in the body. Changes in hydration status occur when water intake is inconsistent with changes in free water lost due to normal physiologic processes, including breathing, urination, and perspiration, or other causes, including diarrhea and vomiting. Total body water (TBH2O) represents about 45-60% of body weight depending on age, gender, and race. TBH2O is further divided into an intracellular fluid compartment (ICF; about 60% of total body water) and an extracellular fluid compartment (ECF; about 40% of total body water), which are proportional to the ratio of osmotically-active intracellular K+ to extracellular Na+. During normal physiology these compartments are dynamically equilibrating to maintain whole-body fluid balance.

For the purposes of this invention, dehydration includes hypertonic, isotonic, and hypotonic dehydration. Hypertonic dehydration occurs when more water is lost from the body than salt, increasing blood osmolality. Increased sweat rate is a common cause of hypertonic dehydration. Isotonic or hypotonic dehydration occur when the amount of water lost is equal to or less than the amount of salt lost, respectively. Isotonic dehydration is commonly caused by diarrhea or blood loss.

As used herein, effective circulating volume, vascular volume, and blood volume are interchangeable terms. The effective circulating volume refers to that part of the extracellular fluid compartment that is within the vascular space and is effectively perfusing the tissues. Circulating volume refers to the total amount of fluid circulating within the arteries, capillaries, veins, venules, and chambers of the heart at a given time that is available to the heart for pumping.

As used herein, the time course of aortic value opening and closing refers to any data representation that contains the relationship between the status of the aortic value and some measurement of time.

As used herein, the ejection time (ET) is the time interval between the aortic valve opening (AVO) and the aortic valve closure (AVC). Blood is ejected from the left ventricle during this interval.

As used herein, the interbeat interval (IBI) refers to the time interval between similar points in the cardiac cycle. For example, the IBI can be defined as the time between aortic valve openings (AVOs) in successive cycles.

As used herein, the terms "body posture", "body position", or "body pose" refer to the different physical configurations that the human body can assume. The most common body postures include supine (lying on the back), seated, and standing positions.

As used herein, "positional changes", "posture changes", or "changes in pose" are terms that refer to any process that alters body position in a manner that changes the venous return to the heart. For example, one simple way to manipulate venous return via positional changes is to move between supine, seated, and standing positions.

The term "determination model" as used herein is broadly defined as any process that takes defined inputs and applies calculations or a designated set of steps to determine a desired output. Determination models include many classes of models but can be broadly broken into "prediction models" and "matching models". Prediction models are constructed by determining the relationship between data or data features and desired output; once the relationship is determined the model can be applied to novel data with no reliance on the training or reference data. These models are distinct from matching models which rely on pre-existing library of training or reference data. A matching model determines the proximity of novel data to reference data to produce the desired output. Examples of prediction models include regression models, where features are mapped to outputs through linear or non-linear relationships, as well as some machine learning models, in which more complex data representations are mapped to the desired output. In these approaches, often referred to as "deep learning models", the useful features and representations are essentially learned by the model in training, along with the function that maps the inputs to the desired outputs. Because the relationship between input and outputs is often quite complex (involving thousands of weights in multiple hierarchical layers) the engineer or architect of the model might be completely unaware of the features or information that the model has extracted, or how and why that information is combined to form the output. In some embodiments of this invention, the determination model can use as inputs features extracted from a data representation that contains the relationship between the status of the aortic value and some measurement of time. In other embodiments, the determination model can use as inputs a raw or conditioned data representation that contains the relationship between the status of the aortic value and some measurement of time. A determination model can also include additional inputs, such as body position or information about the user. The output of a given determination model is the desired parameter, such as hydration status.

Transmural pressure is a general term that describes the pressure across the wall of a vessel (transmural literally means "across the wall"). A flexible container expands if there is a positive transmural pressure (pressure greater inside than outside the object) and contracts with a negative transmural pressure. A positive transmural pressure is sometimes referred to as a "distending" pressure.

As used herein, photoplethysmography (PPG) is an optical measurement technique that can be used to detect blood volume changes in tissue or has a signal that is related to the cardiac cycle and contains aortic value opening and closure information.

The term "signal" as used herein includes any means of transmitting information such as a measurement, including without limitation an analog electrical waveform or digital representation thereof, e.g., that which is collected or transmitted by a biological or physiological sensor, such as a PPG.

The term "noninvasive" refers to a method or apparatus that does not create a break in the skin and makes no contact with an internal body cavity beyond a natural body orifice. PPG and EKG sensors are examples of noninvasive sensors that can make measurements without breaking the skin. Likewise, PPG is an example of noninvasive sampling, wherein measurements are acquired optically from the skin surface without introducing instruments into the body.

As used herein, a high-fidelity signal is a measured signal that faithfully reflects the underlying true signal, with little distortion or noise.

As used herein, the term "emitter" describes any device emitting electromagnetic radiation. One example of an emitter is a light emitting diode (LED).

The terms "photodetector", "optical detector", or simply "detector", refer to any device that detects or responds to incident light by using the electrical effect of individual photons.

As used herein, the term "tri-layered vessels" refers to blood vessels comprised of three layers: the tunica intima, the tunica media, and the tunica adventitia. Tri-layered vessels include arteries, arterioles, venules, and veins, but do not include capillaries, which are comprised of a single layer of endothelial cells.

Transmission dominant sampling refers to optical sampling of the tissue where the majority of photons penetrate and travel through the tissue, interacting with (i.e., reflected by, scattered by, or absorbed by) tri-layered vessels.

Reflection dominant sampling refers to optical sampling of the tissue where the majority of photons do not penetrate deeply into the tissue and primarily interact with (i.e., are reflected by, scattered by, or absorbed by) vessels in the capillary bed.

As used herein, the term "deformable" broadly describes an object that changes its shape or volume while being acted upon by an external force. The process of deformation can occur within a single deformable component, for example, one with elastic material properties that may stretch or bend, or through the respective movement of rigid components, as seen in, for example, telescopic expansion and hinges.

As used herein, "user-based" or "user-initiated" events or triggers broadly refer to a process in which a hydration determination is performed responsive to an action of the user. The user action may include, but is not limited to, a gesture, specified motion, application of force, button press, vocal expression, or communication through a connected device representing a volitional choice on the part of the user to obtain a hydration assessment.

As used herein, the terms "activities of daily life" or "activities of daily living" refer to the routine activities people do every day in normal life. Minimally, these activities include eating, bathing, getting dressed, using the toilet, and getting in and out of bed.

As used herein, the "effective internal diameter" of a ring is defined as the diameter of the largest possible circle that can be inscribed in the ring when viewed as a longitudinal projection.

For the purposes of this invention, the "sampling" is defined as the acquisition of physiological data from a user. The related terms, "sampling site", "sampling region", and "sampling location", refer to a region of a user where sampling is performed. When physiological data are acquired using an optical system, these terms refer to the region where light interacts with the tissue.

As used herein, the terms "operational parameters" refers to all acquisition parameters of an established optical system that can be configured at the time of sampling, including any or all of: the sample rate, set of active emitters, wavelength(s) emitted, LED drive current, set of active detectors, detector integration time, sample averaging, presence or absence of ambient light cancellation, and range of analog-to-digital conversion.

Approaches to Wearable Hydration Determination

Conventional Approaches. Multiple groups have sought to create hydration measurement systems that are noninvasive and wearable. The majority of prior attempts have sought to measure the concentration of water within the skin or blood, and typically fall into one of the following approaches: (1) spectroscopic determination of constituent concentrations in the blood or tissue, (2) impedance-based determination of body water content, (3) pulse size or perfusion analysis, or (4) chemometric-based assessment of sweat. These methods and their challenges are discussed briefly.

Absorbance spectroscopy refers broadly to spectroscopic techniques that measure the absorption of radiation, as a function of frequency or wavelength, due to its interaction with a sample. Absorption spectroscopy is employed as an analytical chemistry tool to determine the presence of a substance in a sample and, in many cases, to quantify the amount of the substance present. In practice, absorbance measurements are challenging to implement due to instrumentation drift, the use of multiple wavelengths, instrument drift, pathlength differences, and tissue sampling errors. The degree of absorbance is determined by the light interaction with all materials located between the source and detector. The water content in the sweat on the surface of the skin absorbs at the same level as the same amount of water located in the skin, producing a significant error in methods relying on absorption. Additionally, changes in the physical relationship or interface between the tissue and the optical measurement system that change the measured absorbance represent problematic error sources. Such changes can easily occur during typical movement of the body. Absorbance measurements are highly sensitive to changes in the tissue-optical instrument interface, and skin surface contamination (e.g., by sweat or other substances).

US Patent application publication 2020/0000345 A1 by Connor, entitled "Wearable Ring of Optical Biometric Sensors", is an example of an invention that tries to address the technological challenges of spectroscopic measurements of biometric parameters, to include hydration. Connor describes a wearable ring of sensors comprising an arcuate array of light emitters and receivers configured to collectively span at least half of the circumference of the finger, wrist or arm wearing the ring. The location, emission angle, distance, and pressure of the emitters can be adjusted such that the emitters remain in close optical communication with the surface of the finger, wrist, or arm even if the device shifts and/or rotates.

Spectroscopic assessment of hydration based on optically-determined hemoconcentration has also been proposed. The concept is based on the fact that as hydration changes, the number of red blood cells in the vascular system will remain roughly constant but the volume of fluid in the vascular compartment decreases. The result is mild hemoconcentration that occurs with dehydration. Most efforts have pursued analytical methods that isolate the signal to the arterial pulse. US Patent application publication 2015/0148623 A1 by Benaron, entitled "Hydration Monitoring Sensor and Method for Cell Phones, Smart Watches, Occupancy Sensors, and Wearables", is an example of an invention for hydration monitoring with wearables and other devices that uses a spectroscopic approach. Benaron discloses estimating hydration by determining a measure of water content, said measure of water content at least in part based on a function of a concentration of components of the bloodstream or tissue of the subject over time determined using spectral analysis of the detected light.

Bioelectrical impedance analysis (BIA) is a commonly used method for estimating body composition, in particular body fat and muscle mass. In BIA, a weak electric current flows through the body and the voltage is measured in order to calculate (resistance) of the body. BIA determines the electrical impedance, or opposition to the flow of an electric current, through body tissues which can then be used to estimate total body water (TBW), which can be used to estimate fat-free body mass and, by difference with body weight, body fat. Dehydration is a recognized factor affecting BIA measurements because it causes an increase in the body's electrical resistance. Thus, under the assumption of constant muscle mass, BIA can be used to determine a change in hydration, expressed as total body water. In a typical use-case the measurement process requires that four electrodes be attached to the body, typically attached to hands and feet. BIA is capable of estimating total body water with good accuracy in healthy subjects. However, the biophysical principles of BIA limits accuracy and applicability for hydration assessment. This is well described by O'Brien et al., who write, "while BIA can reliably estimate total body water and body density in euhydrated individuals under standardized clinical conditions, changes in fluid and electrolyte content can independently alter bioimpedance measurements. Because hydration changes typically involve concomitant changes in fluid and electrolyte content, the interpretation of a change in bioimpedance will often be confounded." O'Brien, C., Young, A. J., & Sawka, M. N. (2002). Bioelectrical impedance to estimate changes in hydration status. International Journal of Sports Medicine, 23(05), 361-366. Thus, because BIA is dependent on both water and electrolyte concentrations, the type of hydration (e.g., isotonic or hypertonic) will have a significant impact on the assessment of hydration.

US Patent application publication 2016/0338639 A1 by Myers et al., entitled "Personal Hydration Monitor", is an example of an invention for a hydration sensor in a wearable device based upon impedance. Myers et al. disclose a wearable hydration monitor comprising a flexible electrode on a flexible substrate configured to measure the level of hydration of an individual using a skin impedance measurement obtained by the electrode. US Patent application publication 2015/0182164 A1 by Utter, entitled "Wearable Ring for Sleep Monitoring", is a second example of an invention of that proposes to use bioimpedance and other variety of other sensors to detect dehydration in a flexible and wearable ring. Utter discloses the potential use of a plurality of biometric sensors selected from the group consisting of a heart rate sensor, a respiration sensor, a temperature sensor, a skin conductance sensor, a skin conductance response sensor, a galvanic skin response (GSR) sensor, an electromyography (EMG) sensor, an electrodermal activity sensor, and an electrodermal response sensor.

Figure 6:
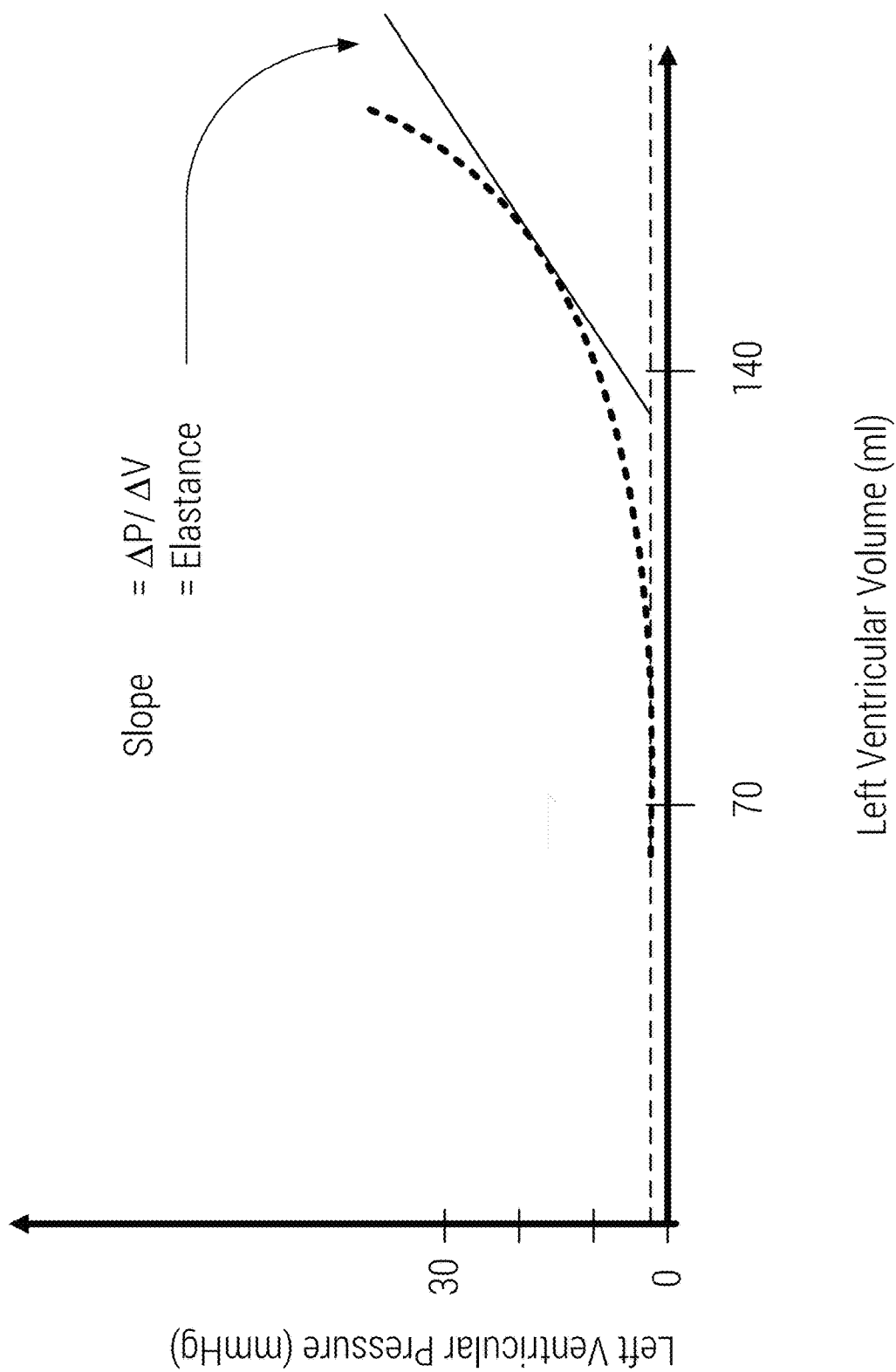
FIG. 6 demonstrates the relationship between left ventricular volume and pressure.

Other efforts have suggested using the size and shape of the pulse as a metric for hydration. Weak pulses are associated with severe dehydration. However, for the proposed purpose of maintaining or optimized physiological performance, pulse size is an inadequate approach. Pulse size, which is often parameterized as height, width, or area under the curve (AUC), is influenced by vasodilation of the peripheral vasculature as well as hydrostatic pressure. Variation in body temperature, or even temperature at the local site of the sensor, will strongly affect pulse size due to changes in arterial tone. Additionally, a simple arm raise will dramatically alter both the size and shape of the pulse. Hickey et al has quantified the type and magnitude of change as illustrated in FIG. 6 of their publication examining the impact of arm raise on PPG signals, Hickey, M., J. P. Phillips, and P. A. Kyriacou. "The effect of vascular changes on the photoplethysmographic signal at different hand elevations." Physiological measurement 36.3 (2015): 425. A second paper by Hickey explicitly explored the changes of pulse shape in response to arm raises and found pronounced morphological changes. Hickey, M., Phillips, J. P., & Kyriacou, P. A. (2016). Investigation of peripheral photoplethysmographic morphology changes induced during a hand-elevation study. Journal of clinical monitoring and computing, 30(5), 727-736. Thus, pulse size measurements will be limited by vasodilation and arm position, and pulse shape measurements will be strongly affected by the relation of the measurement site relative to the heart.

Perfusion methods have also been used to assess hydration. The most common method used clinically is the capillary refill test. The capillary refill test is initiated by applying pressure to a fingernail for 5 seconds. Following pressure release, the observer examines the time needed for the color of the nail to return to normal. If it takes longer than 1 to 3 seconds, dehydration may be present. Methods based on a similar principle use frequency- or amplitude-based analysis of the PPG signal to determine a so-called "perfusion index", which assesses the strength of the arterial pulse relative to other signals (often the non-pulsatile mean or "DC" signal). Such a method is disclosed in US Patent Application 2013/0261468 A1, by Semler and Scott, entitled "Non-invasive portable dehydration diagnostic system, device and method." Similar to approaches based solely on pulse size or shape, perfusion-based methods are limited by sensitivity to the position of the sampling site relative to the heart, the local temperature of the sampling site (which alters tone) and the perfusion of the sampling site, which can be uncorrelated with overall hydration status.

Sweat-based assessments have focused on several measurements including the amount of sweat lost as well as concentration measurements in the sweat. Proposed measurements include determination of cortisol, while other use measurement methods developed for cystic fibrosis test to measure sodium levels. The use of SW[Na+] (sweat sodium concentration, mmol/l) has been studied and the review article by Villiger, et al. escribes a number of limitations including the need for a baseline measurement, influenced due to aldosterone, and sympathetic nervous system, Villiger, M., et al. "Evaluation and review of body fluids saliva, sweat and tear compared to biochemical hydration assessment markers within blood and urine." European journal of clinical nutrition 72.1 (2018): 69.

Novel Approach. The current approach is a significant departure from prior efforts largely focused on determining water concentration. Instead, the invention is based on the time course of aortic valve opening and closure. Embodiments of the current invention are intended to be used during activities of daily living. Thus, the approach can be relatively insensitive to changes in vasodilation, sampling site location relative to the heart, skin contaminants (such as sweat), and subtle changes in the tissue-sensor interface. Because the current invention is based on the detection of aortic valve opening and closing, events which are generated centrally by the heart, the conditions at the peripheral sampling site (e.g., arterial tone, precise interface with the sensor, and position relative to the heart) have relatively little or no influence. Furthermore, because the measurement approach of the current invention is equally not intrinsically affected by electrolyte concentration, it is capable of detecting both isotonic dehydration (e.g., caused by water loss in diarrhea) and hypertonic dehydration. (e.g., caused by water loss in sweat). FIG. 3 shows the sensitivity of the previously discussed conventional methods to confounds that are likely be present during typical use. Examination of the table illustrates the value of the invention in the target use environment of everyday living. The ability to determine hydration from the time course of aortic value opening and closing is unique and valuable because it solves many preexisting measurement problems and support embodiments that can be used during activities of daily living.

Figure 4:
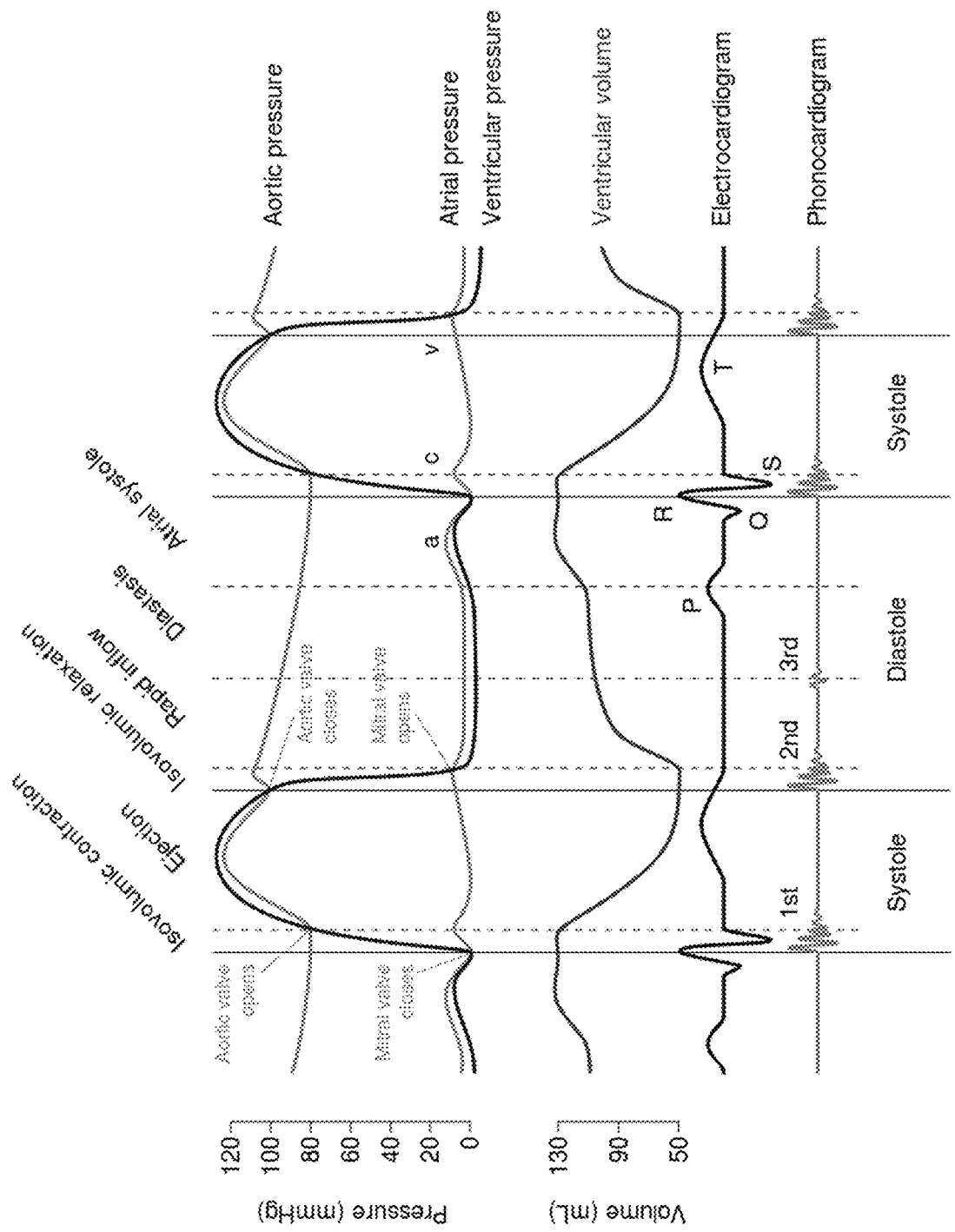
FIG. 4 shows the relationship between several measurable signals and cardiac function.

The ability to use the time course of aortic value opening and closing for the determination of hydration requires an understanding of cardiac physiology. The relationship between cardiac function and the time course of aortic valve status is illustrated in FIG. 4. The figure shows a time axis with pressure and volume relationship defined over the cardiac cycle with aortic and mitral valve function illustrated.

Figure 5:
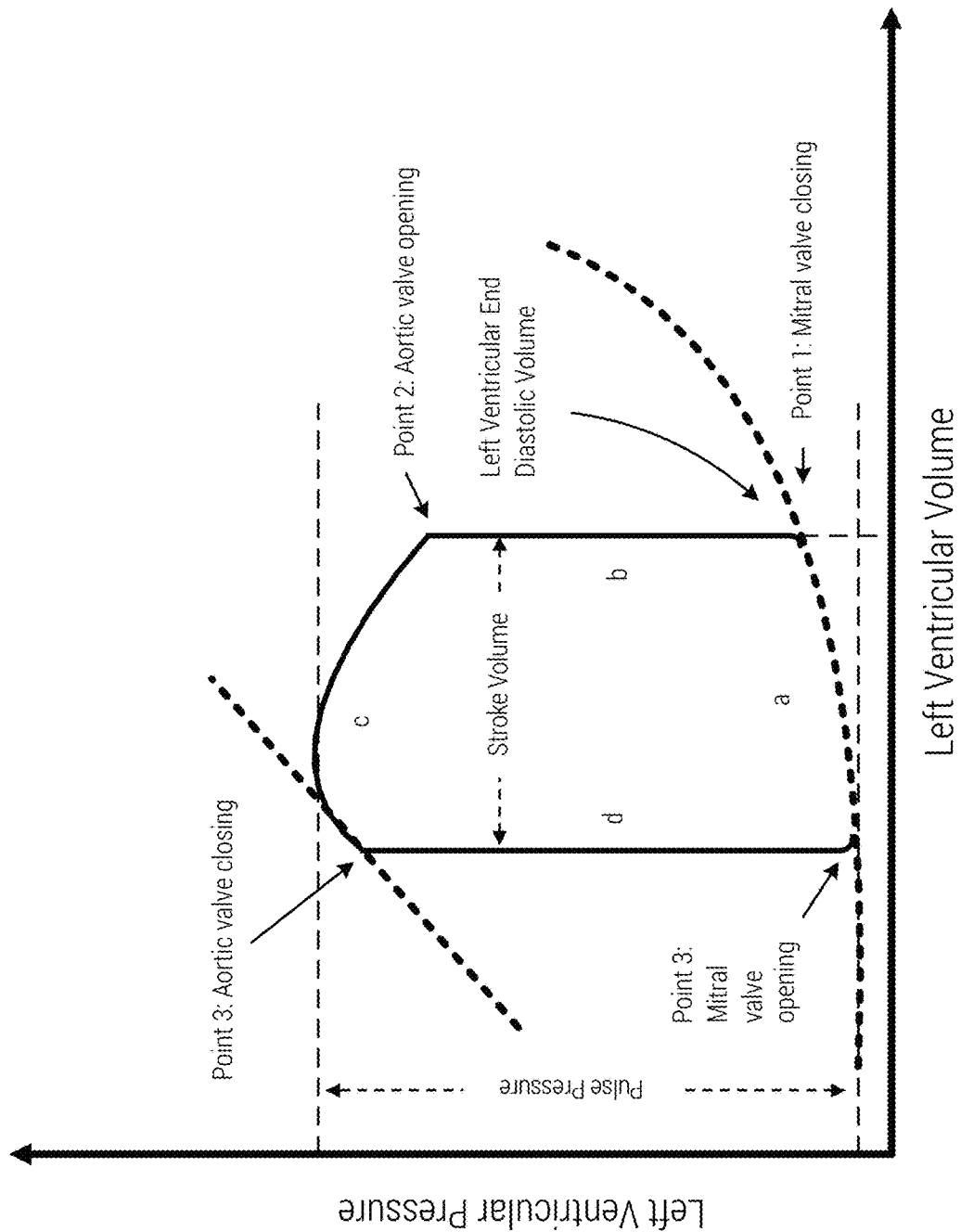
FIG. 5 represents a Sagawa pressure-volume loop.

Further axes and relationships are necessary to understand how aortic valve timing relates to hydration status. Sagawa pressure-volume loops (or "PV loops") create a relationship between pressure and volume with the aortic value status defined as critical transitions in the loop. FIG. 5 is a schematic representation of a PV loop and illustrates the relationship between filling pressure, stroke volume and aortic valve opening and closing. To generate a pressure volume loop for the left ventricle, the left ventricular pressure (LVP) is plotted against left ventricular (LV) volume at successive time points during a complete cardiac cycle. This creates a PV loop as shown in FIG. 5. A single cardiac cycle can be divided into four basic phases: ventricular filling (phase a; diastole with aortic valve closed), isovolumetric contraction (phase b, aortic value closed), ejection (phase c, aortic value open), and isovolumetric relaxation (phase d, aortic value closed). Point 1 on the PV loop is the pressure and volume at the end of ventricular filling (diastole), and therefore represents the end-diastolic pressure and end-diastolic volume (EDV) for the ventricle. As the ventricle begins to contract isovolumetrically (phase b), the LVP increases but the LV volume remains the same, resulting in a vertical line (all valves are closed). Once LVP exceeds aortic diastolic pressure, the aortic valve opens (point 2) and ejection (phase c) begins. During this phase the LV volume decreases as LVP increases to a peak value (peak systolic pressure) and then decreases as the ventricle begins to relax. When the aortic valve closes (point 3), ejection ceases and the ventricle relaxes isovolumetrically. The LV volume at this time is the end-systolic (i.e., residual) volume (ESV). When the LVP falls below left atrial pressure, the mitral valve opens (point 4) and the ventricle begins to fill. Initially, the LVP continues to fall as the ventricle fills because the ventricle is still relaxing. However, once the ventricle is fully relaxed, the LVP gradually increases as the LV volume increases. The width of the loop represents the difference between EDV and ESV, which is by definition the stroke volume (SV).

The opening of the aortic valve defines the end of diastole and the closure of the aortic valve defines the end of systole, thus the time separation of these two events is directly proportional to stroke volume.

For the purpose of quantifying hydration, the relationship between changes in hydration status and changes in the aortic valve timing must be quantifiable. The ability to quantify hydration is based on mechanical properties of the left ventricle and the resulting pressure volume relationships. At start of diastole, the blood entering the ventricle is filling the ventricle and the degree of pressure change is minimal. This period of filling can be referred to as the unstressed filling phase. The situation is like filling an empty balloon. However, as the ventricle fills further the heart begins to stretch and the pressure increases dramatically. This phase of filling can be referred to as stressed filling as the heart wall is becoming stressed. The mechanical properties of the heart are designed to prevent a burst or failure situation. The resulting pressure-volume curve has highly nonlinear relationship as shown in FIG. 6. During a condition of dehydration, the filling pressure into the heart is lower and the heart operates in the more linear region of the pressure-volume curve. The ratio of unstressed filling to stressed filling will be higher than a condition of euhydration or over-hydration.

Figure 7:
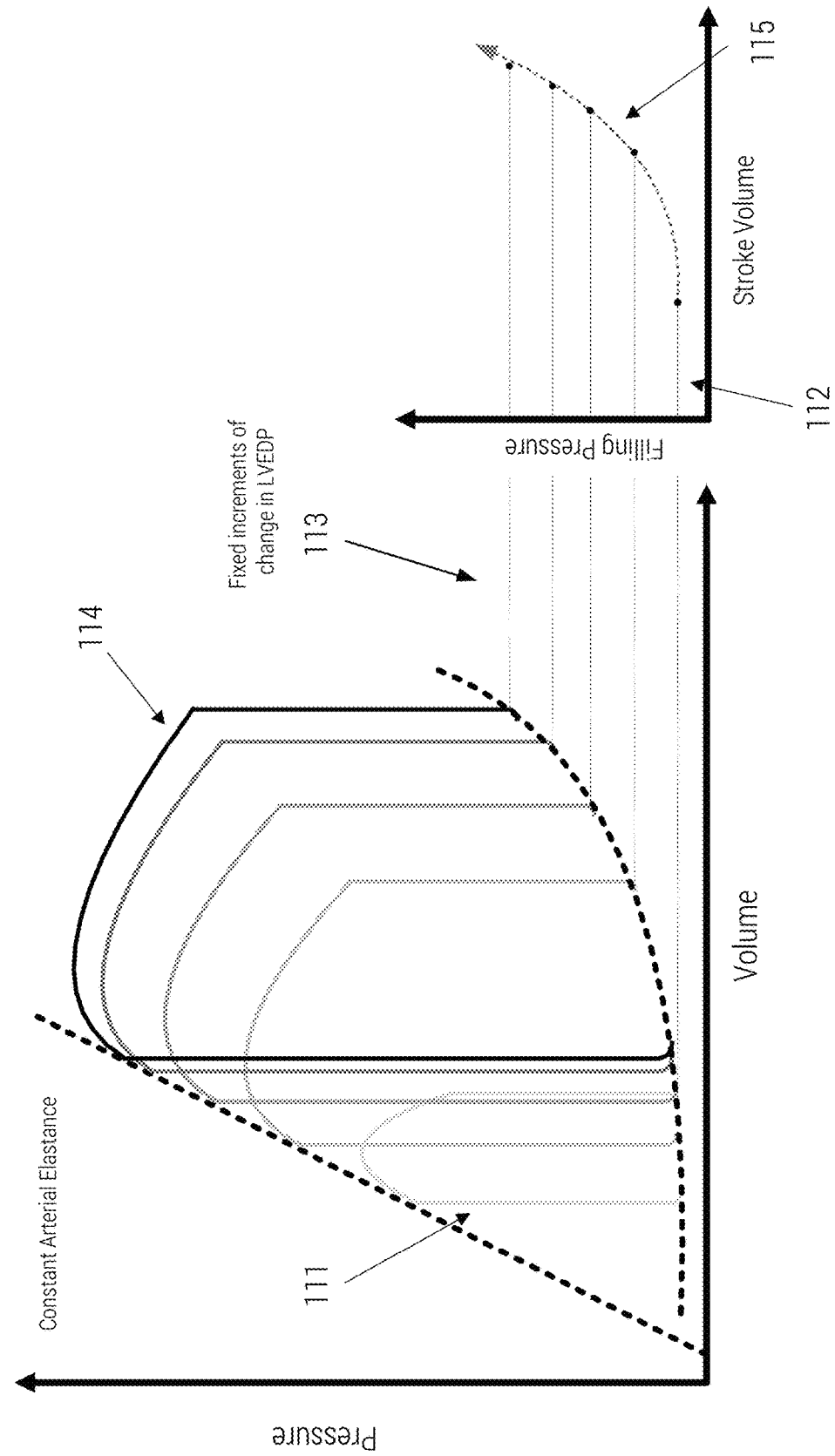
FIG. 7 illustrates pressure-volume curves under conditions of changing hydration.

FIG. 7 illustrates the impact of the unstressed to stressed filling ratio and the resulting impact on stroke volume. Pressure volume curve 111 illustrates a lower left ventricular end diastolic pressure curve with most of the filling occurring under unstressed condition as evidenced by the small change in left ventricular pressure. This curve is representative of a dehydrated state, where circulating volume has been reduced. The stroke volume associated with pressure-volume loop 111 is shown by the segment labeled 112. For illustration purposes, the left ventricular end diastolic pressure was increased in equal increments, as shown by the horizontal lines, 113. The resulting pressure volume curves of each increment in left ventricular end diastolic pressure are illustrated and the resulting stroke volume illustrated in the graph to the right of the pressure volume curves. Pressure volume curve 114 is at the highest left ventricular end diastolic pressure and corresponds to a condition of over hydration. Curve 115, shown with the dashed line is a curve connecting the end points of the various stroke volumes as defined by the above pressure-volume curves and their associated stroke volumes. The illustration clearly shows a highly nonlinear response of stroke volume with filling pressure, which can be used to determine hydration.

Thus, the ejection time, defined as the duration between the opening and the closing of the aortic valve, directly corresponds to the stroke volume defined by the separation of vertical lines b and d in FIG. 5, which can be used to assess hydration status as shown in FIG. 7.

The current invention effectively transforms changes in hydration into an observable time-based measurement that support embodiments that can be used during activities of daily living.

Determination of Aortic Valve Closure. There are several sensor technologies capable of sensing aortic valve opening and closing. However, the ability to reliably detect aortic closure in a noninvasive and wearable device presents challenges that are specifically addressed by the current invention. A brief overview of sensing technologies is provided, followed by an in-depth discussion of some innovative elements of embodiments of the present invention that facilitate reliable aortic closure determination.

In medical settings, aortic valve closure is frequently determined from a central artery pressure waveform, as measured by Doppler ultrasound or invasive catherization. The closure of the valve produces a downward notch in the aortic blood pressure, known as the incisura, due to a brief backflow of blood. The incisura is readily detected with ultrasound and catheterization, however such measurement systems are inconvenient and inconsistent with in the activities of daily living.

Optical sensors measuring changes in blood volume, commonly referred as photoplethysmography (PPG) sensors, have the potential to measure aortic valve closure and are significantly more amenable to use in wearable devices. PPG sensors can be used on various locations on the body including one or more fingers, one or more ears, one or more wrists, chest, or forehead. PPG devices can also include image-based systems with spatial resolution over one or more dimensions.

Methods such as laser Doppler flowmetry, tonometry, pulse transduction, and impedance cardiography (the measurement of electrical conductivity of the thorax), that are sensitive to changes in volume, flow, or pressure related to the cardiac cycle, can also be used to acquire signals indicative of aortic valve closure.

An alternative group of methods, sensitive to the vibrations associated with the movement of the aortic valve includes, phonocardiography, ballistocardiography, seismocardiography. Phonocardiography (PCG) is a method of detecting the sounds produced by the heart and blood flow. Similar to auscultation, PCG is most commonly measured noninvasively from the chest with a microphone. Ballistocardiography (BCG) and seismocardiography (SCG) are both methods for studying the mechanical vibrations that are produced by the cardiac cycle. BCG is a method where the cardiac reaction forces acting on the body are measured. SCG, on the other hand, is a method where the local vibrations of the precordium (the region of the thorax immediately in front of the heart) are measured.

The preceding examples do not comprise an exhaustive list of technologies that can sense physiological changes associated with opening and closing of the aortic valve, but illustrate the variety of methods that have the potential to be used in the current invention. FIG. 8 illustrates several measurement locations where such sensors can be used to create data streams containing information of aortic valve opening and closing without interfering with the activities of daily living.

The previous sensing technologies and the sensor locations in FIG. 8 may resemble wearable devices currently available and designed for other purposes, but such "off the shelf" sensors cannot be used to reliably determine aortic valve closure. As an example, numerous currently available wearable PPG systems are designed to determine heart rate or heart rate variability. This determination requires only the measurement of signals or events associated with aortic valve opening. At the PPG measurement site, aortic valve opening manifests as a rapid increase in blood volume corresponding to the arrival of the pulse. Conventional wearable PPG heart rate monitors often use frequency or spectral analysis of the PPG signal to identify periodic changes in the PPG signal consistent. An example of this approach is disclosed in U.S. Pat. No. 10,178,973 B2 entitled "Wearable Heart Rate Monitor." Venkatraman discloses that a user's heart rate can be determined from an optical PPG signal using a process that outputs the "periodic component" of the PPG signal. Venkatraman does not teach to determine the events of aortic valve closing nor aortic valve opening, per se.

Thus, devices designed to measure other physiological parameters are not suitable for the reliable determination aortic valve closure. In peripheral pulse waveforms, the signal associated with aortic valve closure is 50 to 100 times smaller than the signal associated with aortic valve opening. Accurate detection of aortic closure with a wearable device requires a carefully considered measurement system that incorporates physical and operational features distinct from those conventionally used to detect other physiological parameters. The following sections detail these physical and operational features, with some details and examples specific to optical sensing technologies. One of skill in the art will recognize that many of the same principles can be used with alternative measurement technologies.

Sampling Resolution. The ability to assess hydration at a level useful to the user requires high resolution of the change in blood volume, flow, or pressure in both the temporal domain and the signal amplitude domain. In the temporal domain, a sampling rate near or above 100 Hz facilitates determination of the events of aortic valve opening and closing to within 10 ms. Lower sampling rates can increase the error in ejection time calculation and hence subsequent hydration assessment. In the signal amplitude domain, amplitude resolution should be sufficient to resolve the changes associated with aortic closing, which are on the order of 1% of the magnitude of changes related to aortic valve opening. In embodiments where acquired signals are digitized through an analog-to-digital converter, the bit-depth of the system should be sufficiently high such that signals related to the aortic valve closure are not lost with discretization.

In optical systems, the amplitude of signals associated with aortic valve closure can be enhanced by increasing the intensity or brightness of light used, provided that detectors and other aspects of the data acquisition system are not saturated. Light intensity can be increased with increased LED drive current or by increasing the number of LEDs in use, or both. Signal amplitude can also be increased by configuring additional operational parameters of the optical system, such as the integration time (length of time that photons are acquired at the detector). In wearable devices that are intended to be worn for prolonged periods battery life is always a concern. Because LED activation can produce a significant drain on batteries, overall LED intensity and duration of use can be considered prudently and used only as needed.

Figures 9A, 9B, 9C:
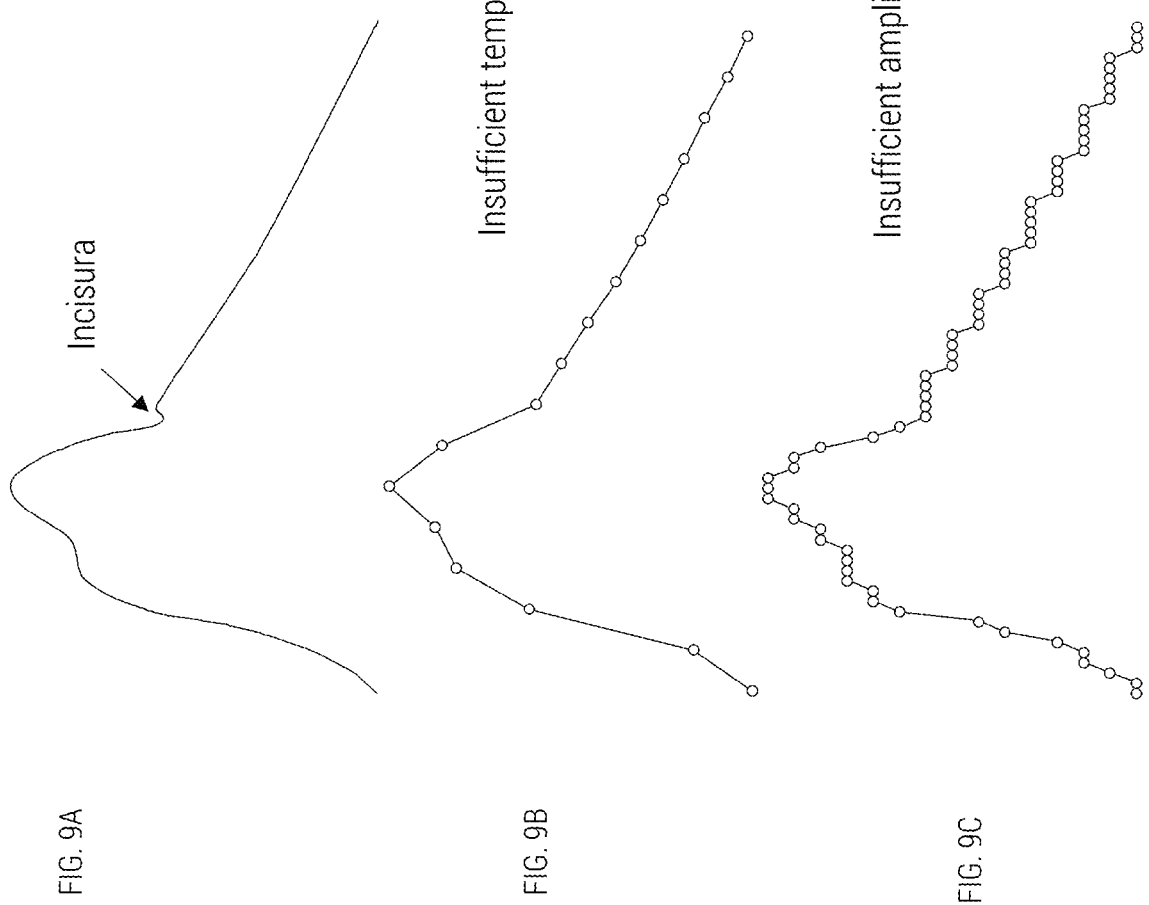
FIG. 9 shows the influence of sampling resolution on determination of aortic valve closure.

FIG. 9 demonstrates the effects of insufficient resolution on determination of aortic valve closure. FIG. 9A shows the pressure trace of a cardiac pulse sampled with high resolution in both domains. Aortic valve closure is determined from the incisura in the pressure wave. When the pulse is sampled with low temporal resolution of 16 Hz in FIG. 9B, the ability to determine the timing of the incisura is significantly degraded. A sampling rate of 16 Hz is common for heart rate determination in wearable devices but is insufficient for aortic valve closure determination. In FIG. 9C, the temporal resolution is improved but the resolution of the amplitude has been strongly degraded due to discretization. Here again, the precise timing of the aortic valve closure is difficult to discern. Thus, embodiments of the invention comprise a measurement system with the resolution in both the time and signal amplitude dimensions to enable detection of the aortic valve closure.

Sampled Vessels. For measurements of pressure, volume, or flow, the incisura signal associated with aortic valve closure will be largest at more proximal arterial segments and will dissipate along the vasculature tree. The signal will be more apparent in larger tri-layered vessels such as arteries and arterioles than in the largely inelastic capillaries.

As it relates to optical systems, near-infrared light, which is absorbed weakly by blood and tissue, can penetrate deeply (>1 mm) into the tissue and interact with larger vasculature segments. This contrasts with shorter wavelengths in the visible range, in particular green light, which is strongly absorbed by pigments in skin, blood, and tissue. For green light, the capillary bed effectively serves as a screen to prevent direct interaction with larger vessels. Thus optical sensors employing shorter wavelengths (green or blue light) with short optical paths that interact with capillaries have less sensitivity to the signal associated with the aortic valve closure than sensors employing longer wavelengths (red and infrared) with longer optical paths that interact with more proximal arterial segments.

The physical configuration of light emitters and detectors in an optical system also plays an important role in determining the optical path length and the type of vessels that are sampled. When the emitters and detectors are placed in close proximity (e.g., separated by <5 mm) the detected photons are more likely to have interacted primarily with superficial vessels in the capillary bed. When the detector is at greater separation from the emitters, the photons that reach the detector are more likely to have interacted with deeper tissue containing more proximal arterial segments. Because shorter wavelengths of light in the visible range are so strongly absorbed by tissue, emitters and detectors must be in relatively close proximity to enable sufficient photon detection. However, longer wavelengths in the red and near-infrared range can be used when emitters and detectors are physically separated by more than 10 mm, supporting optical paths where the majority of photos interact with artery and arteriole segments. To further encourage interaction with such vascular segments, emitters and detectors can be arranged such that the optical path traverses known anatomical locations of arteries. For example, in the fingers, the prominent palmar digital arteries run longitudinally along the sides of fingers, close to the volar surface of the hand. Therefore, more volar (ventral) placement of emitters and detectors can be advantageous to sample the arteries.

Notably, maximization of SNR related to aortic valve closure might not be equivalent to maximizing SNR for aortic valve opening. Because green light is so strongly absorbed by blood, the magnitude of the pulsatile signal associated with aortic valve opening can be significantly larger than the signal obtained with longer wavelengths. In addition, green light sensors are less influenced by venous compartments due to their shallow penetration depths, reducing sensitivity to some motion-related artifacts. The result is that for conventional wearable systems measuring heart rate and heart rate variability, green light can be optimal. This is taught, for example, by Maeda et al (Maeda, Y., Sekine, M., & Tamura, T. (2011). The advantages of wearable green reflected photoplethysmography. Journal of Medical Systems, 35(5), 829-834).

For the purpose of a hydration measurement, the system seeks to maximize the SNR related to aortic valve closure by deeper sampling of larger vessels such as arteries and arterioles that maintain a stronger signal of aortic valve closure.

Tissue-Sensor Interface

A prominent noise source for all sensing technologies is movement of the measurement device relative to the tissue. Device design can mitigate this issue, by protruding sensing components relative to the surface of the device such that they maintain consistent contact with the tissue.

For optical systems, device design can also reduce noise caused by ambient or stray light. Preferably, only light rays that have interacted with the tissue will be captured by the detector. However, light rays that have merely bounced off the skin or other surfaces, or that originate from environmental sources might also be detected and constitute a source of noise. Embodiments of the invention can include light-management components that control or restrict detected light. These components include but are not limited to physical blockers placed around the detector to limit the angles of light rays that can reach the photosensitive surface, optical elements (such as optical fibers or lenses) placed in front of the photodetector that similarly restrict the numerical aperture of the detector, and polarizers placed between the light source and detector at orthogonal orientations to limit detection of light rays that have only undergone surface reflections.

Additionally, ambient light cancellation (ALC) can be incorporated to remove interference from ambient light. ALC approaches detect light both when LEDs are active and inactive, allowing for compensation of signals in LED active periods by LED inactive periods. An example of ALC circuitry is disclosed by Kim et al (Kim, Jongpal, et al. "Ambient light cancellation in photoplethysmogram application using alternating sampling and charge redistribution technique." 2015 37th Annual International Conference of the IEEE Engineering in Medicine and Biology Society (EMBC). IEEE, 2015).

Size of Physiological Signal

Beyond changes to the operational parameters and configuration of the optical sensor system, the SNR can be increased by changing the size of the pulsatile signal.

The size of arterial pulsations can be increased by decreasing the vascular transmural pressure (TMP), that is, the pressure gradient across artery walls. At least three mechanisms are responsible for this enhancement in pulse size with TMP decrease: (1) decreases in TMP trigger arterial dilations through the local venoarterial reflex (VAR), (2) decreases in TMP trigger the myogenic response, i.e., the relaxation of the smooth muscles in artery walls, and (3) because vessel compliance is a function of TMP, decreases in TMP increase arterial compliance such that a given change in arterial pressure results in a large change in arterial volume. TMP can be reduced by applying external pressure at the measurement site or raising the elevation of the measurement site relative to the heart to decrease hydrostatic pressure.

Optimal external pressure is typically greater than the venous pressure but less than the arterial diastolic pressure; pressures beyond this point will begin to occlude flow and distort the pulse waveform. Based on the work of Balijepalli et al (2014), 95% of individuals aged 18-99 years have a diastolic pressure above 60 mmHg. If the sampling site is near or below the level of the heart, external pressures in the range of 50 mmHg can be appropriate to increase the magnitude of arterial pulsation; FIG. 8 shows example measurement locations of the invention.

FIG. 9 shows the influence of sampling resolution on determination of aortic valve closure.

Figure 10:
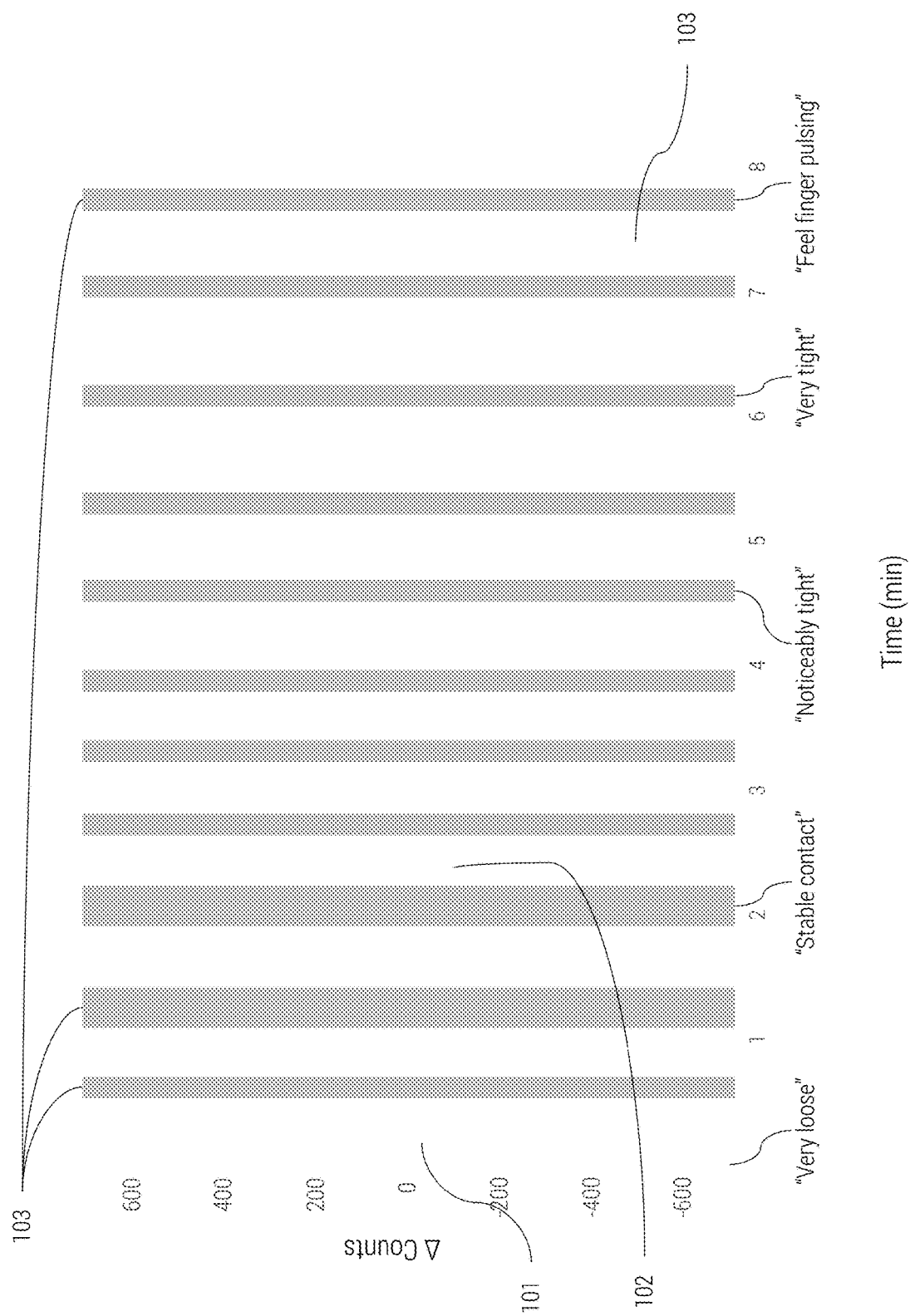
FIG. 10 shows the effect of decreasing transmural pressure on pulse size.
Figure 11:
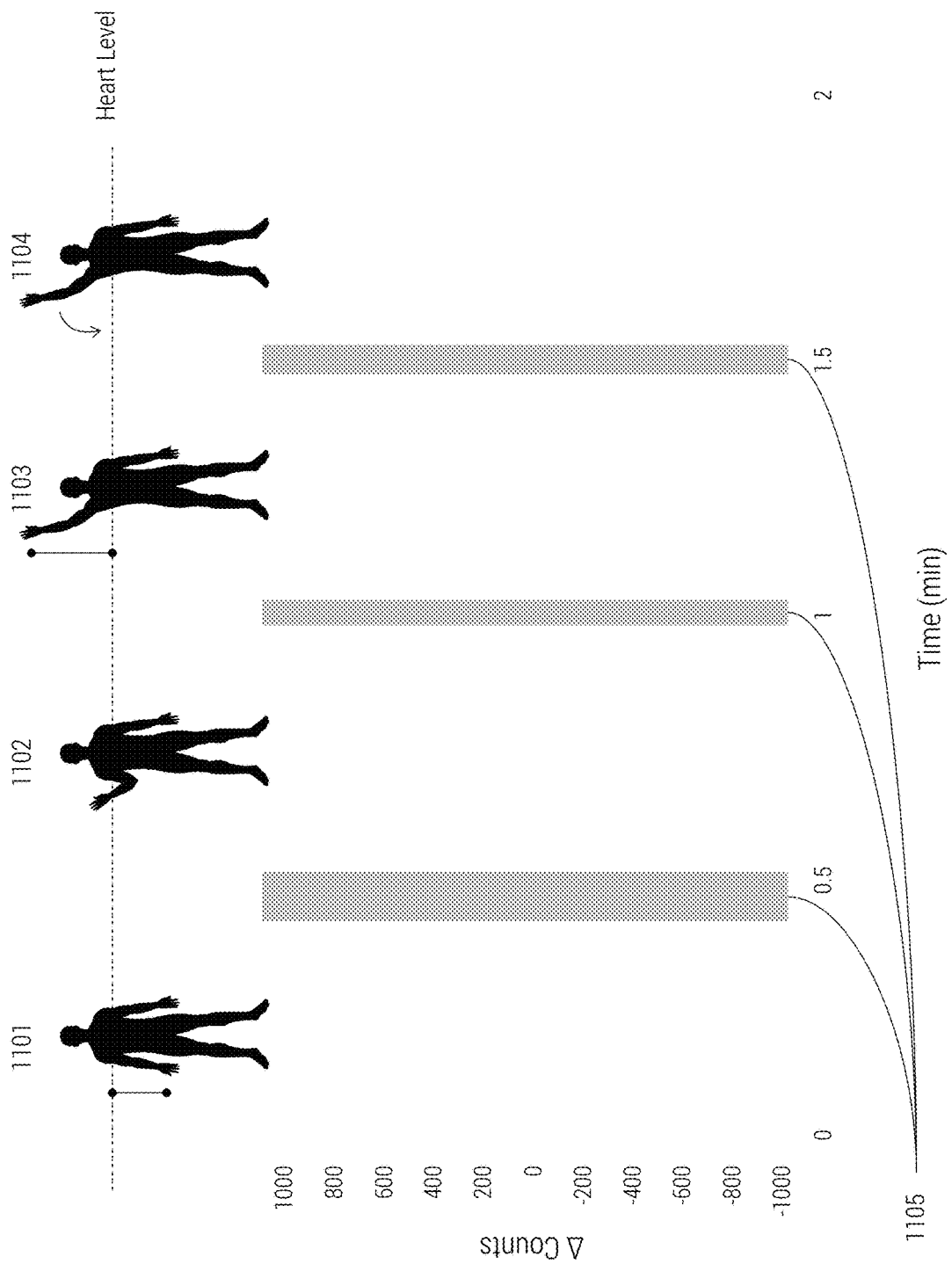
FIG. 11 is a second example of the effect of decreasing transmural pressure on pulse size.

FIG. 10 and FIG. 11 (discussed below), the effect of TMP on pulse size is graded, thus any appreciable external pressure (e.g., greater than 5 mmHg) will produce some increase in the pulse. (Balijepalli, C., Lösch, C., Bramlage, P., Erbel, R., Humphries, K. H., Jöckel, K.-H., & Moebus, S. (2014). Percentile distribution of blood pressure readings in 35683 men and women aged 18 to 99 years. Journal of Human Hypertension, 28(3), 193-200).

By way of comparison, Brophy-Williams et al (2014) report that "sports compression" tights exert an interface pressure in the range of 5 to 30 mmHg, depending on the region of the lower limb and body posture. Coltman et al (2015) find that standard bra straps can exert ~40 mmHg of pressure in static positions, and as much as 75 mmHg during high intensity activities. Thus, an external pressure of ~50 mmHg is not outside the range of pressures exerted by standard garments, though is likely beyond the range of pressures produced by garments or devices intended to be intrinsically comfortable. (Brophy-Williams, N., Driller, M. W., Shing, C. M., Fell, J. W., & Halson, S. L. (2015). Confounding compression: The effects of posture, sizing and garment type on measured interface pressure in sports compression clothing. Journal of Sports Sciences, 33(13), 1403-1410). (Coltman, C. E., McGhee, D. E., & Steele, J. R. (2015). Bra strap orientations and designs to minimise bra strap discomfort and pressure during sport and exercise in women with large breasts. Sports Medicine—Open, 1(1), 21).

Examples of the effect of TMP on pulse size are shown in FIG. 8 shows example measurement locations of the invention.

FIG. 9 shows the influence of sampling resolution on determination of aortic valve closure.

FIG. 10 and FIG. 11. FIG. 8 shows example measurement locations of the invention.

FIG. 9 shows the influence of sampling resolution on determination of aortic valve closure.

FIG. 10 shows the detector signal from an adjustable PPG ring worn at the base of the finger. The signal has been band-pass filtered to focus on the pulsatile component. Roughly every 45 s, the ring is tightened incrementally on the wearer's finger via a ratcheting mechanism on the ring band. These tightening events are denoted by gray rectangles 103. The wearer's reported subjective experience associated with the different levels of tightness are indicated below the graph. Initially in period 101, the ring is reported by the user to be "very loose" and the magnitude of the pulse is ~100 detector counts. After several tightening events the user reports that the ring makes "stable contact" with the finger. The pulse size at this period (102) is ~150 counts. After this point, each tightening event increasingly changes the TMP through applied external pressure, as evidenced by the increase in pulsatile signal size. When the ring is reported by the user to be "very tight", the pulse size increases to ~1000 counts (period 103). After further tightening, the user reports feeling pulsations in the finger, an indication that the external pressure is approaching arterial diastolic pressure. Cumulatively, the tightening events produced a 10% reduction in the circumference of the ring and created a 10-fold increase in signal size is due to the decrease in arterial TMP caused by the increased external pressure at the sampling site.

FIG. 11 shows a second example of the effect of TMP on pulse size, in this case using manipulations in hydrostatic pressure to alter the TMP. FIG. 11 shows a band-pass filtered detector signal from a PPG ring worn at the base of the finger. The ring size is constant throughout the experiment, but the subject undergoes changes in arm positions, indicated by gray rectangles 1105. In period 1101, the arm hangs in a relaxed position at the subject's side. The sampling site is estimated to be 50 cm below the right atrium of heart, resulting in ~37 mmHg of additive pressure distending the walls of the veins and arteries, due to the hydrostatic pressure exerted by the vertical columns of blood in these vessels. The pulse size in this period is just under 400 counts. In period 1102, the subject raises their hand such that the sampling site is roughly level with the shoulder. The change in vertical displacement with respect to the heart decreases the hydrostatic pressure, decreasing the TMP accordingly. The pulse size therefore increases by more than a factor of 2 to nearly 1000 counts. In period 1103 the subject extends their arm to a comfortable position above their head. The sampling site is now an estimated 67 cm above the right atrium, resulting in a hydrostatic pressure of roughly −50 mmHg. This reduces the TMP, which causes a further increase in the pulse size to roughly 1500 counts. In period 1104, the subject slowly lowers their arm down. As would be expected, the pulse size gradually decreases.

Decreasing TMP at the sampling site provides the additional benefit of reducing physiological signals that are unrelated to aortic valve closure. A large source of physiological noise is venous blood. Since the venous system operates at relatively low pressures, it is quite susceptible to the local effects of volume perturbation during motion. The venous blood in the vascular bed will be easily deformed during subtle motion, changing light absorption and producing a significant source of in-band noise. This noise source can be managed by reducing the venous TMP to below zero, effectively collapsing the veins such that their volume is minimized. This not only stabilizes the venous contribution to vascular volume, but also reduces the overall absorbance of light by non-pulsatile sources.

The magnitude of the pulse signal can also be enhanced by increasing the cross-sectional area of the arteries and arterioles at the sampling site via vasodilation. This can be achieved by warming the tissue at the sampling site, for example, with a heating element embedded in the apparatus.

Management of Differences in User State

An effective hydration assessment system can manage differences in user states, or differences across individuals, that are unrelated to changes in hydration status. The following paragraphs describe differences in physiological states that can represent potential confounds for hydration assessment, as well as approaches to effectively manage such differences.

Heart Rate

Some embodiments of the invention provide the ability to determine hydration in the presence of heart rate changes. Heart rate is influenced by many variables, including altitude, age, physical activity, temperature, stress, alcohol, and stimulants such as coffee. Thus, a useful hydration assessment system can provide accurate assessments of hydration in the presence of heart rate changes arising from multiple sources.

A change in heart rate can change the ejection time during conditions of constant hydration. The change in ejection time occurs largely because the heart has less time to fill with blood. For the purpose of detecting hydration, in some embodiments these non-hydration related changes can be mitigated by using heart rate as an additional independent parameter to effectively compensate for ejection time alterations such that an accurate determination of hydration is possible.

Figure 12:
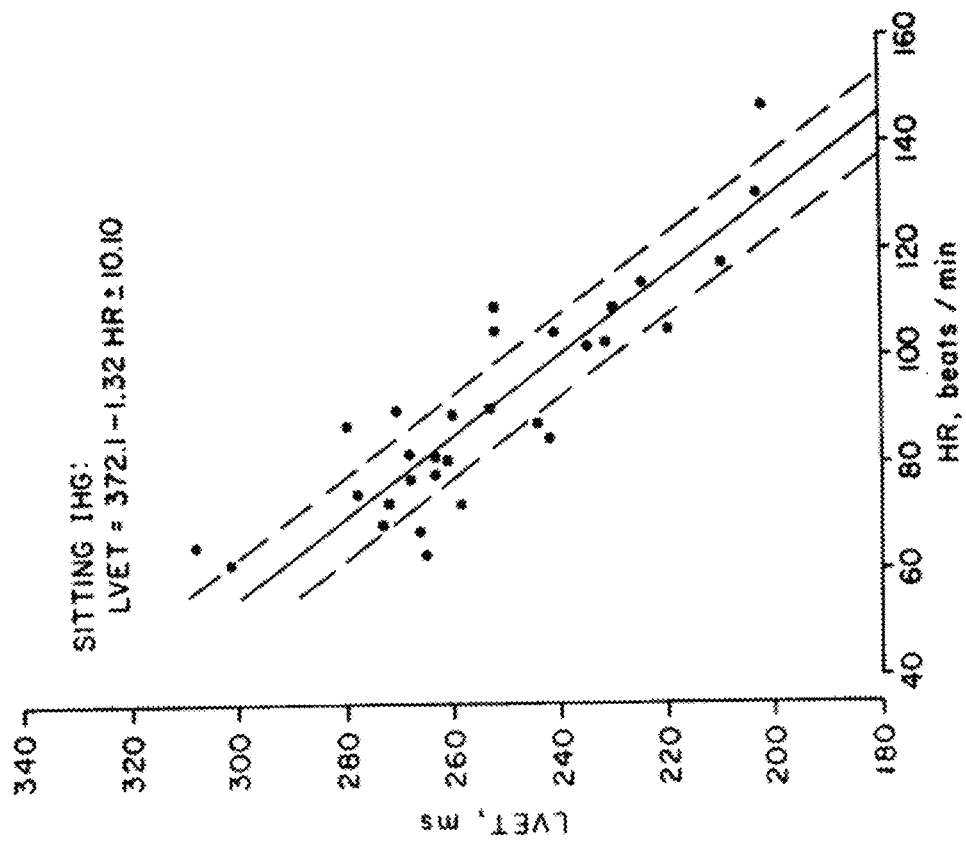
FIG. 12 shows a typical relationship between heart rate and ejection time.

FIG. 12 shows a typical relationship between heart rate and ejection time at a single hydration level, reproduced from Lance et al. (Lance, V. Q., & Spodick, D. H. (1976). Heart rate—left ventricular ejection time relations. Variations during postural change and cardiovascular challenges. Heart, 38(12), 1332-1338.) Ejection time falls roughly linearly with heart rate, although numerous studies show that the precise relationship varies across individuals and is a function of age, gender, and fitness level.

Figure 13:
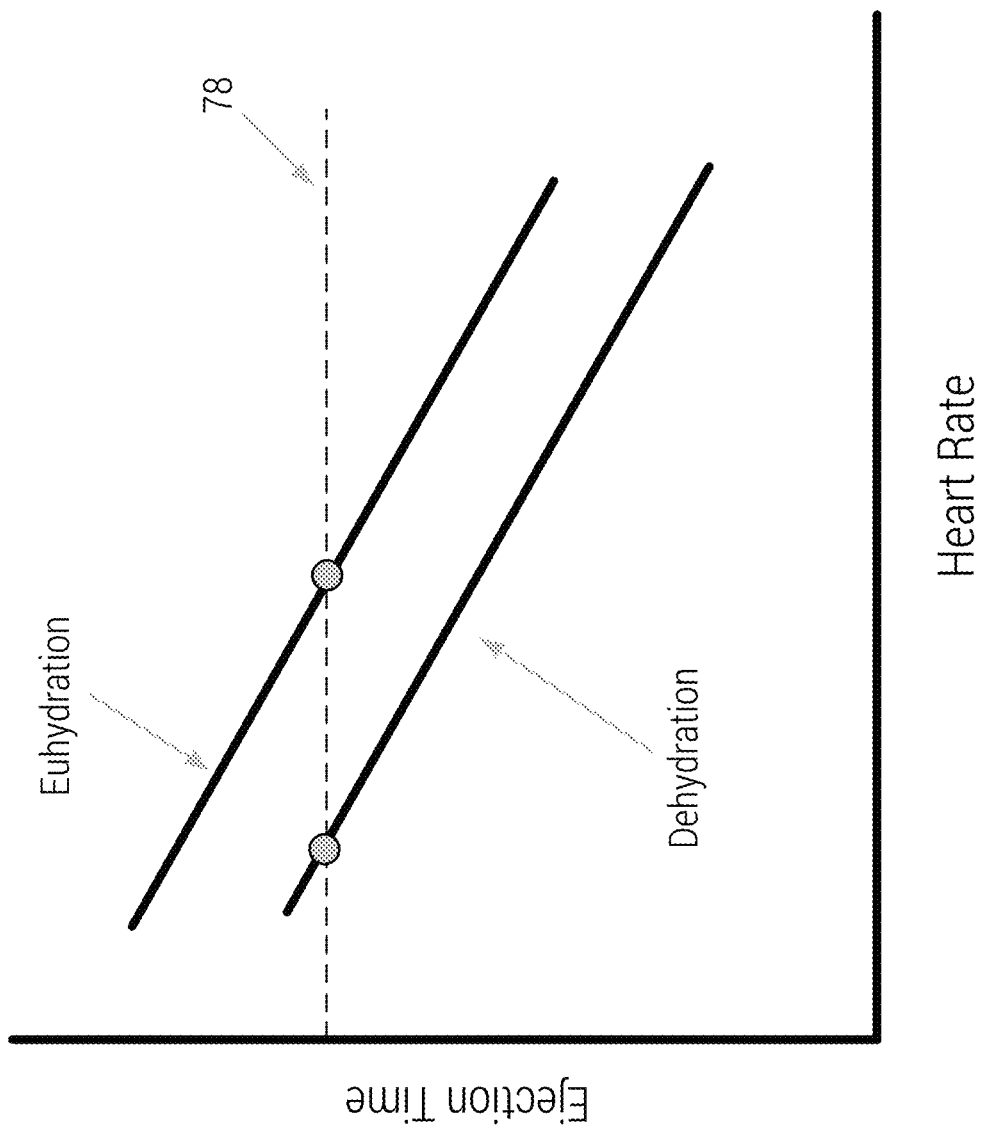
FIG. 13 is schematic of heart rate vs ejection time at two hydration levels.

FIG. 13 illustrates the potential error that can occur if heart rate is not considered in the determination of hydration. The figure shows a relationship between heart rate and ejection time at two different hydration levels. Line 78 shows the potential error of using only ejection time as the metric for hydration. A change in hydration from normal to dehydrated can be missed if the measurements are acquired at a significantly different heart rates. Conversely, an increase in heart rate can be misinterpreted as a decrease in hydration. Some embodiments of the current invention use both heart rate and aortic timing information to effectively determine hydration despite changes in heart rate.

The ability to compensate for heart rate changes can use a simplistic correction for all individuals. However, improved hydration measurements can be possible by using a more refined and user-specific approach. The system can use a "matched cohort" approach based on age, gender, body mass index (BMI) or fitness level. The user can input in such demographic information into the device, or into an application in communication with the device, to support improved heart rate correction.

The hydration assessment system can request that the user undergo a type of heart rate calibration or compensation procedure. Such a procedure can request the user to get a transient elevation in heart rate heart over a measurement period with little or insignificant changes in hydration statues. A more extensive calibration can request the user provide heart rate changes at two different hydration states.

Body Position

Figure 14:
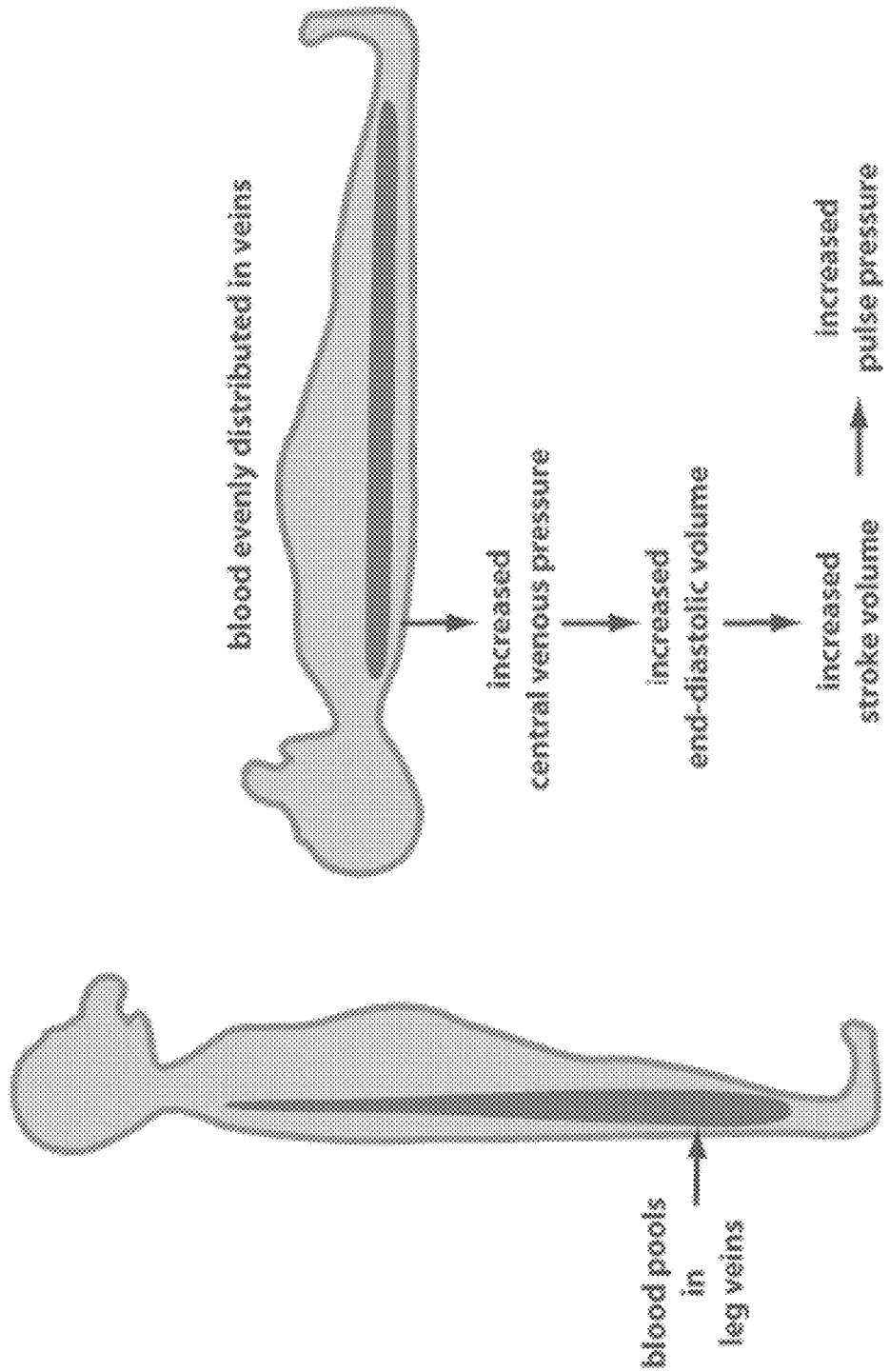
FIG. 14 is an illustration showing the impact of body position on venous return.

Another potential difference in user state is the level venous return into the heart. When in the supine (lying flat), the large veins in the chest are filled or plump with blood. The additional volume creates an increased pressure as the veins are stretched. The result of a supine position is an increased central venous pressure, increased end-diastolic volume, and increased stroke volume. When standing, the pressure in the large veins in the legs increases. For example, one meter below the heart, the effect of gravity adds about 74 mm Hg of pressure. The change from supine to standing causes venous distension and blood pools in the legs. The resulting translocation of blood to the legs reduces the blood in the central veins, and the cardiac filling pressures drop. FIG. 14 is a pictorial representation of the above physiology.

Figure 15:
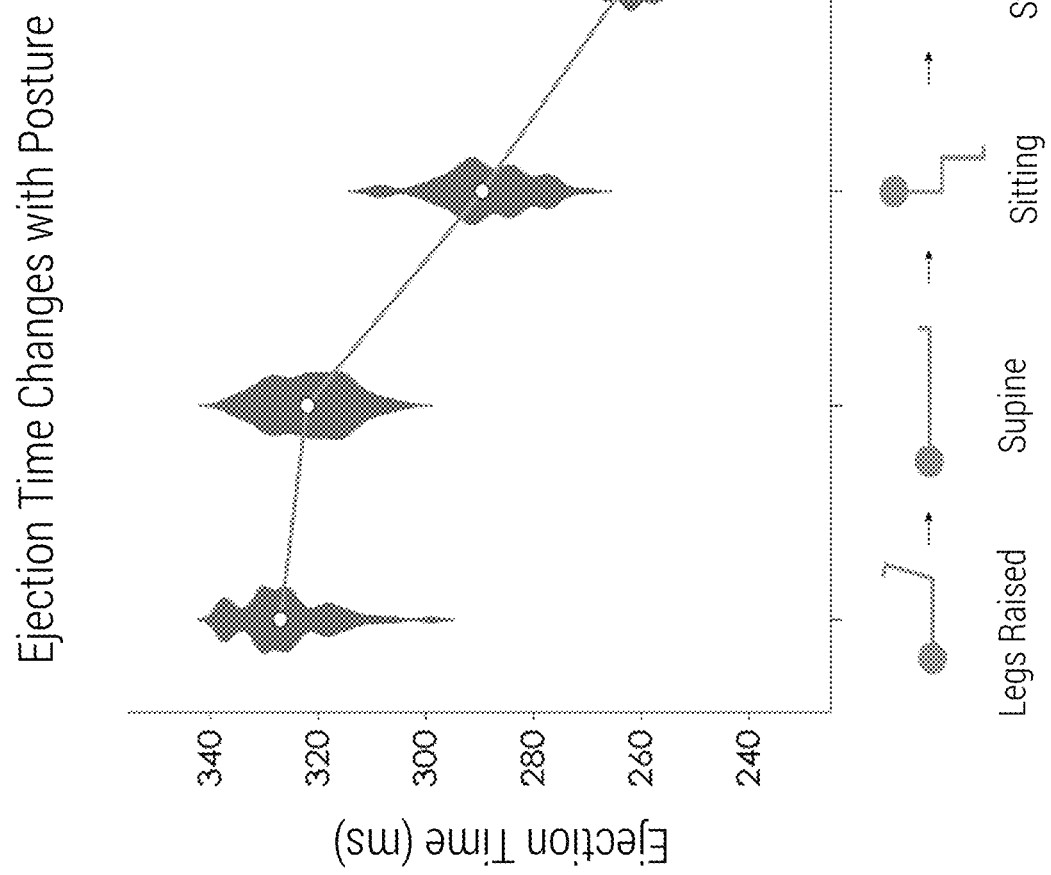
FIG. 15 shows the relationship between ejection time and body posture.

The impact of body position on ejection time in a constant hydration state is shown in FIG. 15. The figure shows measurement results (ejection time in ms) of moving a subject through 4 positions: legs raised, supine, sitting and standing. The estimated volume changes between legs up and flat is estimated to be 150 ml. As demonstrated, body position changes impact aortic timing and are potential hydration errors. For example, a decrease in venous return due to a position change can mimic a change in hydration.

Thus, the hydration assessment system can be used when individuals are in a fixed body position, e.g., standing. Examination of FIG. 14 illustrates that standing decreases central venous pressure and end-diastolic pressure. Re-examination of FIG. 6 and FIG. 7 shows that the overall sensitivity to hydration changes is greatest at lower end diastolic pressures. Thus, requesting the subject always stand during the hydration measurement (rather than sit or lay down) can improve the accuracy of the hydration measurement.

Alternatively, information about the user's body position at the time of the measurement can be taken into consideration. Body posture can be determined in many ways, including direct measurements, inferred measurements or self-reported measurements.

Figure 16:
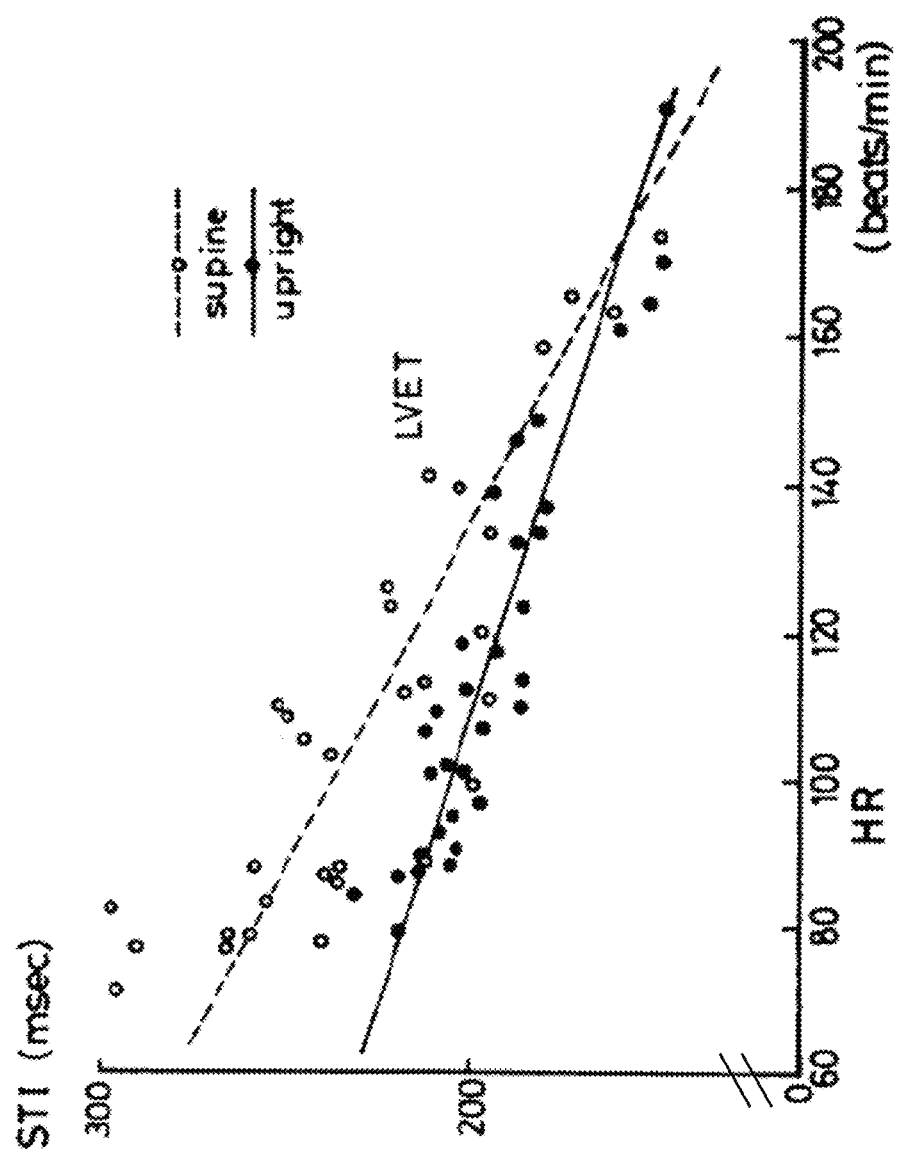
FIG. 16 shows heart rate and ejection time relationships at different body postures.

The effect of heart rate on ejection time interacts with body position. This is shown by Miyamoto et al, reproduced in FIG. 16 (Miyamoto, Y., Higuchi, J., Abe, Y., Hiura, T., Nakazono, Y., & Mikami, T. (1983). Dynamics of cardiac output and systolic time intervals in supine and upright exercise. Journal of Applied Physiology, 55(6), 1674-1681.). The slope relating ejection time to heart in the supine position is steeper than that in the upright (standing) position. Thus, both the body posture and heart rate can be considered in concert to make an effective hydration assessment.

Changes in Body Position

In addition to controlling for body position, acquiring measurements over different body positions can be used to perform the hydration assessment. Additionally, changes in body position can be used to create a self-referenced measurement where the degree of change between positions is compared or calculated and compared against an existing standard. The comparison standard used can be a general population-based standard that is used for all users. The standard for comparison can be a "matched" standard where the selected standard is based on parameters associated with a cohort of users that match characteristics of the user. For example, potential matching features can include, but are not limited to, gender, age, body mass index, height, physical fitness, use of tobacco, etc. A final standardization can be based on self-determined standards. The user can establish their response when adequately hydrated and a secondary response standard at a defined dehydration level. In use, the self-reference approach can be used to access hydration status in the morning when rising from the bed. The system can use postural transitions from sleeping to sitting to standing as a method for accessing aortic valve timing under three different venous return conditions. The ability to compare day-to-day trends for a single individual enables the system to identify small perturbations in hydration that can influence physiological performance.

Incorporating Information

Figure 17:
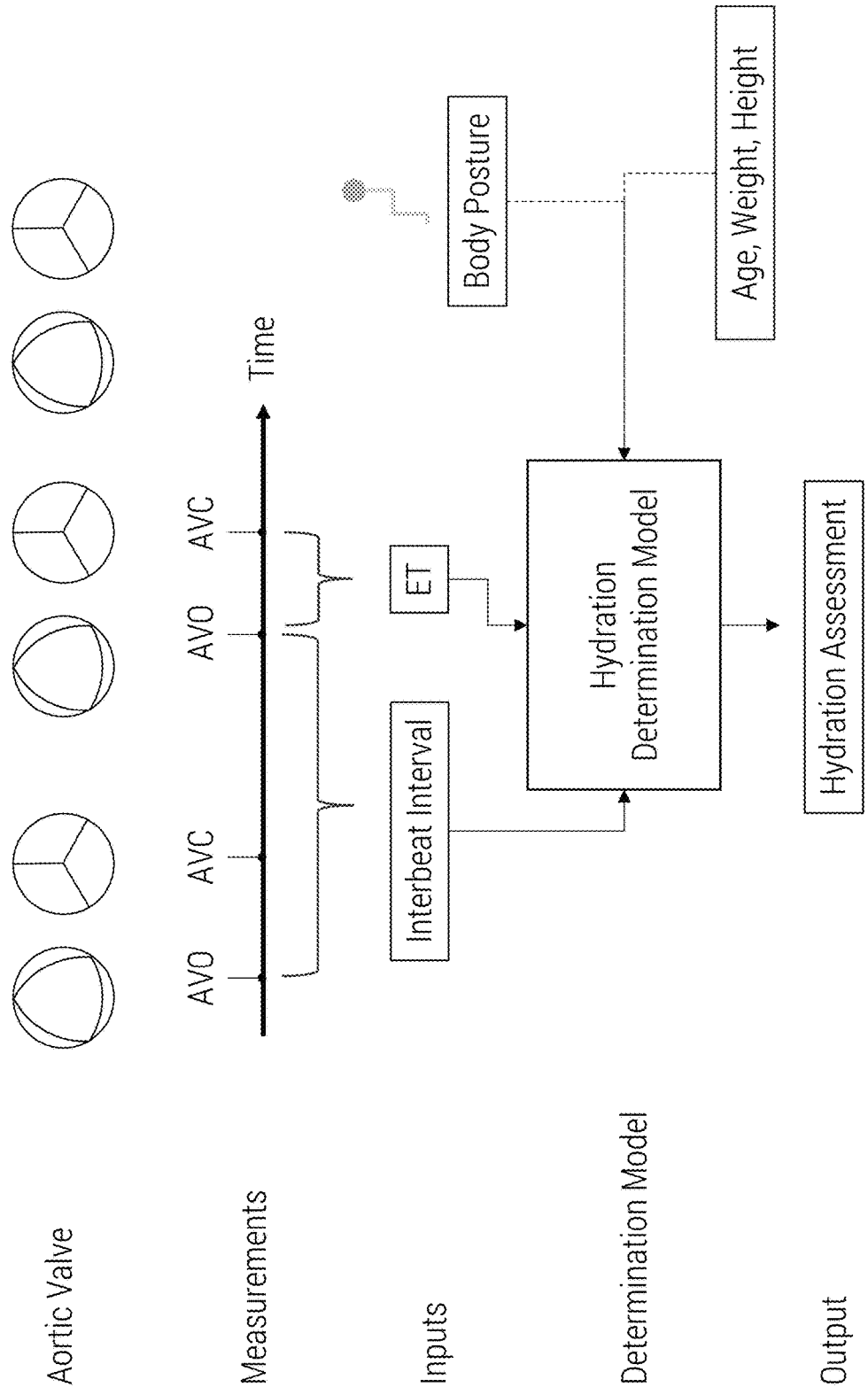
FIG. 17 illustrates a set of the inputs that can be used for hydration determination.
Figure 18:
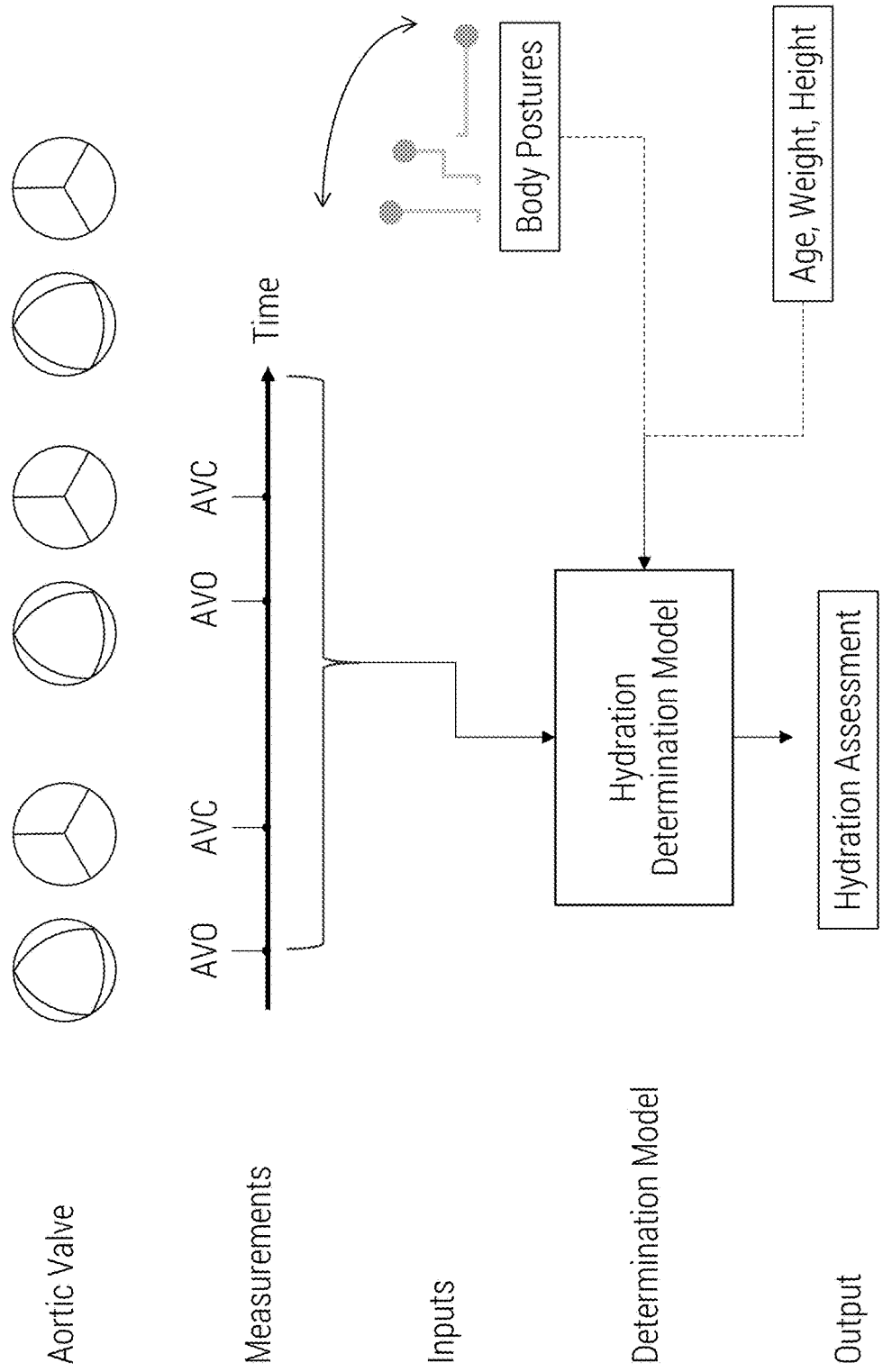
FIG. 18 illustrates an alternative set of the inputs for hydration determination.

FIG. 17 and FIG. 18 illustrate the incorporation of information about user state into the effective determination of hydration status. As shown in FIG. 17, hydration assessment depends primarily on the time course of aortic valve opening and closing, from which the interbeat interval (IBI; the inverse of heart rate) and ejection time (ET) are determined. Additional inputs can include body posture, which can be assumed based on user compliance, acquired based on input from the user, or determined from sensors, as well as physiological information about the user, such as age, weight and height. These inputs are then used by a hydration determination model to produce the desired output of hydration status.

FIG. 18 represents a variant on the prior example. In this example, the hydration determination model incorporates the time course of aortic valve opening and closing acquired at more than one body posture. As before, the postures can be assumed based on user compliance, acquired based on user input, or determined from sensors. Also as before, demographic information about the user can comprise an additional input to the hydration determination model. Distinct from FIG. 17, the hydration determination model in this example does not take as input the explicitly calculated ET and IBI; instead, the model utilizes a data representation that contains information associated with aortic valve opening and closing. Deep neural networks, particularly those with convolutional layers or recurrent structures, can be trained to predict hydration status based on a data stream, using information in the data stream that is inherently associated with the opening and closing of the aortic valve. The data stream used by the determination model can be raw (unprocessed), or can be processed, filtered, or transformed, in some manner prior to being entered into the model.

One of skill in the art will recognize that the above approaches to incorporating information for hydration determination comprise limited examples and that many other approaches are possible.

Example Apparatuses for Hydration Assessment

Figure 19:
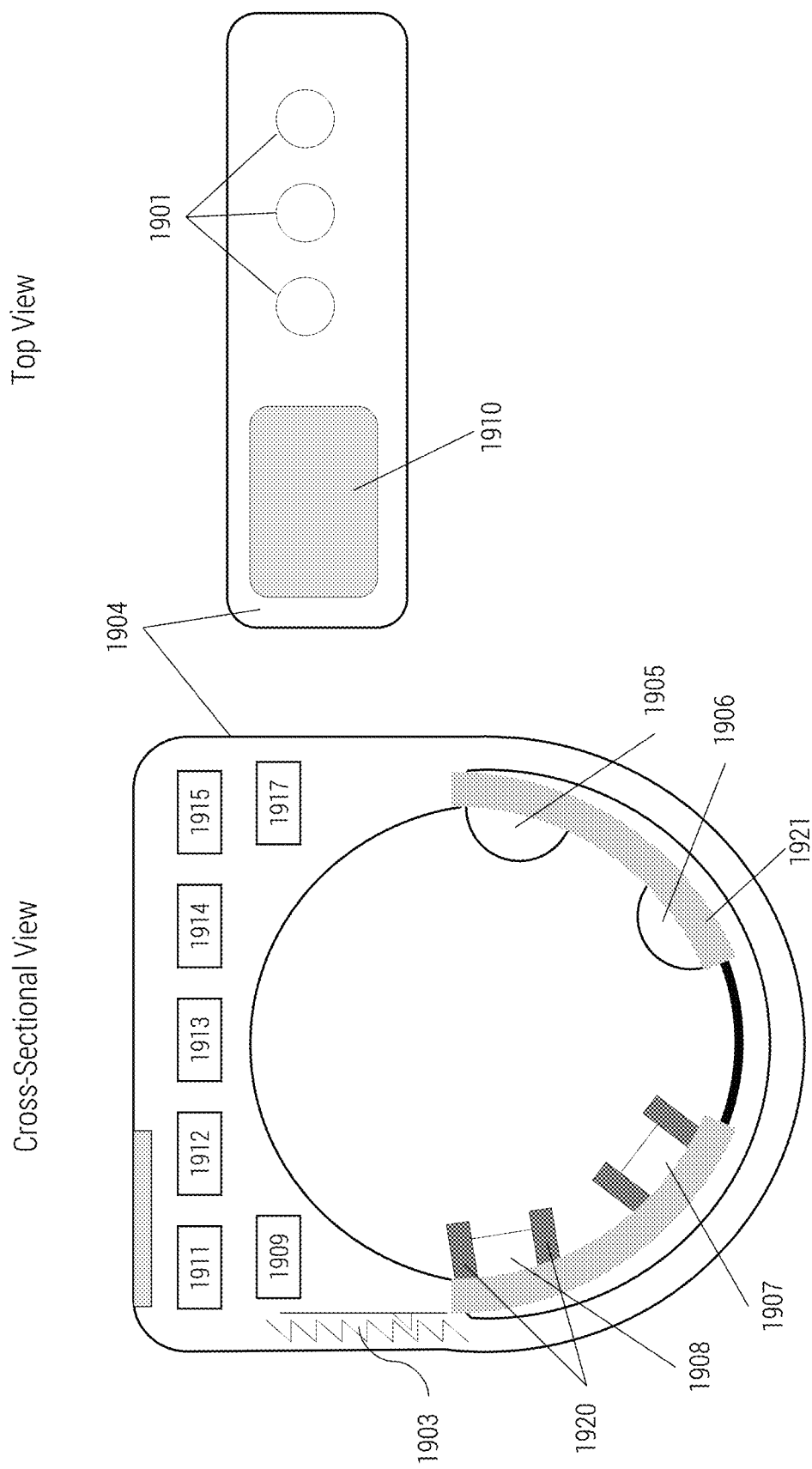
FIG. 19 shows an illustrative embodiment of the apparatus used to measure the aortic valve time series.

FIG. 19 shows an illustrative embodiment of an apparatus (1904) capable of making a hydration measurement based on aortic valve opening and closing. In the example embodiment, the apparatus is configured as a ring to be worn on a finger. The apparatus includes one or more of the operational systems described below. Functional element(s) of each system are described, though additional capabilities can also be present.

Key Systems of Operation

The apparatus includes an optical sensor system comprising one or more emitters (1905 and 1906) and one or more detectors (1907 and 1908). The optical sensor system is used to emit photons into the tissue at a sampling location and detect photons that have interacted with the tissue. In this embodiment, physical blockers 1920 surround the detectors to limit the influence of stray light. The emitters can have the same emitting wavelength or different wavelengths. A given emitter can also represent a package of LEDs, with the capability to emit a plurality of wavelengths. The detectors can be the same or different, with regard to their active area, spectral sensitivity, or other parameters. The optical sensor system can be configured to perform time-division multiplexing and de-multiplexing, such that signals from a plurality of wavelengths can be acquired during the same acquisition period. The optical sensor system can be further configured to perform ambient light cancellation.

A motion sensor system, e.g., accelerometer 1909, is used to obtain motion information at the sampling location. In alternative embodiments, the motion sensor system can comprise sensors that quantify motion in at least one dimension, such as accelerometers, gyroscopes, magnetometers, barometers, and altimeters. One or more of these sensors can be present in an inertial measurement unit (IMU). The motion sensor system can also quantify the degree of motion based on variance in the detector signal from the optical sensor system. Other systems for motion assessment include optical or image detection systems. The motion sensor system can use a singular source of information of motion assessment or combine information from sensors as needed.

A trigger system, e.g., button 1910, is configured to detect a trigger (e.g., pressing of the button) and then initiate a hydration measurement. In other embodiments, the trigger system can be configured to detect a sensor-based, user-based, or time-based trigger. A sensor-based trigger refers to initiation of a hydration measurement based on sensor signals. For example, little or no motion (as sensed by the optical sensor system) or the detection of large pulsatile signals (as sensed by the optical sensor system) can indicate the presence of suitable measurement conditions and can constitute a triggering event in isolation or combination. User-based triggers refer to the initiation of a hydration measurement based on any intentional activity generated by the user. Examples include both activities with the apparatus itself or with an external device in communication with the apparatus. Direct interaction with the apparatus can include a tap, turn, or twist of the device in a defined manner, or a defined hand or finger gesture. In such cases, the trigger system would be configured to be responsive to the motion sensor system. Alternatively or in addition, the trigger system could be configured to be responsive to a user input system, defined below. For example, users can interact with an application on a smartphone to initiate a hydration assessment. A further example can include a triggering event based on voice commands or a defined sound sequence. Lastly, time-based triggers refer the initiation of a hydration measurement based on absolute or relative timing. Such triggers include the elapsed time since the last hydration measurement (e.g., 30 minutes since the last successful measurement), a specific time of day (e.g., 6:00 AM and 10:00 PM every day), or times dictated by or by the user's circadian rhythms (e.g., after the user falls asleep or gets out of bed).

An optical sampling control system (1911) is used to establish and change the operational parameters of the optical sensor system. Operational parameters include parameters of the optical sensor system that can be configured at the initiation of sampling, to include emitter and detector selection, wavelength selection, sampling frequency, detector integration time, ambient light cancellation, and the duration of sampling. During a hydration measurement, when detection of aortic valve opening and closing is required, the following operational parameters for the optical sensor system shown in FIG. 19 in can be suitable: use of both emitters (1905 and 1906) with a near infrared wavelength (e.g., peak wavelength of 940 nm) at near maximal intensity (e.g., drive current of 60 mA); use of detector 1908 to encourage a long optical path with deep sampling of arteries and arterioles, with a maximal integration time of 100 µs; sampling frequency of greater than 100 Hz; acquisition duration of 30 seconds. The above operational parameters are provided for illustration only; variations of these parameters can also be suitable. When a hydration measurement is not taking place, the optical sampling control system can specify a different set of operational parameters. For example, if only heart rate is being determined, the operational parameters can be altered to reduce power requirements and conserve battery life. Such operational parameters can include: use of a single emitter 1906 emitting green light (e.g., peak wavelength of 530 nm) at sub-maximal intensity (e.g., 15 mA); use of detector 1907 to encourage a short optical path where photons largely interact with the capillary bed; sampling frequency of 16 Hz. During periods where no optical measurements are required, the optical sampling control system can also fully inactivate the optical sensor system (achieving an effective sampling rate of 0 Hz for all detectors and drive current of 0 mA for all emitters) to further conserve power.

An analysis system (1912) receives signals from one or more detectors in the optical sensor system and determines the ejection time and inter beat interval. The analysis system can combine or otherwise aggregate signals from one or more detectors and from one or more wavelengths. The analysis system can also use signals from the motion sensor system, e.g., accelerometers and/or gyroscopes, which can be used to minimize or eliminate noise in the detector signal caused by motion or other artifacts. In addition, the system can incorporate signals or extracted features from prior sampling periods. The analysis system can employ filtering or signal transformation, noise-cancellation, feature detection, algorithmic processes, probabilistic models, prediction models, or other analytic techniques.

The analysis system can further comprise a signal suitability system (1913), which determines a metric indicative of the suitability of the acquired signals for hydration determination such that a reliable result will be generated. The determination of suitability can be based on a variety of factors, to include the stability and consistency of the raw or processed detector signals, the consistency or model-based likelihood of extracted features such as ET and IBI, the magnitude of motion as determined with the motion sensor system, the estimated degree of motion contamination in the detector signals. The signal stability system can use outlier detection methods, anomaly detection methods, probability models, or other techniques to assess suitability. The signal suitability system can be configured to determine the cause for a lack of signal suitability and provide this diagnostic information to the user via a feedback system such that corrective action might be taken. Additionally, the signal suitability system can be configured to provide information to the optical sampling control system such that changes in operational parameters can be implemented to improve the quality of acquired signals.

A posture determination system (1914) is a system for determining the body posture of the user. In the illustrative embodiment of FIG. 19, the posture determination system is configured to be responsive to the motion sensor system 1909. In general, a number of technologies can be used to perform posture determination, but approaches can be grossly divided into (1) direct measurements, (2) inferred measurements and (3) self-reported determination. Direct measurements to determine posture include data from sensors that enable detection of body movement, such as accelerometers, gyroscopes, magnetometers, and cameras or other imaging platforms. These sensors can be worn on the user, or can observe the user from an unattached position, or a combination thereof. Inferred measurements to determine posture rely on the current activities of the user. For example, when sleeping it is reasonable to assume that the user is in a supine or semi-recumbent position. When traveling at a significant speed (e.g., >30 mph) one can infer a seated position in a car or other vehicle. In some embodiments, self-reported measurements of posture determination include the user reporting their posture using a user input system (1917).

A hydration determination system (1915) takes the IBI, ET, and potentially additional information, such as user input, to determine the hydration status of the user. The resulting information can be communicated to the user via feedback system (1901).

A feedback system comprising display LEDs 1901 provides feedback to one or more recipients. The recipient can include the user and/or an interested party or parties, such as coaches, teammates, caregivers, or medical professionals interested in the hydration status of the user. Feedback as used herein refers to the transfer of any information related to hydration status or a hydration measurement. For example, the feedback can communicate the hydration status of the user, the quality of signals acquired during a hydration measurement, or instructions for making a measurement or taking corrective actions. Feedback on hydration status can be provided to in real or near real-time, allowing the recipient to make near-term lifestyle, fluid consumption, activity, or medication changes to improve performance, recovery, health status, and general wellbeing. In alternative embodiments, feedback can be provided on the device itself, or on an external device, such as a smartphone, cyclometer, smart waterbottle, smart watch or personal computer in communication with the device. Feedback can be visual (e.g., via a readable display or LEDs), audible (e.g., beeps, tonal patterns or speech), tactile (e.g., produced by vibratory or haptic technologies), in the form of an action (e.g., the lid of a smart water bottle popping open) or any combination thereof.

A user input system, Bluetooth receiver 1917, allows information to be transferred from the user to the device. In other embodiments, the user input system can be configured to receive input in many forms to include physical interaction, voice interaction, gesture interaction and other communication methods. For example, to receive physical input, the user input system can comprise a button or switch. To receive gesture input, the user input system can comprise a gesture detection system responsive to the motion sensor system. Gestures can include tapping on the device, rotating the device, or a motion sequence such as clapping the user's hands three times. Additional examples of communication methods include wireless transmission with electromagnetic or ultrasonic waves, wherein the user input system would comprise an appropriate receiver.

Figure 20:
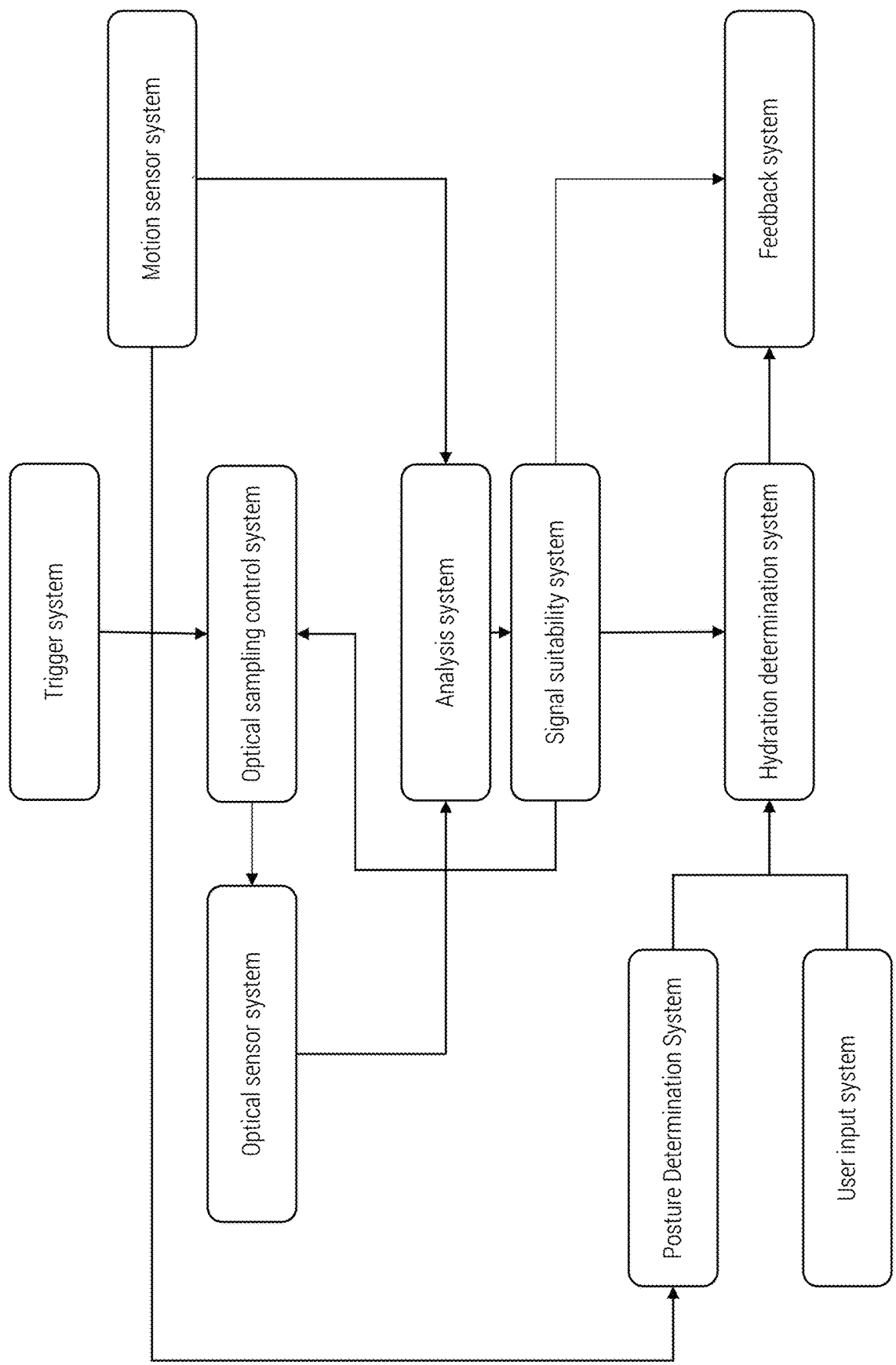
FIG. 20 presents an example of how the systems of the illustrative embodiment can interact.

The process of obtaining a useful hydration measurement involves coordination and dependencies between various systems. FIG. 20 depicts the operational relationships between the described systems in the illustrative embodiment of FIG. 19. Alternative embodiments can include a subset of interactions, additional interactions, other otherwise differentiated dependencies.

Mechanisms for Decreasing Transmural Pressure

Figure 21:
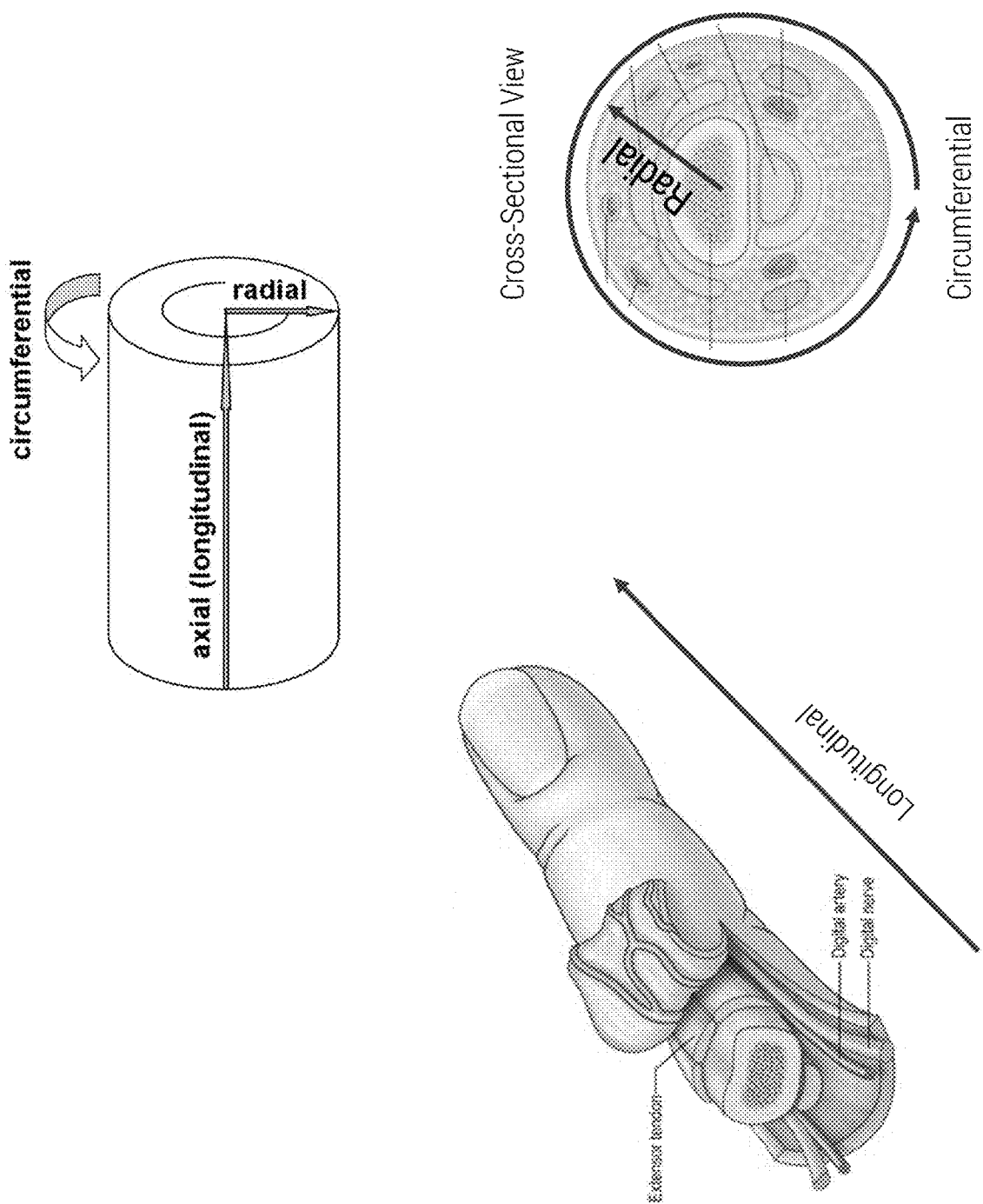
FIG. 21 defines a coordinate system for a finger or other body member.

The apparatus can be configured with mechanisms that change the transmural pressure at the sampling site. To facilitate effective description of these mechanisms and their operation, FIG. 21 defines a coordinate system based on a finger on which the apparatus is worn. The longitudinal dimension is aligned with the length of the finger, and specifically a phalange. An orthogonal radial dimension is defined from the center of the finger to the skin surface. A circumferential dimension, perpendicular to both the longitudinal and radial axes, is defined around the circumference of the finger. Analogous coordinate systems can be defined for other body members. For example, the longitudinal dimension for the wrist is aligned with the length of the ulna and radius, and for the upper arm is aligned with the humerus bone.

The apparatus can be configured to decrease transmural pressure by applying external pressure to the sampling site or in adjacency to the sampling site. Because fingers and other body members are semi-rigid objects with limited deformation capabilities, pressure applied to one location is transmitted throughout the volume of tissue with reasonable efficiency. For the finger, an adjacent area is considered to be within a given phalange. External pressure can be exerted locally, circumferentially, at a single longitudinal location or distributed along the longitudinal axis.

Figure 22B:
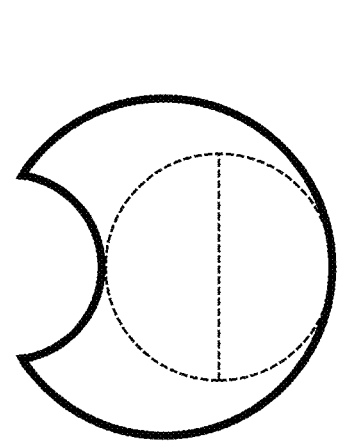
FIG. 22 defines the effective internal diameter for a ring-type device.
Figure 22A:
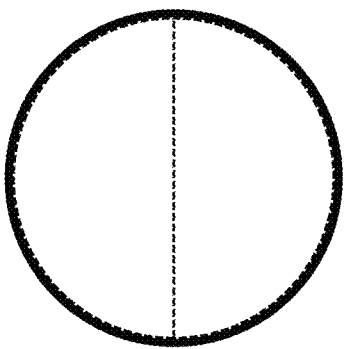
Figure 22E:
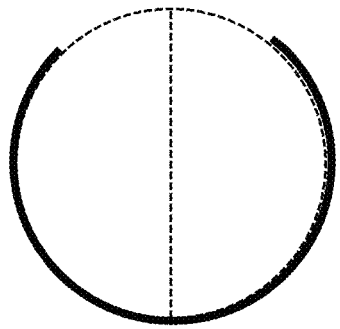
Figure 22D:
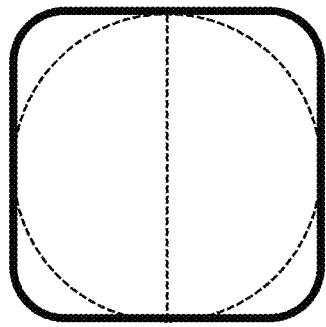
Figure 22C:
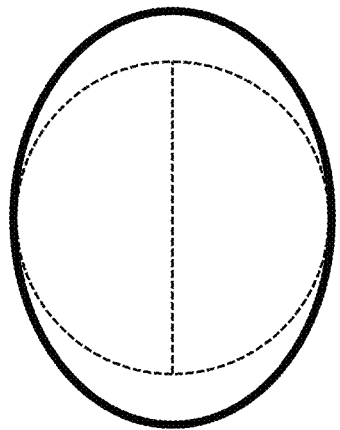

The apparatus can be configured to decrease transmural pressure by decreasing the effective internal diameter of an internal surface that surrounds all or a significant portion of a finger or other body member. The effective internal diameter is defined as the largest circle that can be inscribed by the internal surface of the apparatus, as viewed from a longitudinal projection. FIG. 22 illustrates the determination of effective internal diameter for a number of different ring-type forms that can partially or fully encircle a body member. In FIG. 22A-F, thick black lines denote the internal surface of the ring; dashed lines denote the largest inscribed circle and corresponding diameter. FIG. 22F shows the effective internal diameter for a ring with an open form (i.e., does not completely encircle or enclose the body member).

For the purposes of illustration, several different mechanisms for changing effective internal diameter will be discussed, as incorporated into a finger ring; the majority of these mechanisms are equally applicable to devices worn around the wrist, upper arm, or other body members. For purposes of explanation, configurations that exert less pressure at the sampling site will be referred to as the "worn state", whereas configuration exerting greater pressure (and thus reducing transmural pressure) will be referred to as the "measurement state".

One means for changing effective internal diameter is through a gross change in the inner circumference of the ring, similar to tightening or loosening a belt. Embodiments of this type are considered to have a reducible internal circumference. The illustrative embodiment in FIG. 19 includes such a means for changing the effective internal diameter: an integrated ratchet mechanism 1903 that can tighten the inner flexible surface of the ring 1921 during a measurement state, and loosen it during the worn state. FIG. 23A-B shows a second example of a gross reduction in inner circumference. This example embodiment shows an open form ring capable of flexure when force is applied. In the worn state (FIG. 23A), the ring form remains open. To achieve the measurement state (FIG. 23B), the user applies force to the sides of the ring (across the opening) to compress the ring to the defined stop location. A trigger system can be configured to sense when contacts, 2301, at the open ends of the ring meet, and the initiate a hydration measurement. This process constitutes a user-based trigger, as well as a trigger based on the detection of a change in effective internal diameter.

A signal suitability system can require persistent contact throughout signal acquisition as criteria for signal suitability. Additional examples of embodiments configured for gross circumferential change rings are shown in FIG. 23C-E. FIG. 23C is similar to the device of FIG. 23A in that application of force by the user reduces the circumference and compresses the ring to a defined stop. FIG. 23D also changes from an open form to a closed form, and incorporates a clip mechanism to maintain the reduced circumference configuration in the measurement state such that the user is not required to apply continual force throughout measurement period. FIG. 23E incorporates a screw or "roller" mechanism that gradually changes the circumference, and thus creates the ability to incrementally increase or decrease transmural pressure.

Figure 24C:
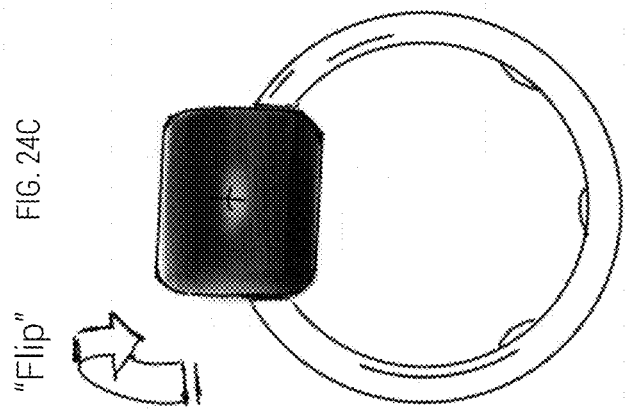
FIG. 24 shows example mechanisms to change the effective internal diameter of a ring.
Figure 24B:
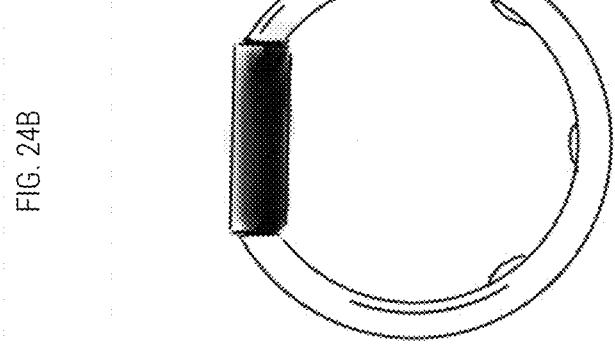
Figure 24A:
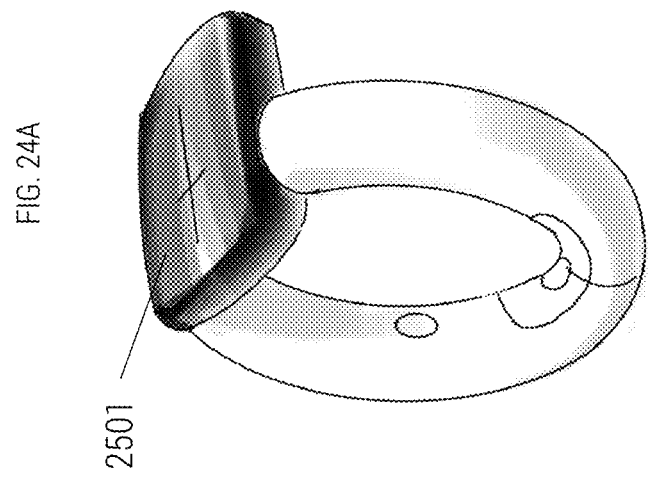
Figure 25A:
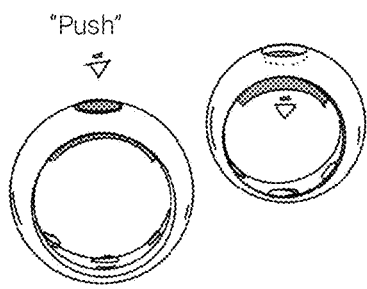
FIG. 25 shows example mechanisms to change the effective internal diameter of a ring.
Figure 25B:
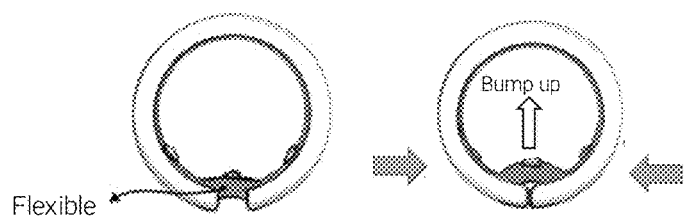
Figure 25C:
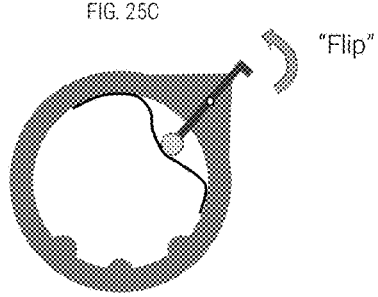

An alternative means for changing effective internal diameter is via the movement of one or more compressive features into the interior of the ring. FIG. 24 illustrates an example of an embodiment with a singular compressive feature, asymmetric block 2501, mounted on the top of the ring. In the worn state (FIG. 24A-B), the feature is rotated such that it does not compress the finger. To enter the measurement state (FIG. 24C) the user rotates the compressive features by 90 degrees where it locks into a stable configuration. The rotation of the feature creates a significant change in the effective internal diameter. FIG. 25 shows drawings of additional types of compressive feature rings. In all cases there is a mechanism for creating a protrusion within the interior of the ring via local movement. Embodiment FIG. 25A operates via a force in the radial dimension, which moves compressive feature toward the interior of the ring. Embodiment FIG. 25B operates by squeezing the ring with opposing forces in the radial dimension, forcing a flexible element to "bump up" into the interior of the ring. FIG. 25C operates via a latch, which when "flipped up" rotates a compressive into the interior of the ring.

Alternative embodiments constitute protuberance rings, which comprise a multitude of protuberances on the internal surface of the ring that change configuration. The protuberances can be connected together or act independently to change the effective internal diameter. FIG. 26 is an illustration of a protuberance ring in operation. In the wear state, the material between the ring and the finger is in a "down" state and fills a smaller volume between the ring and the finger, 2601. The material between the ring and finger is a material composed of many stiff protuberances, 2602, on a flexible supporting layer, 2603. When the ring has been rotated in a clockwise direction, the protuberances are angled toward the supporting layer and the effective internal diameter is smaller, 2604. In the measurement state, the material between the ring and finger is in an "up" state, and fills an enlarged volume state between the ring and the finger, 2605 (material enlargement exaugurated in size for clarity). When the ring is rotated in the counterclockwise direction, the protuberances are rotated or moved into a more vertical position, 2606, resulting in decreased effective internal diameter, 2607. Protuberance type materials that exhibit this type of behavior are frictional anisotropy-based systems, mohair cross country climbing skins, brushes where the "comb elements" are moderately rigid but are mounted in a material that is flexible, internally architectured materials, parallel ribs, gills, rotational blinds, and 3D printed structures to include hair-like elements. The stress and force interactions of the system have been modeled and several types of structures illustrated by Bafekrpour et. Al. Bafekrpour, Ehsan, et al. "Internally architectured materials with directionally asymmetric friction." Scientific reports 5 (2015): 10732. The protuberances can be composed of single filaments, a small block, or "pleats or blinds". If all protuberances are linked together, the movement of one can encourage the movement of other protuberances. To facilitate this coordinated conformational change, material may be placed between the protuberances so as to create a linked interaction between protuberance members. Additionally, the material between the protuberances or the attachment of the protuberances to the supporting layer may impart a configuration bias in the native or resting location of the protuberances. The material between the protuberances can be used to create a linked interaction between protuberance members or to impact a bias in the native or resting location of the protuberances. FIG. 27 is an example embodiment of a protuberance ring where only the upper half of the ring has protuberances. The illustrated ring shows an inner surface connecting the protuberances. As shown in FIG. 27, counterclockwise rotation of the ring causes a configuration change and a reduction in the internal diameter. The counterclockwise rotation of the ring results in a sight compression of inner surface, 2702, as the protuberance structure becomes more vertical, 2703. This compression creates an inherent mechanical bias that returns the structure to the wear state. The figure illustrates a connected structure but many variances in implementation exist to include independent members, parallelograms, or other geometric shapes, 2701. Many variances of the protuberance ring concept exist to include different material types, the ability to lock the ring into a measurement mode, and protuberance structures that have asymmetric bend profiles. Depending on the details of implementation, the protuberance ring concept can be implemented as the movement of one or more compressive features into the interior of the ring, as shown in FIG. 27. However, if the protuberance structure has a singular inner surface, then the result is a gross change in the inner circumference of the ring.

Figure 29:
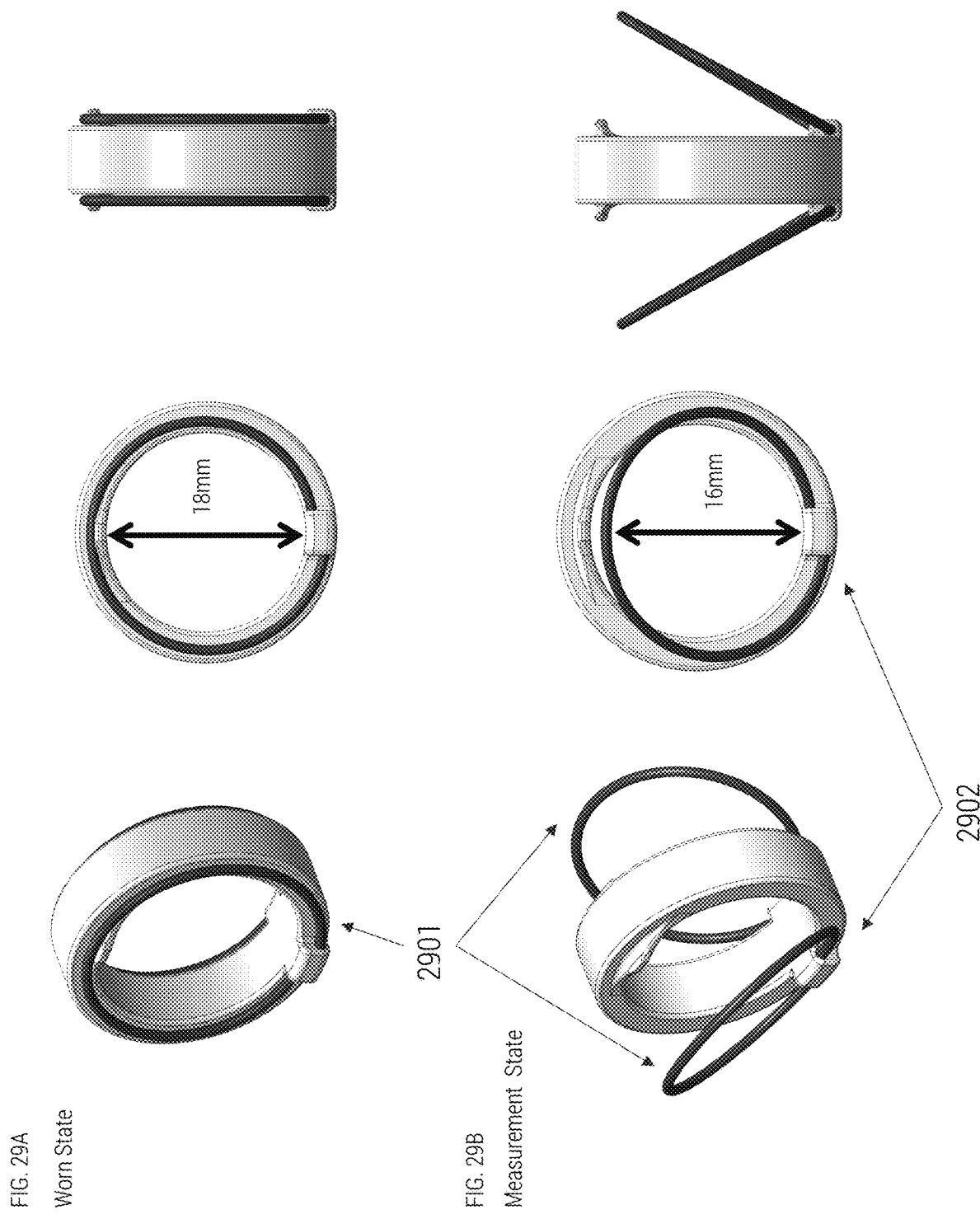
FIG. 29 shows example mechanisms to change the effective internal diameter of a ring.

Another approach for changing the effective internal diameter is through the movement of ring features along the longitudinal axis. FIG. 28 shows an example of device configured with such an approach. In the worn state configuration (FIG. 28A), the features comprising the terminal ends of the ring, 2801, abut each other in the same cross-sectional plane. The device can have mechanisms to maintain or stabilize this wear configuration, not shown. The application of opposing forces, 2802, in the longitudinal dimension causes a conformational change resulting in the measurement state configuration (FIG. 28B). In this conformation, the ends of the ring, 2801, by-pass each other in the longitudinal dimension and are no longer in the same cross-sectional plane. The resulting change in configuration decreases the effective internal diameter, and decreases the transmural pressure at the sampling site through the application of force at or in adjacency to the sampling region. The "measurement state" conformation represents the native or low stress configuration, thus the device maintains this state throughout the measurement. The ring is designed such that the inherent mechanical bias of the system is to maintain a stable measurement state. FIG. 29 presents a second example of a ring embodiment configured to reduce the effective internal diameter through the movement of features along the longitudinal axis. In the worn state (FIG. 29A), features comprising wire loops, 2901, are positioned parallel with the body of the ring. In this configuration the effective internal diameter is maximal. Via a release mechanism (not shown), the wire loops pivot away from the ring in the longitudinal dimension, resulting in a reduction of the effective internal diameter change for the measurement state (FIG. 29B). The mechanism for force in this example embodiment is generated by the wire loops: the lengthwise ends of each wire loop are oppositely coupled to the ring at a coupling point, 2902, such that that the spring/rebound rigidity of the loop creates an automatic biasing mechanism. As the wire loops pivot about the coupling point, the torsional properties of the wire loop generate a biasing force that mechanically urges the loop toward the open or expanded configuration. This inherent mechanical bias creates a stable measurement configuration. The wire loops exert force on the top of the finger, which is opposed by internal surface on the bottom of the ring, effecting a reduction in transmural pressure at the sampling region.

An additional ring embodiment capable of creating change in internal effective diameter is the respective movement of two or more rigid bodies. These rings systems can create changes in effective internal diameter via both rotational and translational movement of two rings or other geometric shapes relative to another. FIG. 30 illustrates the concept in both rotation and translation. In the rotational design, the rings rotate relative to one another, but the axis of rotation is not the same. For example, the dashed line ring rotates about point 3001. Due the non-symmetrical rotation point, the rotation leads to a change in the effective internal diameter, as show via the cross hatched area. Similar changes can be made by translating one ring or geometric shape relative to the other. In the wear configuration, the rings are concentrically located and the internal effective diameter is maximal. As one ring translate relative to the other, the effective internal diameter decreases as shown by the cross hatched area.

The above embodiments are illustrative in nature and do not represent all physical mechanisms for producing a decrease in transmural pressure. One of ordinary skill could develop multiple variants or alternatives based on the goal to change the effective internal diameter.

Stability of Measurement State

As illustrated and subsequently described, several ring embodiments require the user of the ring to maintain a force or pressure during the measurement. Examples of such user-dependent maintenance-force embodiments include those rings in illustrated in the following FIGS. 23 A-B, 23C, 25B, and 27. Other embodiments include a physical mechanism to stabilize the measurement state configuration, for example a latch or retention component: 23D 25A, and 25C. A stable measurement configuration can also be achieved via ratchet mechanisms, 19 or a screw mechanism, 23E. FIG. 24 illustrates stable condition due to the shape of the rotated element. FIG. 28 and FIG. 29 represent embodiments where the inherent mechanical bias of the system creates a stable measurement state resulting in decreased transmural pressure. Ring embodiments that have a stable measurement state can be preferred by the user as they do not require the engagement of operator during the measurement period. Additionally, these rings will generate measurement data that is not subject to movement of the ring due to the use of the other hand.

Example Methods for Hydration Assessment

The method of operation is a significant element of the invention; key information should be acquired and criteria fulfilled in the anticipated use environment, where individuals will perform the activities of daily and can engage in exercise and athletic events. Increases in physical activity will result in increased heart rate, skin contaminations, and peripheral vasodilation. The hydration assessment method of the current invention is robust to these expected conditions and potential error sources. The method of operation and associated systems make this difficult measurement by the judicious balancing of error source minimization, signal optimization, physiological signal manipulation, and feedback to the user.

Process for Hydration Determination

Figure 31:
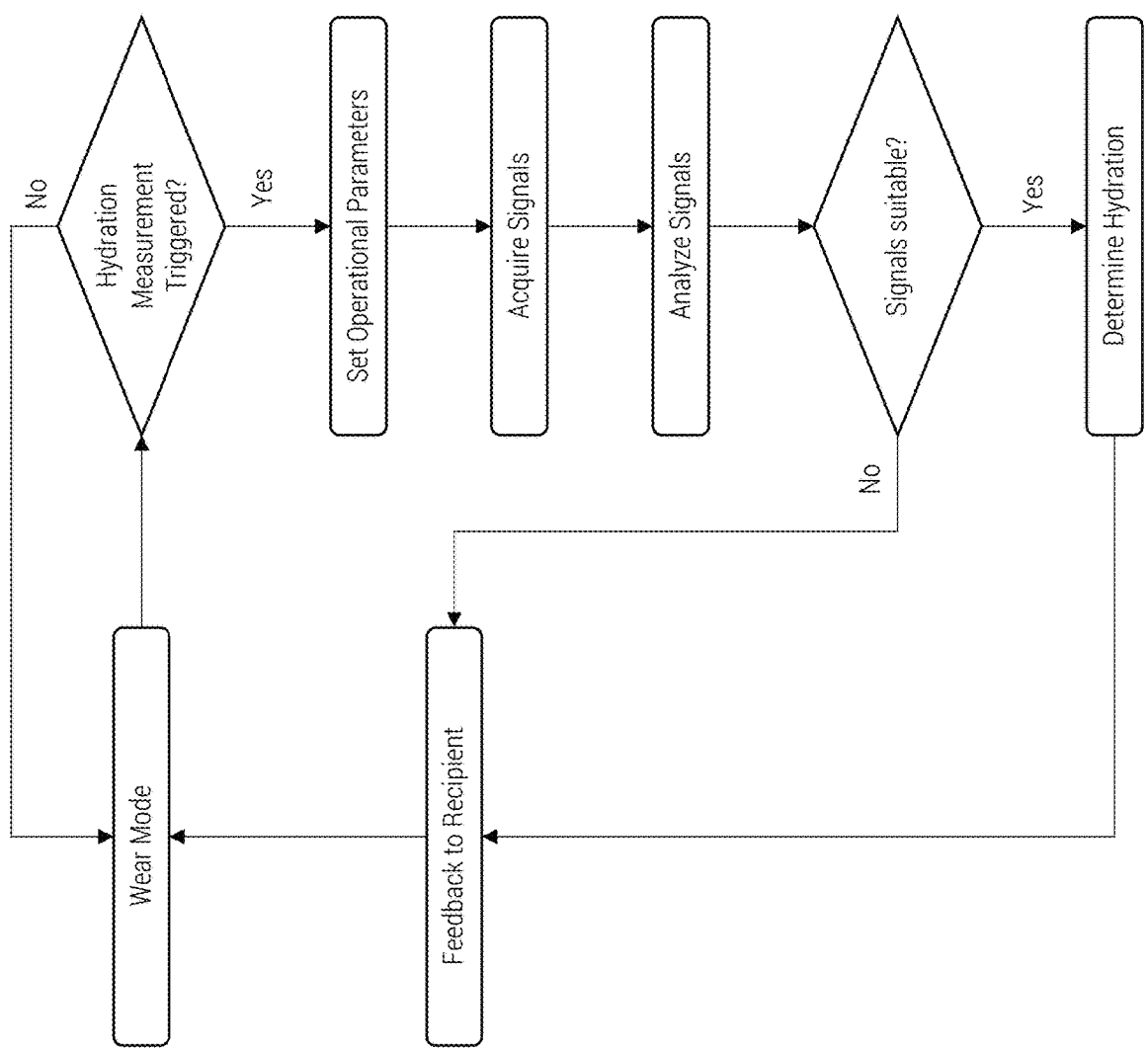
FIG. 31 presents an example of the steps to determine hydration status.

The process of obtaining a hydration measurement involves a series of steps that provide robust and reliable device performance. FIG. 31 is an example embodiment of such a process. The process for a hydration measurement is initiated by a trigger event that can be sensor-based, user-based, or time-based. Following the detection of such a trigger event, the hydration measurement process is initiated. The optical sampling control system provides a set of operational parameters to the optical sensor system. The optical sensor system, and in some embodiments the motion sensor system, then acquire signals for the designated measurement period. Following signal acquisition, the sensor signals are analyzed by the analysis system, and concurrently or subsequently analyzed for suitability by the signal suitability system. If the signal is not determined to be adequate, feedback is provided to a recipient via the feedback system. If the signal is determined to be adequate, information extracted by the analysis system, and potentially other systems, is provided to the hydration determination system. A hydration status is determined, and this information is provided to the recipient. Following this step, the device can enter an "idle" state in "wear mode" with a modified set of functions (e.g., assessment of user motions and heart rate) while waiting for another trigger event to be detected.

Triggering a Hydration Measurement

Figure 32:
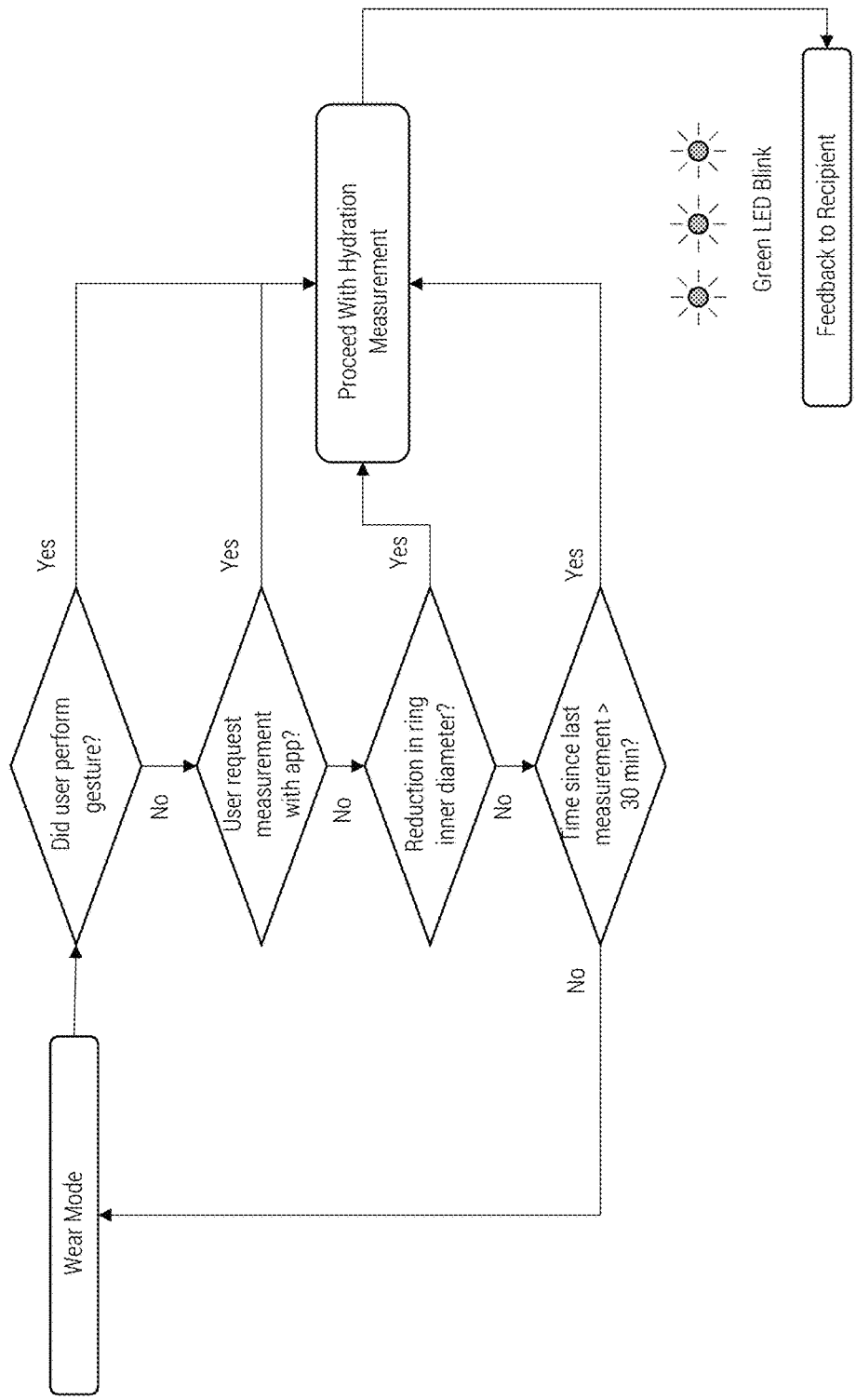
FIG. 32 presents an example process for triggering a hydration measurement and providing feedback.

An example of a hydration measurement trigger subprocess is illustrated in FIG. 32. The disclosed embodiment contemplates a variety of triggering methods. In this example process, hydration measurements are triggered only when requested by the user (by means of a specific gesture, interaction with a connected device, or physical deformation of the ring), or if a significant time interval has passed since the last measurement. In this example embodiment, feedback is provided to the user regarding hydration determination status: if a measurement process is triggered, indicator LEDs blink green in succession. In alternative embodiments feedback can take other forms. This example trigger subprocess supports battery conservation, a vital objective for small wearable systems. Hydration measurements are performed only every 30 minutes unless specifically triggered by the user. Practically speaking, there is little need for more frequent hydration determinations since physiological changes in systemic hydration are relatively slow, occurring over tens of minutes to hours.

Alternative Process for Hydration Determination

Figure 33:
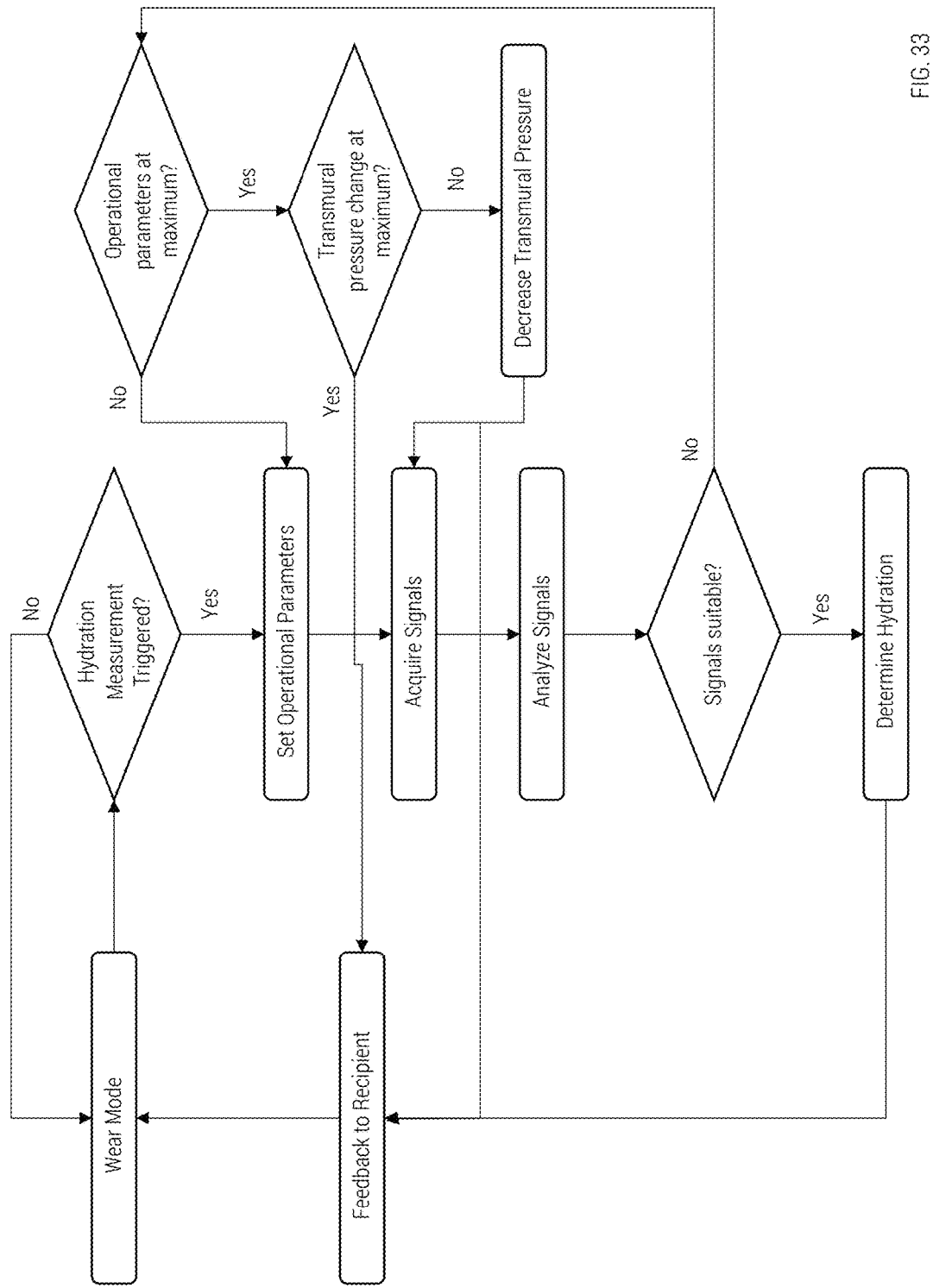
FIG. 33 presents an example process for determining hydration status with the possible variation of operational parameters and transmural pressure.

FIG. 33 presents an alternative process for hydration determination that includes coordinated interaction between systems, power management, and user involvement to achieve a reliable result. As in FIG. 31, following a trigger event, the optical sampling control system designates a set of operational parameters to the optical sensor system and signals are acquired from one or more sensor systems. Deviations from FIG. 31 begin after the evaluation of signals for suitability. If the suitability metric indicates that the signals are inadequate, then the optical sampling control system can change the operational parameters, and the signal acquisition/analysis steps are repeated.

In cases where signal inadequacy is due to failed or unreliable detection of aortic valve opening or closing, changes in the optical system operational parameters can achieve signal suitability. As an example, high-fidelity sampling defines a class of operational parameters that supports the detection of both the aortic valve opening and aortic valve closing events and comprises any combination of increased sampling rate, increased light intensity, increased detector integration time, and increased sample averaging. These increases are defined relative to operational parameters used in standard-fidelity sampling that enables only detection of aortic valve opening or related signals, i.e., heart rate determination. The use of high-fidelity sampling comes at an expense, as it consumes far more power than that required by standard-fidelity sampling. The additional power consumption creates a challenge for wearable devices with limited battery sizes and a mandate for power conservation to prolong battery life. Thus, embodiments of the invention can employ high-fidelity sampling only as necessary and in a staged manner to prolong battery life to the extent possible.

In some embodiments, changes to operational parameters can also include changes in emitter wavelength and the set of active emitters and detectors to affect the optical path and the vascular structures with which photons interact. Shorter wavelengths in the visible range and selection of proximal emitters and detectors encourages reflection dominant sampling, i.e., optical sampling of the tissue where the majority of photons do not penetrate deeply into the tissue and primarily interact with (i.e., are reflected by, scattered by, or absorbed by) vessels in the capillary bed. Longer wavelengths in the near infrared range and selection of emitters and detectors with greater physical separation (>5 mm) encourages transmission dominant sampling, i.e., optical sampling of the tissue where the majority of photons penetrate and travel through the tissue, interacting with (i.e., reflected by, scattered by, or absorbed by) tri-layered vessels. Though detection of aortic valve closure is typically aided by transmission dominant sampling, reflection dominant sampling can be preferred during with greater user motion since reflection dominant signals are less likely to be contaminated by venous sources. Thus, an example embodiment can first acquire signals with a set of operational parameters consistent with transmission dominant sampling, then depending on signal suitability, acquire additional signals with a second set of operational parameters consistent with reflection dominant sampling.

If a suitable signal has not been acquired and operational parameters are at a maximal level (e.g., LED drive current cannot be safely increased), or the power consumption or battery usage exceed defined thresholds, then additional steps can be taken. As illustrated in FIG. 33, decreases in transmural pressure can be used to improve signal quality. Transmural pressure decreases can be achieved with a variety of processes, to include (1) raising the sampling region relative to the level of the heart, (2) manually pushing the device against the sampling region, (3) moving the device to another sampling region (such as a region of the same finger with a larger circumference, or a different finger with a larger circumference) such that greater external pressure is applied, or (4) reducing the effective internal diameter of the device such that greater external pressure is applied to the sampling region. These processes can be used alone or in combination to create the desired effect. As these changes require the active participation of the user, feedback to the user is provided. As signals are acquired and analyzed, the signal suitability system can continuously access whether the decreases in transmural pressure have created the desired effect of suitable signals. In some embodiments, the system can modify operational parameters concurrently, in parallel, or in sequence with changes in transmural pressure to achieve suitable signal with the minimal power expenditure. Depending on the mechanism for reducing transmural pressure, the changes can be incremental (e.g., gradually raising a finger on which the device is worn, or slowly reducing the effective internal diameter using an embodiment of the device like that illustrated in FIG. 23E) or discrete (e.g., moving the device to another finger region or using an embodiment of the device like that illustrated in FIG. 28). The desired extent of transmural pressure decrease is limited: decreasing the arterial transmural pressure below zero at diastole by any mechanism or combination of mechanisms will begin to occlude arterial flow and distort the pulse waveform. Additional decreases in transmural pressure beyond this point will not improve the signal, and might render the signal unsuitable for hydration determination. As shown in the example process in FIG. 33, feedback is provided to the user if the maximum achievable reduction in transmural pressure change has been produced and the signal remains unsuitable for hydration determination.

Opportunistic Sampling. Depending on the frequency of hydration measurements desired, the state of the user, and the time of day, opportunistic sampling can be effective in simplifying device operation and conserving battery life. For example, consider two distinct activities: sleeping and vehicle operation. During either activity, the device can engage in opportunistic sampling during periods when little or no motion is present (as determined by embedded accelerometers). In the case of sleeping, the supine posture can aid in creating large pulsatile and when driving the act of resting the hand on the steering wheel or gear shift might create a desired decrease in transmural pressure. If the system detects strong pulsatile signals (as determined with standard-fidelity sampling during "wear mode" operation), the device can trigger initiation of hydration determination and implement high-fidelity sampling. As one can appreciate, there exist both active (e.g., user involved) and passive (i.e., opportunistic) methods for acquiring signals that are enable the determination of aortic opening and closure and are suitable for hydration determination.

Demonstration of System

Hydration Assessment During Exercise-Induced Hypertonic Dehydration. To demonstrate the feasibility of hydration assessment using the present invention, an exercise-induced dehydration protocol was performed. A subject exercised at a moderate exertion level in a heated room (78 deg) without fluid consumption for 60 minutes. The test subject then entered a recovery phase, using oral rehydration to replenish fluids at a consumption rate supported by prior studies with the objective of restoring the subject's weight to the baseline value. Reference and novel measurements of hydration were performed at baseline (pre-exercise), immediately following exercise, and at approximately one-hour increments throughout the recovery phase. Reference hydration measurements included nude weight, urine output, urine specific gravity, and urine color. The novel hydration measurements were made with the current invention. The aortic valve time sequence was acquired using a near-infrared photoplethysmography (PPG) sensor placed at the base of the finger while the subject rested in a single body position (standing).

Figure 34A:
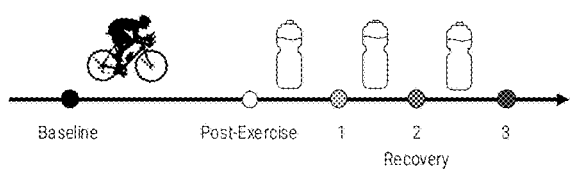
FIG. 34 illustrates measurement results during exercise-induced hypertonic dehydration.

FIG. 34A shows a schematic of the study protocol, indicating the timing of measurement periods relative to cycling and incremental rehydration. FIG. 34B shows the percent weight change of the subject over time. FIG. 34C shows the amount of fluid consumed in each phase and FIG. 34D shows the change in the color of the urine at each measurement. As seen in many previous studies, urine-derived indices of hydration will lag behind weight due to filling of the bladder. FIG. 34E shows the noninvasive hydration assessments obtained from an embodiment of the invention. IBI and ET were extracted from the PPG measurements and were entered into a linear hydration determination model. Examination of the figure shows a strong relationship between the measurements results and the hydration status of the subject as defined by weight change.

To confirm the specificity of the novel measurements for hydration versus other physiological changes associated with exercise, a second study was conducted. FIG. 35A shows the general experimental design and protocol variants. In Protocol 1, a subject repeated the exercise-induced dehydration as described above. The subject lost considerable fluid resulting in a 4.5% loss of body weight due to fluid loss. On a second day, the subject performed Protocol 2, exercising in identical conditions with matched power output, but consuming fluids during exercise at a rate consistent with the sweat rate. This protocol was designed to minimize hydration changes in the presence of significant physiological changes induced by exercise. Examination of FIG. 35B shows that the subject's weight was maintained during the exercise period via the consumption of nearly 2 L of fluid (FIG. 35C). FIG. 35D shows that in protocol 2, urine was largely unchanged, or perhaps even lighter following exercise. Examination of the results generated with aortic valve opening and closing in FIG. 35E shows a clear distinction between the protocols, with Protocol 2 showing little change or even a slight increase in hydration status following exercise.

The experimental design illustrated in FIG. 35A was repeated in a larger study involving 11 competitive cyclists. Participants completed a standardized cycling protocol in the absence or presence of oral fluid replenishment. Reference hydration status, assessed at ~1.5 hour intervals during dehydration and subsequent rehydration, was determined from percent weight change and urine specific gravity. When exercising in the absence of fluid replenishment, subjects maximally lost between 2.1 and 3.6% body weight, with a mean of 2.8±0.5% (mean±SD). When exercising in the presence of prescribed rehydration, subjects lost an average of 0.4±0.5%.

Using the inputs and determination model approach outlined in FIG. 17, hydration status was assessed based on noninvasive measurements of IBI and ET. In all subjects, estimated hydration status was significantly reduced at peak dehydration relative to a euhydrated baseline, and a rehydrated recovery period (P<0.0001 in all cases, corrected for multiple comparisons, two-sample t-tests). Incorporating data from all subjects and visits (n=176 observations), binary classifiers were trained to detect 1.5% dehydration. Models achieved greater than 90% accuracy and ROC area under the curve (AUC) values exceeding 0.90 when tested on unseen data, using a 5-fold cross-validation approach.

Hydration Assessment During Simulated Changes in Isotonic Hydration

Figure 36:
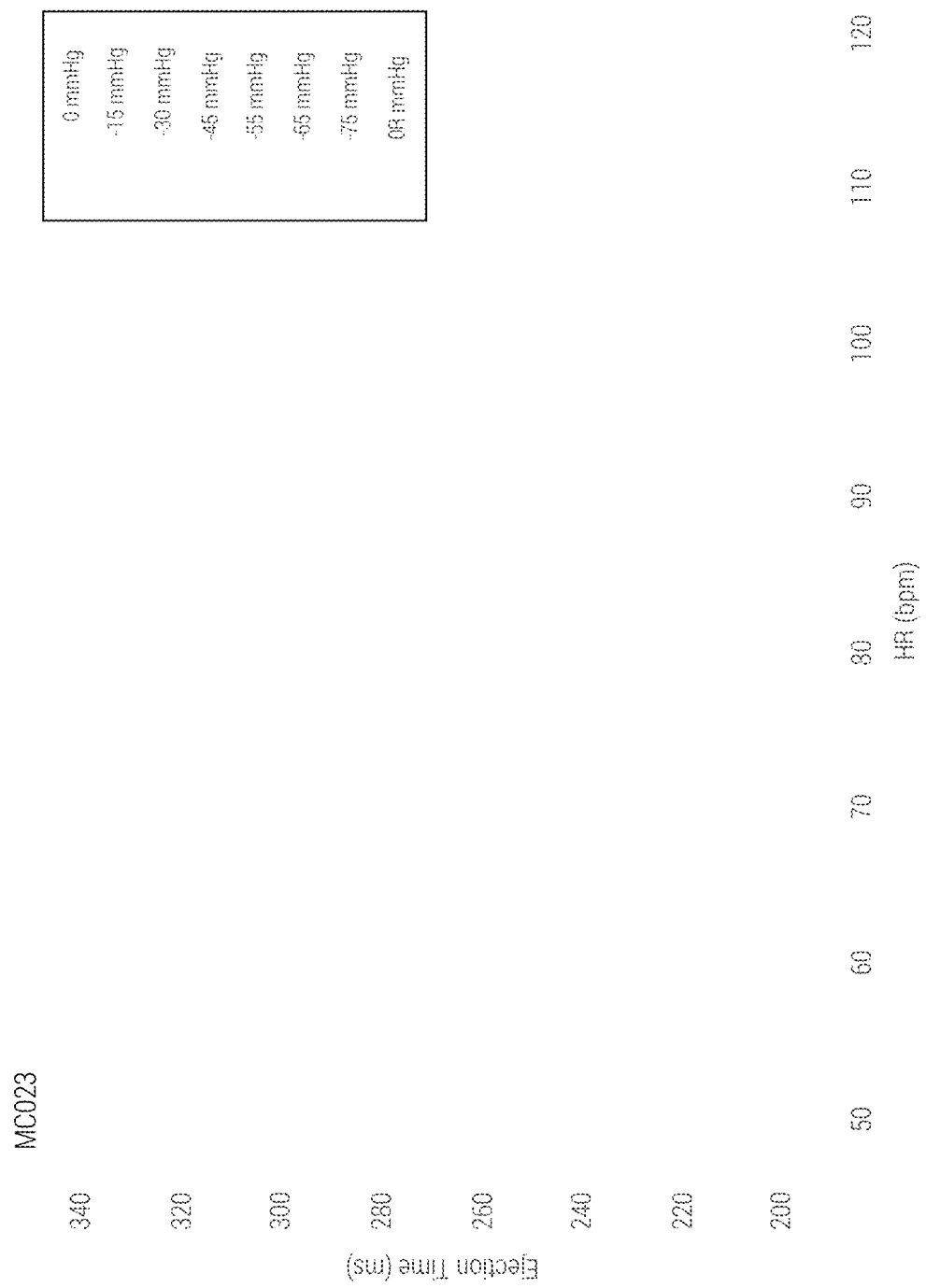
FIG. 36 illustrates heart rate and ejection time during simulated isotonic dehydration.

An additional demonstration of an example embodiment of the invention was pursued via changes in plasma volume at a fixed body position, without exercise, or associated changes in body temperature. Lower Body Negative Pressure is an experimental approach for inducing decreases in vascular volume and creates a simulated state of isotonic dehydration. The use of lower body negative pressure pulls blood into the lower body and creates transient dehydration via hypovolemia that can be reversed rapidly. FIG. 36 shows the valuable insights available by effectively processing the aortic valve information. The aortic valve time sequence information was recorded using a near-infrared PPG sensor from the tip of the finger. Negative pressures between 0 and 75 mmHg were used, and the pressure was held for approximately 10 minutes at each level. Dashed lines represent the least-squares linear fit to the HR vs ejection time data at each pressure. The "0R" condition indicates the recovery period. The increase in heart rate that occurs between negative pressure changes represents the physiological response to maintain cardiac output. Examination of the figure shows a defined grouping of points with each simulated dehydration level. The plot effectively demonstrates how ejection time and heart rate can be used to define the hydration state of the user.

A second experiment manipulating hydration status was conducted to simulate isotonic dehydration as well as hyperhydration. Changes in circulating volume were induced with lower body negative pressure or lower body positive pressure. Lower body pressure was varied from −30 mmHg to +40 mmHg in discrete stages. Thirteen healthy male subjects, ranging in age from 19 to 39 years, were recruited to take part in the study.

Figure 37A:
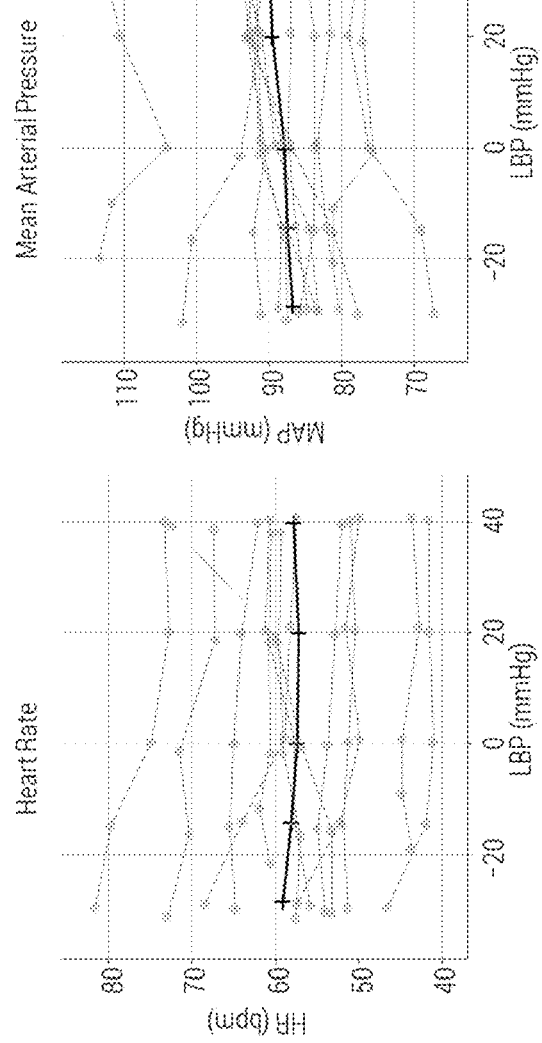
FIG. 37 shows heart rate, mean arterial pressure, and ejection time during simulated changes in hydration.
Figure 37B:
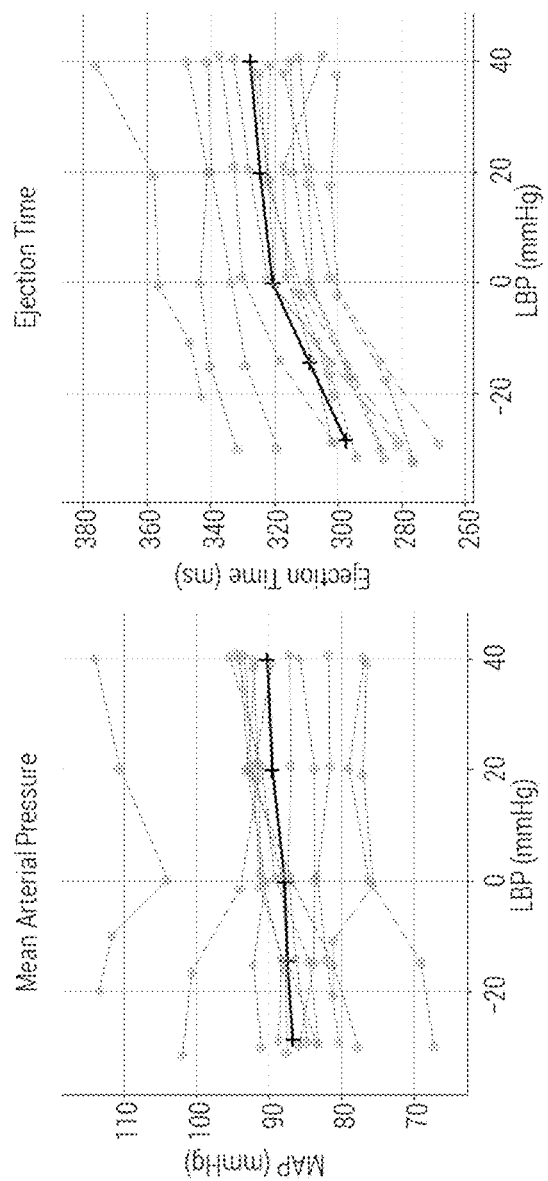
Figure 37C:
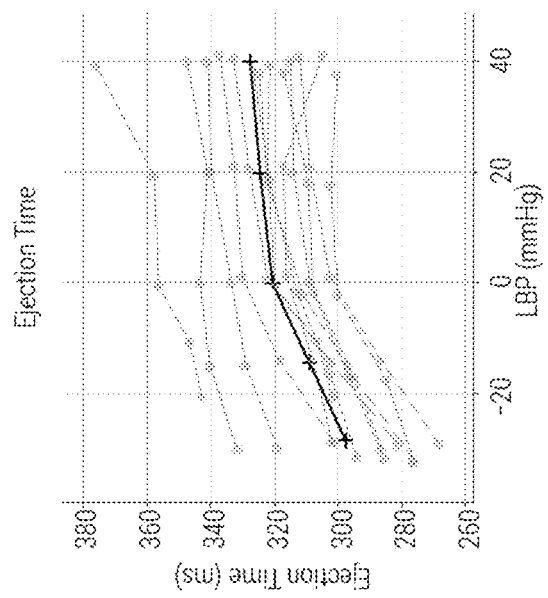
Figure 38:
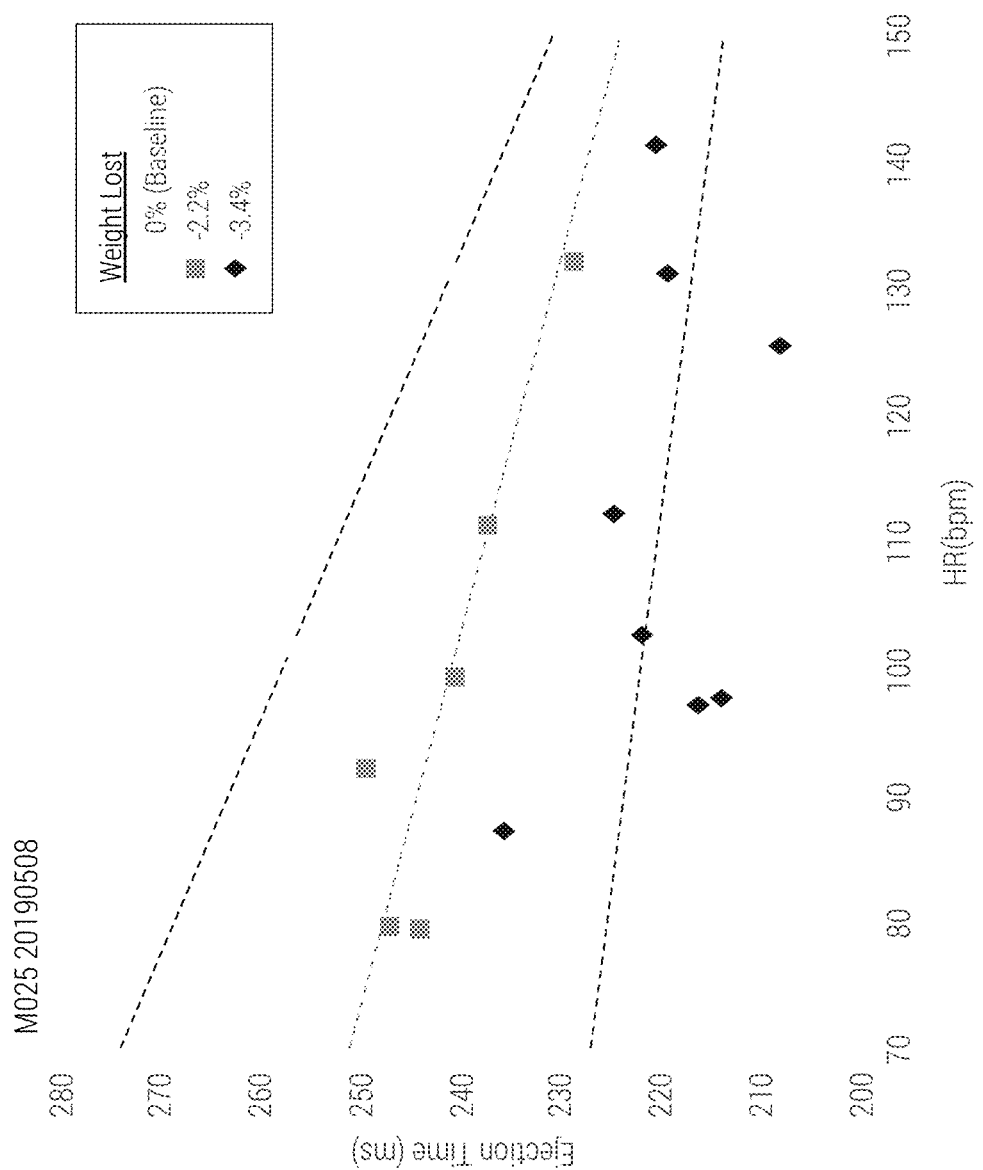
FIG. 38 illustrates heart rate and ejection time acquired during exercise.

Average heart rate (HR), mean arterial pressure (MAP), and ejection time as a function of lower body pressure (LBP) are shown FIG. 37. Lighter lines represent each individual subject while darker lines with cross denotes the group mean. Effects of lower LBP on HR (FIG. 37A) and MAP (FIG. 37B) were relatively subtle and heterogeneous across the sample. Using a repeated measures analysis of variance (ANOVA) test to assess differences across conditions, no significant changes in HR were found at the group level ($F_{4,12}=0.7$, p=0.48), while MAP showed a trend toward increasing with LBP ($F_{4,12}=2.3$, p=0.069). In contrast, negative LBP decreased ejection time in a graded fashion and positive LBP slightly increased ($F_{4,12}=55.0$, $p<10^{-16}$). Within-subject one-way ANOVAs confirmed a strong effect in all subjects (p<0.005, corrected for multiple comparisons). These results stress the unique value of ejection time to detect changes in hydration status and by comparison, the relative insensitivity of HR and MAP to mild changes in circulating volume.

Hydration Assessment While Exercising. An exercise study without fluid replacement was conducted. At the beginning, middle and end of the exercise period the subject was asked to explicitly vary their heart rate over a pre-defined range by changing power output. FIG. 37 is a plot of the results obtained. The aortic valve time sequence information was recorded using a near-infrared PPG sensor on the tip of the finger. Examination of the plots shows the very distinct grouping of points as the subject became increasingly dehydrated. Moreover, the data demonstrates the ability to determine hydration status while subjects experience heart rate changes during a significant exertion.

Hydration Assessment with Positional Change. FIG. 39 demonstrates the value of using body position changes to enhance or augment the hydration assessment. The exercise-induced dehydration study protocol was executed as before, but the subject moved through supine, sitting and standing body positions during each measurement period. The sequence of aortic valve opening and closing was obtained using a near-infrared PPG sensor placed at the base of the finger. The heart rate and ejection time measurements during each period and body position are shown in FIG. 39A. As seen in the figure, the initial baseline measurements show minimal change in heart rate and an ejection time change of 60 ms. However, with change in hydration of 2.5%, the degree of change due to position is significantly larger with a heart rate change ~16 beats per minute and a change in ejection time of 115 ms. As the subject recovers, the degree of posture-induced changes decreases until near-baseline changes are observed.

The addition of positional change information adds additional information on hydration status that can be effectively incorporated as illustrated in FIG. 18. FIG. 39B shows the output of a hydration determination model that linearly combines changes in IBI and ET from supine to standing positions to provide a hydration assessment. The ability to obtain positional change information can occur passively as a user exits from a bed in the morning or moves from a desk to a standing position when at work.

Scenarios for System Use

The following use cases are provided to help illustrate the value and inventive nature of the system. The presented use cases comprise limited examples and one of skill in the art will recognize additional scenarios where the invention is of use.

Military Operations. An embodiment of the current invention can be used for military personnel who are at risk for dehydration due to body armor requirements and overall physiological stress due to military operations. Military personnel don significant protective gear in extreme environmental conditions that can include the risk of combat. Collectively, these conditions can place enormous physiologic stress on the body with physical and cognitive consequences. One can appreciate the problem by considering military units operating in the Middle East. Despite a focus on water consumption to keep soldiers in good health, combat conditions can create significant distractions that when coupled with 110° F. temperatures create an ideal environment for decreased physiological performance. Dehydration also puts soldiers at greater risk for loss of life should they become injured in combat; in the event of hemorrhage (isotonic dehydration), the body's ability to maintain sufficient perfusion to vital organs is severely compromised when baseline vascular volume is already reduced. The described hydration assessment system can provide oversight of vascular volume with no additional burdens in soldiers' time, behavior, or gear. Thus, the invention has significant value to military personnel.

Elderly Patient Assessment. An embodiment of the current invention has applicability in monitoring the hydration status in the elderly due to limited reserves and the consequences of a fall or loss of cognitive function. With increasing age, body water content decreases, the risk for dehydration increases, and the consequences become more serious. Additionally, the "drink to thirst" mechanism loses effectiveness. Dehydration has been associated with increased mortality rates among hospitalized older adults and can precipitate emergency hospitalization and increases the risk of repeated stays in hospital. Dehydration is a frequent cause of hospitalization of older adults and one of the ten most frequent diagnoses responsible for hospitalization in the United-States. Evidence suggests high dehydration rates of elderly patients within hospitals and other health care institutions and is considered a form or abuse. The impact of dehydration is associated with various morbidities, such as impaired cognition or acute confusion, falling or constipation. Dehydration has been linked to increased risk of stroke and myocardial infarction. The expenditures linked to dehydration are significant as evidenced in a 1999 study that estimated the avoidable costs of hospitalizations due to dehydration at $1.14 billion. Insufficient fluid intakes result from limitations such as reduced swallowing capacity, decreased mobility, or comprehension and communication disorders.

Assessment of hydration in the elderly demonstrates the value of the invention for the avoidance of falls, cognitive lapses, increased risk of cardiovascular events, and kidney stone developments. In this scenario the feedback system can be configured to report status information to a family member, a remote monitoring service, or to a nursing station in an assisted living setting. The system can use the postural transitions from sleeping to sitting to standing as a method for accessing aortic valve timing under three different venous return conditions. The ability to compare day-to-day trends for a single individual enables the detection of small perturbations that can be important in the physiologically fragile individual.

Daily Living. An embodiment of the current invention has general applicability to the general population. For the purpose of illustration consider a business executive on international travel. The dry air used to pressurize jet airplane cabins coupled with limited beverage service leads to volume depletion. The executive can use a hydration assessment system to effectively ensure that fluid intake is appropriate. The burden on the user is minimal and only requires the executive to don a ring or other wearable device such that aortic valve opening and closing information is obtained.

Post-Exercise Assessment. An embodiment of the current invention also has applicability for any athlete looking to recover for exercise. An example scenario can involve a vigorous skiing day with friends. The ability of an individual to self-assess their hydration status can be impeded due to several factors, e.g., the dryness of high mountain air, increased respiratory rate due to decreased oxygen concentration resulting in increased respiratory fluid loss, perspiration on very challenging ("black diamond") runs, and after-ski consumption of alcohol, a known diuretic. The hydration assessment system can provide information for optimal fluid intake and recovery so that the second day of the ski trip is as enjoyable as the first. Other use case scenarios include back-to-back soccer games, tennis tournaments, multi-day sailing tournaments, 18 holes in the holes of golf in the Arizona sun and training for a marathon.

Within-Exercise Assessment. An embodiment of the current invention can be used by athletes for hydration maintenance during exercise. Use scenarios include any endurance events where the "drink-to-thirst" approach has been shown to ineffective. The Hawaii Ironman is an event known for epic collapses due to hydration mismanagement. A similar event known for hydration complexities is the La Ruta mountain bike race across Costa Rica. Many North America athletes travel to Costa Rica to participate in the event but have little experience with the tropical humid environment and are also concerned with drinking untreated water. The event is a significant endurance event with the cycling time often exceeding 4 hours. The ability to use the physiological assessment system to determine circulating volume during the event can have profound value, allowing athletes to maintain hydration at baseline levels throughout the event. The system can provide real-time assessments of hydration status, displayed on a standard cyclometer device, as well as alerts if circulation volume was changing rapidly or progressing to dangerously low levels.

Figure 40B:
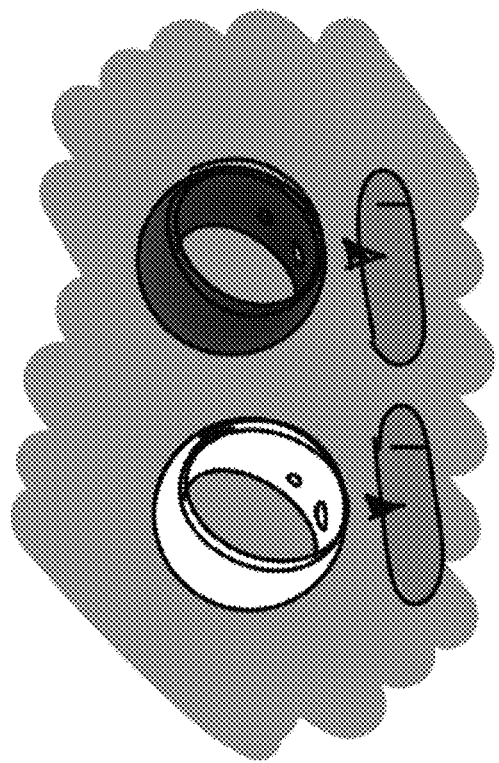
FIG. 40 shows examples of pairs of rings that may be provided to a user.
Figure 40A:
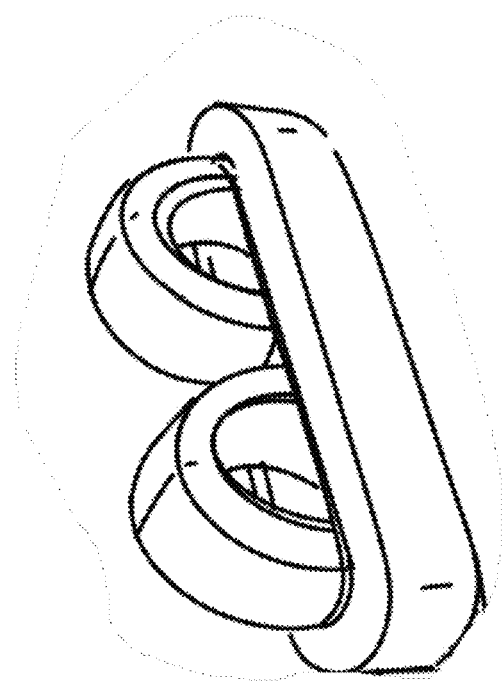

Multiple Rings for Convenience. In ring-type embodiments, the small device size significantly limits battery size and power capacity. As discussed above, processes can be implemented for battery conservation. Alternately or in addition, a set of two or more devices may be provided to the user, such that one device can be charging while another device is worn. FIG. 40A shows an example of a pair of rings. One ring may be worn during the day, while the other is worn at night. Alternatively, one ring may be worn until a notification of low battery is provided, encouraging the user to "swap" the ring for the second ring. As shown in FIG. 40B, the pair of rings may have appearances distinct from each other, which facilitate ring swapping. Such embodiments provide a convenient solution for users to continuously wear a hydration determination device.

Each of the publications referred to herein are incorporated herein by reference.

The aortic time course detected via the invention also allows for the determination of other parameters such that a general physiological assessment system is possible. Such a system can provide the user with information on one or more of sleep quality and duration, stress, activity, and heart rate. These additional parameters are derivable from the apparatus used for hydration assessment.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

While the concepts of the present disclosure are susceptible to various modifications and alternative forms, specific embodiments thereof have been shown by way of example in the drawings and described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described can include a particular feature, structure, or characteristic, but not every embodiment must necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments can be implemented, in some cases, in hardware, firmware, software, or any combination thereof. The disclosed embodiments can also be implemented as instructions carried by or stored on a transitory or non-transitory machine-readable (e.g., computer-readable) storage medium, which can be read and executed by one or more processors. A machine-readable storage medium can be embodied as any storage device, mechanism, or other physical structure for storing or transmitting information in a form readable by a machine (e.g., a volatile or non-volatile memory, a media disc, or other media device).

In the drawings, some structural or method features are shown in specific arrangements and/or orderings. However, it should be appreciated that such specific arrangements and/or orderings might not be required. Rather, in some embodiments, such features can be arranged in a different manner and/or order than shown in the illustrative figures. Additionally, the inclusion of a structural or method feature in a particular figure is not meant to imply that such feature is required in all embodiments and, in some embodiments, might not be included or might be combined with other features.

What is claimed is:

1. An apparatus for determining the hydration status of a user, comprising:
   (a) a ring, having an internal surface with an effective internal diameter, configured to be worn around a finger of the user;
   (b) an optical sensor system comprising (i) one or more optical emitters mounted with the ring such that light emitted by the one or more emitters is directed toward the finger and (ii) one or more detectors mounted with the ring such that the one or more detectors produce a detector signal representative of light reaching the detectors from one or more emitters after the light has interacted with tissue of the finger, configured to detect physiological signals indicative of opening and closing of the user's aortic valve;
   (c) a trigger system, configured to detect an event indicating a hydration measurement is to be initiated;
   (d) an optical sampling control system responsive to the trigger system configured to operate the one or more emitters and the one or more detectors at a set of operational parameters;
   (e) an analysis system responsive to the detector signal and configured to determine an interbeat time interval between successive openings of the user's aortic valve, and an ejection time interval between opening and closing of the user's aortic valve;
   (f) a hydration determination system configured to determine the hydration status of the user from the interbeat time interval and the ejection time interval;
   (g) a feedback system configured to provide feedback.

2. The apparatus of claim 1, further comprising a user input system, and wherein the trigger system is responsive to the optical sensor system, the user input system, or a combination thereof.

3. The apparatus of claim 1, further comprising a motion sensor system comprising an accelerometer, a gyroscope, or a combination thereof; and wherein the trigger system is responsive to the motion sensor system.

4. The apparatus of claim 1, wherein the feedback system comprises one or more LEDs or haptic sensors mounted with the ring.

5. The apparatus of claim 1, wherein the feedback system comprises a portion an external to the ring and a portion mounted with the ring, wherein the portion external to the ring comprises a visible display.

6. The apparatus of claim 1, wherein the one or more optical emitters and the one or more detectors are mounted with the ring such that light reaching the detector comprises a majority of photons that have traveled through the tissue and interacted with tri-layered vessels.

7. The apparatus of claim 1, wherein an angle between an emitter and a detector, measured from the center of the ring, is greater than 15 degrees.

8. The apparatus of claim 1, wherein the ring is configurable to assume a plurality of effective internal diameters such that, when the ring is configured to a first effective internal diameter, the venous transmural pressure in the tissue of the finger that has interacted with the light is less than zero and the arterial transmural pressure at diastole in the tissue of the finger that has interacted with the light is greater than zero.

9. The apparatus of claim 8, wherein the ring is configurable to one of two stable states wherein the first stable state the ring has a first effective internal diameter, and wherein the second stable state the ring has a second effective internal diameter distinct from the first effective internal diameter.

10. The apparatus of claim 9, wherein the ring has a mechanical bias that encourages the ring to the second stable state.

11. The apparatus of claim 10, wherein the second effective internal diameter is less than the first effective internal diameter.

12. The apparatus of claim 8, wherein the trigger system comprises a sensor sensitive to a change in the effective internal diameter of the ring.

13. The apparatus of claim 8, wherein the ring comprises one of more compressive features that protrude from the inner surface of the ring, and wherein the effective internal diameter is altered by the movement of the one of more compressive features.

14. The apparatus of claim 8, wherein the ring comprises one or more ring features, and wherein the effective internal diameter is altered by movement of the one or more ring features along the longitudinal axis.

15. The apparatus of claim 8, wherein the ring has a reducible internal circumference.

16. The apparatus of claim 8, wherein the ring has ring features comprising protuberances on the inside of the ring whose configurations can be changed between first and second configurations, wherein the ring has a first effective internal diameter when the protuberances are at the first configuration and a second effective internal diameter, different from the first effective internal diameter, when the protuberances are at the second configuration.

17. The apparatus of claim 1, wherein the ring is configurable to assume a plurality of effective internal diameters such that the ring can be configured to a first effective internal diameter, producing a first set of transmural pressures in blood vessels in the tissue of the finger, and to a second effective internal diameter, producing a second set of transmural pressures in the blood vessels, where the pressures in the second set of transmural pressures are smaller than the pressures in the first set of transmural pressures.

18. The apparatus of claim 1, wherein the analysis system is further configured to determine the detector signal as not suitable for hydration determination based on one or more of: detection of motion of the tissue of the finger, the ring, or a combination thereof; detection of pulsatile physiological signals too small for pulse analysis; detection of lack of persistent contact with the tissue of the finger; inability to detect aortic valve opening or closing; lack of changes in transmural pressure; instability of physiological signals; and inconsistency of features extracted from the physiological signals.

19. The apparatus of claim 18 further comprising a motion sensor system, and wherein the analysis system is configured to determine the detector signal as not suitable responsive to the motion sensor system.

20. The apparatus of claim 18, wherein the optical sampling control system is configured to change the set of operational parameters responsive to the determination that the detector signal is not suitable as determined by the analysis system.

* * * * *